United States Patent
Boye et al.

(10) Patent No.: US 11,744,851 B2
(45) Date of Patent: *Sep. 5, 2023

(54) ENHANCING AAV-MEDIATED TRANSDUCTION OF OCULAR TISSUES WITH HYALURONIC ACID

(71) Applicant: University of Florida Research Foundation, Incorporated, Gainesville, FL (US)

(72) Inventors: Shannon E. Boye, Gainesville, FL (US); Sanford L. Boye, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/467,555

(22) Filed: Sep. 7, 2021

(65) Prior Publication Data
US 2022/0062325 A1    Mar. 3, 2022

Related U.S. Application Data

(63) Continuation of application No. 16/914,230, filed on Jun. 26, 2020, now Pat. No. 11,141,425.

(60) Provisional application No. 62/867,596, filed on Jun. 27, 2019.

(51) Int. Cl.
| | | |
|---|---|---|
| A61K 31/728 | (2006.01) | |
| A61K 9/00 | (2006.01) | |
| A61P 17/00 | (2006.01) | |
| C07K 16/28 | (2006.01) | |
| A61K 35/761 | (2015.01) | |
| A61K 9/51 | (2006.01) | |
| A61K 39/00 | (2006.01) | |

(52) U.S. Cl.
CPC .......... *A61K 31/728* (2013.01); *A61K 9/0019* (2013.01); *A61K 9/5184* (2013.01); *A61K 35/761* (2013.01); *A61P 17/00* (2018.01); *C07K 16/2875* (2013.01); *A61K 2039/5258* (2013.01); *A61K 2800/91* (2013.01)

(58) Field of Classification Search
CPC .. A61K 31/728; A61K 9/0019; A61K 9/5184; A61K 35/761; A61K 2800/91; A61K 2039/5258; A61P 17/00; C07K 16/2875
See application file for complete search history.

(56) References Cited

U.S. PATENT DOCUMENTS

| | | | |
|---|---|---|---|
| 7,144,870 B2 | 12/2006 | Chaudhuri | |
| 11,141,425 B2* | 10/2021 | Boye | A61K 9/5184 |
| 2010/0015158 A1 | 1/2010 | Robinson | |
| 2015/0225741 A1 | 8/2015 | Horsager et al. | |
| 2017/0096683 A1 | 4/2017 | Scaria | |
| 2020/0038432 A1 | 2/2020 | Kwon et al. | |
| 2020/0405744 A1 | 12/2020 | Boye et al. | |

FOREIGN PATENT DOCUMENTS

| | | |
|---|---|---|
| WO | WO 03/47525 A2 | 6/2003 |
| WO | WO 2012/145601 A2 | 10/2012 |
| WO | WO 2018/134168 A1 | 7/2018 |
| WO | WO 2018/156654 | 8/2018 |

OTHER PUBLICATIONS

Rey-Rico et al., Effective and durable genetic modification of human mesenchymal stem cells via controlled release of rAAV vectors from self-assembling peptide hydrogels with a maintained differentiation potency, Feb. 21, 2015, Acta Biomaterialia, vol. 18, pp. 118-127. (Year: 2015).*
Invitation to Pay Additional Fees for Application No. PCT/US2020/040004 dated Sep. 23, 2020.
International Search Report and Written Opinion for Application No. PCT/US2020/040004 dated Dec. 8, 2020.
Boye et al., Highly Efficient Delivery of Adeno-Associated Viral Vectors to the Primate Retina. Hum Gene Ther. Aug. 2016;27(8):580-97. doi: 10.1089/hum.2016.085.
Dalkara et al., In vivo-directed evolution of a new adeno-associated virus for therapeutic outer retinal gene delivery from the vitreous. Sci Transl Med. Jun. 12, 2013;5(189):189ra76. doi: 10.1126/scitranslmed.3005708.
De La Fuente et al., Novel hyaluronic acid-chitosan nanoparticles for ocular gene therapy. Invest Ophthalmol Vis Sci. May 2008;49(5):2016-24. doi: 10.1167/iovs.07-1077.
Devoldere et al., The obstacle course to the inner retina: Hyaluronic acid-coated lipoplexes cross the vitreous but fail to overcome the inner limiting membrane. Eur J Pharm Biopharm. Aug. 2019;141:161-171. doi: 10.1016/j.ejpb.2019.05.023. Epub May 28, 2019.
Doroudchi et al., Virally delivered channelrhodopsin-2 safely and effectively restores visual function in multiple mouse models of blindness. Mol Ther. Jul. 2011;19(7): 1220-9. doi: 10.1038/mt.2011.69. Epub Apr. 19, 2011.
Grimm et al., In vitro and in vivo gene therapy vector evolution via multispecies interbreeding and retargeting of adeno-associated viruses. J Virol. Jun. 2008;82(12):5887-911. doi: 10.1128/JVI.00254-08. Epub Apr. 9, 2008.
Katada et al., Evaluation of AAV-DJ vector for retinal gene therapy. PeerJ. Jan. 17, 2019;7:e6317. doi: 10.7717/peerj.6317.
Klapper et al., Biophysical Properties of Optogenetic Tools and Their Application for Vision Restoration Approaches. Front Syst Neurosci. Sep. 2, 2016;10:74. doi: 10.3389/fnsys.2016.00074.
Klimczak et al., A novel adeno-associated viral variant for efficient and selective intravitreal transduction of rat Muller cells. PLoS One. Oct. 14, 2009;4(10):e7467. doi: 10.1371/journal.pone.0007467.

(Continued)

*Primary Examiner* — Ali Soroush
(74) *Attorney, Agent, or Firm* — Wolf, Greenfield & Sacks, P.C.

(57) ABSTRACT

Disclosed herein are compositions of rAAV particles and methods for administrating rAAV particles having enhanced transduction properties.

18 Claims, 25 Drawing Sheets

Specification includes a Sequence Listing.

(56) References Cited

OTHER PUBLICATIONS

Reid et al., Improvement of Photoreceptor Targeting via Intravitreal Delivery in Mouse and Human Retina Using Combinatory rAAV2 Capsid Mutant Vectors. Invest Ophthalmol Vis Sci. Dec. 1, 2017;58(14):6429-6439. doi: 10.1167/iovs.17-22281.
Shibata et al., Hyaluronic acid enhances gene delivery into the cochlea. Hum Gene Ther. Mar. 2012;23(3):302-10. doi: 10.1089/hum.2011.086. Epub Feb. 8, 2012.
Xie et al., Structure-function analysis of receptor-binding in adeno-associated virus serotype 6 (AAV-6). Virology. Nov. 10, 2011;420(1):10-9. doi: 10.1016/j.virol.2011.08.011. Epub Sep. 13, 2011.
International Preliminary Report on Patentability for Application No. PCT/US2020/040004, dated Jan. 6, 2022.
Berry et al., Restoration of high-sensitivity and adapting vision with a cone opsin. Nat Commun. Mar. 15, 2019;10(1):1221. doi: 10.1038/s41467-019-09124-x.
Extended European Search Report for Application No. 20830652.2, dated May 30, 2023.

\* cited by examiner

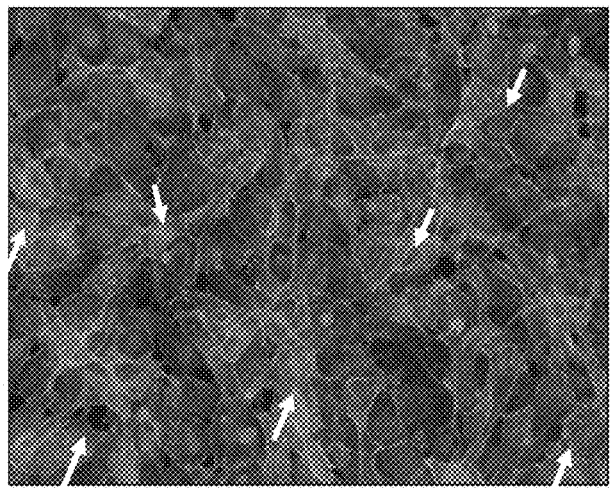
Fig. 4A
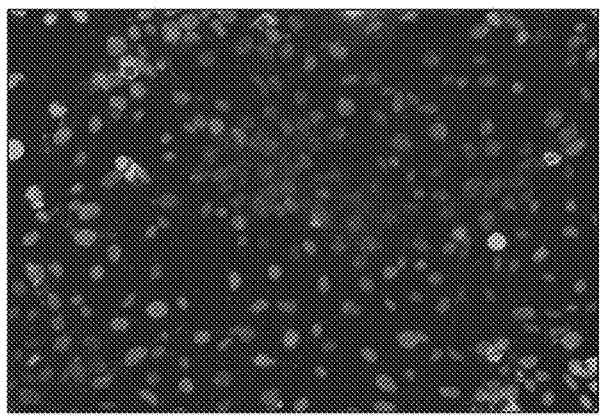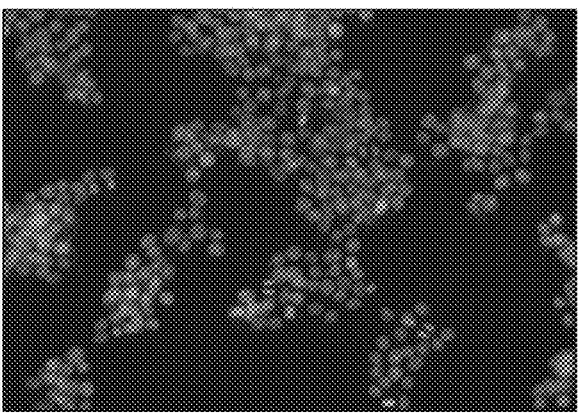
Fig. 4B		Fig. 4C

P2-V3 (4 Weeks PI)

Virus Only　　　　　　　　Hyaluronic Acid

Mouse 504

Mouse 878

ME-B(Y-F+T-V) (2 Weeks PI)

Virus Only / Hyaluronic Acid

Mouse 879

Mouse 880

Mouse 881

Fig. 10A

DGE-DF

P2-V2

P2-V3

SEQUENCE LISTING

<160> NUMBER OF SEQ ID NOS: 10

<210> SEQ ID NO 1
<211> LENGTH: 728
<212> TYPE: PRT
<213> ORGANISM: Adeno-associated virus serotype 1

<400> SEQUENCE: 1

```
Ala Ala Asp Gly Tyr Leu Pro Asp Trp Leu Glu Asp Asn Leu Ser Glu
1               5                   10                  15

Gly Ile Arg Glu Trp Trp Asp Leu Lys Pro Gly Ala Pro Lys Pro Lys
            20                  25                  30

Ala Asn Gln Gln Lys Gln Asp Asp Gly Arg Gly Leu Val Leu Pro Gly
        35                  40                  45

Tyr Lys Tyr Leu Gly Pro Phe Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Arg Tyr Asn His Ala Asp
                85                  90                  95

Ala Glu Phe Glu Arg Leu Gln Glu Asp Thr Ser Phe Gly Gly Asn Leu
            100                 105                 110

Gly Arg Ala Val Phe Gln Ala Lys Lys Arg Val Leu Glu Pro Leu Gly
        115                 120                 125

Leu Val Glu Glu Gly Ala Lys Thr Ala Pro Gly Lys Lys Arg Pro Val
130                 135                 140

Glu Gln Ser Pro Gln Glu Pro Asp Ser Ser Gly Ile Gly Lys Thr
145                 150                 155                 160

Gly Gln Gln Pro Ala Lys Lys Arg Leu Asn Phe Gly Gln Thr Gly Asp
                165                 170                 175

Ser Glu Ser Val Pro Asp Pro Gln Pro Leu Gly Glu Pro Pro Ala Thr
            180                 185                 190

Pro Ala Ala Val Gly Thr Thr Met Ala Ser Gly Gly Gly Ala Pro Met
        195                 200                 205

Ala Asp Asn Asn Glu Gly Ala Asp Gly Val Gly Asn Ala Ser Gly Asn
    210                 215                 220

Trp His Cys Asp Ser Thr Trp Leu Gly Asp Arg Val Ile Thr Thr Ser
225                 230                 235                 240

Thr Arg Thr Trp Ala Leu Pro Thr Tyr Asn Asn His Leu Tyr Lys Gln
                245                 250                 255

Ile Ser Ser Ala Ser Thr Gly Ala Ser Asn Asp Asn His Tyr Phe Gly
            260                 265                 270

Tyr Ser Thr Pro Trp Gly Tyr Phe Asp Phe Asn Arg Phe His Cys His
        275                 280                 285

Phe Ser Pro Arg Asp Trp Gln Leu Ile Asn Asn Trp Gly Phe Arg
    290                 295                 300

Pro Lys Arg Leu Asn Phe Lys Leu Phe Asn Ile Gln Val Lys Glu Val
305                 310                 315                 320

Thr Thr Asn Asp Gly Val Thr Thr Ile Ala Asn Asn Leu Thr Ser Thr
                325                 330                 335

Val Gln Val Phe Ser Asp Ser Glu Tyr Gln Leu Pro Tyr Val Leu Gly
            340                 345                 350

Ser Ala His Gln Gly Cys Leu Pro Pro Phe Pro Ala Asp Val Phe Met
        355                 360                 365
```

```
Ile Pro Gln Tyr Gly Tyr Leu Thr Leu Asn Asn Gly Ser Gln Ala Val
    370                 375                 380

Gly Arg Ser Ser Phe Tyr Cys Glu Tyr Phe Pro Ser Gln Met Leu Arg
385                 390                 395                 400

Thr Gly Asn Asn Phe Thr Phe Ser Tyr Thr Phe Glu Glu Val Pro Phe
                405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Asn Arg Thr Gln Asn Gln Ser
        435                 440                 445

Gly Ser Ala Gln Asn Lys Asp Leu Leu Phe Ser Arg Gly Ser Pro Ala
450                 455                 460

Gly Met Ser Val Gln Pro Lys Asn Trp Leu Pro Gly Pro Cys Tyr Arg
465                 470                 475                 480

Gln Gln Arg Val Ser Lys Thr Lys Thr Asn Asn Asn Ser Asn Phe Thr
                485                 490                 495

Trp Thr Gly Ala Ser Lys Tyr Asn Leu Asn Gly Arg Glu Ser Ile Ile
            500                 505                 510

Asn Pro Gly Thr Ala Met Ala Ser His Lys Asp Asp Glu Asp Lys Phe
        515                 520                 525

Phe Pro Met Ser Gly Val Met Ile Phe Gly Lys Glu Ser Ala Gly Ala
530                 535                 540

Ser Asn Thr Ala Leu Asp Asn Val Met Ile Thr Asp Glu Glu Glu Ile
545                 550                 555                 560

Lys Ala Thr Asn Pro Val Ala Thr Glu Arg Phe Gly Thr Val Ala Val
                565                 570                 575

Asn Phe Gln Ser Ser Thr Asp Pro Ala Thr Gly Asp Val His Ala Met
            580                 585                 590

Gly Ala Leu Pro Gly Met Val Trp Gln Asp Arg Asp Val Tyr Leu Gln
        595                 600                 605

Gly Pro Ile Trp Ala Lys Ile Pro His Thr Asp Gly His Phe His Pro
610                 615                 620

Ser Pro Leu Met Gly Gly Phe Gly Leu Lys Asn Pro Pro Pro Gln Ile
625                 630                 635                 640

Leu Ile Lys Asn Thr Pro Val Pro Ala Asn Pro Ala Glu Phe Ser
                645                 650                 655

Ala Thr Lys Phe Ala Ser Phe Ile Thr Gln Tyr Ser Thr Gly Gln Val
            660                 665                 670

Ser Val Glu Ile Glu Trp Glu Gln Lys Glu Asn Ser Lys Arg Trp Asn
        675                 680                 685

Pro Glu Val Gln Tyr Thr Ser Asn Tyr Ala Lys Ser Ala Asn Val Asp
690                 695                 700

Phe Thr Val Asp Asn Asn Gly Leu Tyr Thr Glu Pro Arg Pro Ile Gly
705                 710                 715                 720

Thr Arg Tyr Leu Thr Arg Pro Leu
                725

<210> SEQ ID NO 2
<211> LENGTH: 727
<212> TYPE: PRT
<213> ORGANISM: Adeno-associated virus serotype 2

<400> SEQUENCE: 2

Ala Ala Asp Gly Tyr Leu Pro Asp Trp Leu Glu Asp Thr Leu Ser Glu
1               5                   10                  15
```

```
Gly Ile Arg Gln Trp Trp Lys Leu Lys Pro Gly Pro Pro Pro Lys
            20                  25                  30
Pro Ala Glu Arg His Lys Asp Asp Ser Arg Gly Leu Val Leu Pro Gly
        35                  40                  45
Tyr Lys Tyr Leu Gly Pro Phe Asn Gly Leu Asp Lys Gly Glu Pro Val
 50                  55                  60
Asn Glu Ala Asp Ala Ala Leu Glu His Asp Lys Ala Tyr Asp Arg
 65                  70                  75                  80
Gln Leu Asp Ser Gly Asp Asn Pro Tyr Leu Lys Tyr Asn His Ala Asp
                85                  90                  95
Ala Glu Phe Glu Arg Leu Lys Glu Asp Thr Ser Phe Gly Gly Asn Leu
            100                 105                 110
Gly Arg Ala Val Phe Gln Ala Lys Lys Arg Val Leu Glu Pro Leu Gly
            115                 120                 125
Leu Val Glu Glu Pro Val Lys Thr Ala Pro Gly Lys Lys Arg Pro Val
130                 135                 140
Glu His Ser Pro Val Glu Pro Asp Ser Ser Gly Thr Gly Lys Ala
145                 150                 155                 160
Gly Gln Gln Pro Ala Arg Lys Arg Leu Asn Phe Gly Gln Thr Gly Asp
                165                 170                 175
Ala Asp Ser Val Pro Asp Pro Gln Pro Leu Gly Gln Pro Ala Ala
            180                 185                 190
Pro Ser Gly Leu Gly Asn Thr Met Ala Thr Gly Ser Gly Ala Pro Met
            195                 200                 205
Ala Asp Asn Asn Glu Gly Ala Asp Gly Val Gly Asn Ser Ser Gly Asn
            210                 215                 220
Trp His Cys Asp Ser Thr Trp Met Gly Asp Arg Val Ile Thr Thr Ser
225                 230                 235                 240
Thr Arg Thr Trp Ala Leu Pro Thr Tyr Asn Asn His Leu Tyr Lys Gln
                245                 250                 255
Ile Ser Ser Gln Ser Gly Ala Ser Asn Asp Asn His Tyr Phe Gly Tyr
            260                 265                 270
Ser Thr Pro Trp Gly Tyr Phe Asp Phe Asn Arg Phe His Cys His Phe
            275                 280                 285
Ser Pro Arg Asp Trp Gln Leu Ile Asn Asn Asn Trp Gly Phe Arg Pro
            290                 295                 300
Lys Arg Leu Asn Phe Lys Leu Phe Asn Ile Gln Val Lys Glu Val Thr
305                 310                 315                 320
Gln Asn Asp Gly Thr Thr Ile Ala Asn Asn Leu Thr Ser Thr Val
                325                 330                 335
Gln Val Phe Thr Asp Ser Glu Tyr Gln Leu Pro Tyr Val Leu Gly Ser
            340                 345                 350
Ala His Gln Gly Cys Leu Pro Pro Phe Pro Ala Asp Val Phe Met Val
            355                 360                 365
Pro Gln Tyr Gly Tyr Leu Thr Leu Asn Asn Gly Ser Gln Ala Val Gly
            370                 375                 380
Arg Ser Ser Phe Tyr Cys Glu Tyr Phe Pro Ser Gln Met Leu Arg Thr
385                 390                 395                 400
Gly Asn Asn Phe Thr Phe Ser Tyr Thr Phe Glu Asp Val Pro Phe His
                405                 410                 415
Ser Ser Tyr Ala His Ser Gln Ser Leu Asp Arg Leu Met Asn Pro Leu
            420                 425                 430
```

```
Ile Asp Gln Tyr Leu Tyr Tyr Leu Ser Arg Thr Asn Thr Pro Ser Gly
            435                 440                 445

Thr Thr Thr Gln Ser Arg Leu Gln Phe Ser Gln Ala Gly Ala Ser Asp
        450                 455                 460

Ile Arg Asp Gln Ser Arg Asn Trp Leu Pro Gly Pro Cys Tyr Arg Gln
465                 470                 475                 480

Gln Arg Val Ser Lys Thr Ser Ala Asn Asn Asn Ser Glu Tyr Ser Trp
                485                 490                 495

Thr Gly Ala Thr Lys Tyr His Leu Asn Gly Arg Asp Ser Leu Val Asn
            500                 505                 510

Pro Gly Pro Ala Met Ala Ser His Lys Asp Asp Glu Glu Lys Phe Phe
        515                 520                 525

Pro Gln Ser Gly Val Leu Ile Phe Gly Lys Gln Gly Ser Glu Lys Thr
    530                 535                 540

Asn Val Asp Ile Glu Lys Val Met Ile Thr Asp Glu Glu Ile Arg
545                 550                 555                 560

Thr Thr Asn Pro Val Ala Thr Glu Gln Tyr Gly Ser Val Ser Thr Asn
                565                 570                 575

Leu Gln Arg Asn Arg Gln Ala Ala Thr Ala Asp Val Asn Thr Gln Gly
            580                 585                 590

Val Leu Pro Gly Met Val Trp Gln Asp Arg Asp Val Tyr Leu Gln Gly
        595                 600                 605

Pro Ile Trp Ala Lys Ile Pro His Thr Asp Gly His Phe His Pro Ser
    610                 615                 620

Pro Leu Met Gly Gly Phe Gly Leu Lys His Pro Pro Pro Gln Ile Leu
625                 630                 635                 640

Ile Lys Asn Thr Pro Val Pro Ala Asn Pro Ser Thr Thr Phe Ser Ala
                645                 650                 655

Ala Lys Phe Ala Ser Phe Ile Thr Gln Tyr Ser Thr Gly Gln Val Ser
            660                 665                 670

Val Glu Ile Glu Trp Glu Gln Lys Glu Asn Ser Lys Arg Trp Asn Pro
        675                 680                 685

Glu Ile Gln Tyr Thr Ser Asn Tyr Asn Lys Ser Val Asn Val Asp Phe
    690                 695                 700

Thr Val Asp Thr Asn Gly Val Tyr Ser Glu Pro Arg Pro Ile Gly Thr
705                 710                 715                 720

Arg Tyr Leu Thr Arg Asn Leu
                725

<210> SEQ ID NO 3
<211> LENGTH: 728
<212> TYPE: PRT
<213> ORGANISM: Adeno-associated virus serotype 3

<400> SEQUENCE: 3

Ala Ala Asp Gly Tyr Leu Pro Asp Trp Leu Glu Asp Asn Leu Ser Glu
1               5                   10                  15

Gly Ile Arg Glu Trp Trp Ala Leu Lys Pro Gly Val Pro Gln Pro Lys
            20                  25                  30

Ala Asn Gln Gln His Gln Asp Asn Arg Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Glu Ala Asp Ala Ala Ala Leu Glu His Asp Lys Ala Tyr Asp Gln
65                  70                  75                  80
```

```
Gln Leu Lys Ala Gly Asp Asn Pro Tyr Leu Lys Tyr Asn His Ala Asp
                85                  90                  95

Ala Glu Phe Glu Arg Leu Gln Glu Asp Thr Ser Phe Gly Gly Asn Leu
            100                 105                 110

Gly Arg Ala Val Phe Gln Ala Lys Lys Arg Ile Leu Glu Pro Leu Gly
        115                 120                 125

Leu Val Glu Glu Ala Ala Lys Thr Ala Pro Gly Lys Lys Gly Ala Val
    130                 135                 140

Asp Gln Ser Pro Gln Glu Pro Asp Ser Ser Gly Val Gly Lys Ser
145                 150                 155                 160

Gly Lys Gln Pro Ala Arg Lys Arg Leu Asn Phe Gly Gln Thr Gly Asp
                165                 170                 175

Ser Glu Ser Val Pro Asp Pro Gln Pro Leu Gly Glu Pro Pro Ala Ala
            180                 185                 190

Pro Thr Ser Leu Gly Asn Thr Met Ala Ser Gly Gly Gly Ala Pro Met
        195                 200                 205

Ala Asp Asn Asn Glu Gly Ala Asp Gly Val Gly Asn Ser Ser Gly Asn
    210                 215                 220

Trp His Cys Asp Ser Gln Trp Leu Gly Asp Arg Val Ile Thr Thr Ser
225                 230                 235                 240

Thr Arg Thr Trp Ala Leu Pro Thr Tyr Asn Asn His Leu Tyr Lys Gln
                245                 250                 255

Ile Ser Ser Gln Ser Gly Ala Ser Asn Asp Asn His Tyr Phe Gly Tyr
            260                 265                 270

Ser Thr Pro Trp Gly Tyr Phe Asp Phe Asn Arg Phe His Cys His Phe
        275                 280                 285

Ser Pro Arg Asp Trp Gln Leu Ile Asn Asn Asn Trp Gly Phe Arg Pro
    290                 295                 300

Lys Lys Leu Ser Phe Lys Leu Phe Asn Ile Gln Val Arg Gly Val Thr
305                 310                 315                 320

Gln Asn Asp Gly Thr Thr Ile Ala Asn Asn Leu Thr Ser Thr Val
                325                 330                 335

Gln Val Phe Thr Asp Ser Glu Tyr Gln Leu Pro Tyr Val Leu Gly Ser
            340                 345                 350

Ala His Gln Gly Cys Leu Pro Pro Phe Pro Ala Asp Val Phe Met Val
        355                 360                 365

Pro Gln Tyr Gly Tyr Leu Thr Leu Asn Asn Gly Ser Gln Ala Val Gly
    370                 375                 380

Arg Ser Ser Phe Tyr Cys Glu Tyr Phe Pro Ser Gln Met Leu Arg Thr
385                 390                 395                 400

Gly Asn Asn Phe Gln Phe Ser Tyr Thr Phe Glu Asp Val Pro Phe His
                405                 410                 415

Ser Ser Tyr Ala His Ser Gln Ser Leu Asp Arg Leu Met Asn Pro Leu
            420                 425                 430

Ile Asp Gln Tyr Leu Tyr Tyr Leu Asn Arg Thr Gln Gly Thr Thr Ser
        435                 440                 445

Gly Thr Thr Asn Gln Ser Arg Leu Leu Phe Ser Gln Ala Gly Pro Gln
    450                 455                 460

Ser Met Ser Leu Gln Ala Arg Asn Trp Leu Pro Gly Pro Cys Tyr Arg
465                 470                 475                 480

Gln Gln Arg Leu Ser Lys Thr Ala Asn Asn Asn Ser Asn Phe Pro
                485                 490                 495
```

```
Trp Thr Ala Ala Ser Lys Tyr His Leu Asn Gly Arg Asp Ser Leu Val
            500                 505                 510

Asn Pro Gly Pro Ala Met Ala Ser His Lys Asp Asp Glu Glu Lys Phe
            515                 520                 525

Phe Pro Met His Gly Asn Leu Ile Phe Gly Lys Glu Gly Thr Thr Ala
            530                 535                 540

Ser Asn Ala Glu Leu Asp Asn Val Met Ile Thr Asp Glu Glu Glu Ile
545                 550                 555                 560

Arg Thr Thr Asn Pro Val Ala Thr Glu Gln Tyr Gly Thr Val Ala Asn
                565                 570                 575

Asn Leu Gln Ser Asn Thr Ala Pro Thr Thr Gly Thr Val Asn His Gln
            580                 585                 590

Gly Ala Leu Pro Gly Met Val Trp Gln Asp Arg Asp Val Tyr Leu Gln
            595                 600                 605

Gly Pro Ile Trp Ala Lys Ile Pro His Thr Asp Gly His Phe His Pro
            610                 615                 620

Ser Pro Leu Met Gly Gly Phe Gly Leu Lys His Pro Pro Pro Gln Ile
625                 630                 635                 640

Met Ile Lys Asn Thr Pro Val Pro Ala Asn Pro Pro Thr Thr Phe Ser
                645                 650                 655

Pro Ala Lys Phe Ala Ser Phe Ile Thr Gln Tyr Ser Thr Gly Gln Val
            660                 665                 670

Ser Val Glu Ile Glu Trp Glu Leu Gln Lys Glu Asn Ser Lys Arg Trp Asn
            675                 680                 685

Pro Glu Ile Gln Tyr Thr Ser Asn Tyr Asn Lys Ser Val Asn Val Asp
            690                 695                 700

Phe Thr Val Asp Thr Asn Gly Val Tyr Ser Glu Pro Arg Pro Ile Gly
705                 710                 715                 720

Thr Arg Tyr Leu Thr Arg Asn Leu
                725

<210> SEQ ID NO 4
<211> LENGTH: 727
<212> TYPE: PRT
<213> ORGANISM: Adeno-associated virus serotype 4

<400> SEQUENCE: 4

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Arg Leu Gln Gly Asp Thr Ser Phe Gly Gly Asn Leu
            100                 105                 110

Gly Arg Ala Val Phe Gln Ala Lys Lys Arg Val Leu Glu Pro Leu Gly
        115                 120                 125

Leu Val Glu Gln Ala Gly Glu Thr Ala Pro Gly Lys Lys Arg Pro Leu
    130                 135                 140
```

```
Ile Glu Ser Pro Gln Gln Pro Asp Ser Ser Thr Gly Ile Gly Lys Lys
145                 150                 155                 160

Gly Lys Gln Pro Ala Lys Lys Leu Val Phe Glu Asp Glu Thr Gly
            165                 170                 175

Ala Gly Asp Gly Pro Glu Gly Ser Thr Ser Gly Ala Met Ser Asp
        180                 185                 190

Asp Ser Met Arg Ala Ala Gly Gly Ala Ala Val Glu Gly Gly Gln
        195                 200                 205

Gly Ala Asp Gly Val Gly Asn Ala Ser Gly Asp Trp His Cys Asp Ser
210                 215                 220

Thr Trp Ser Glu Gly His Val Thr Thr Thr Ser Thr Arg Thr Trp Val
225                 230                 235                 240

Leu Pro Thr Tyr Asn Asn His Leu Tyr Lys Arg Leu Gly Glu Ser Leu
                245                 250                 255

Gln Ser Asn Thr Tyr Asn Gly Phe Ser Thr Pro Trp Gly Tyr Phe Asp
                260                 265                 270

Phe Asn Arg Phe His Cys His Phe Ser Pro Arg Asp Trp Gln Leu Ile
            275                 280                 285

Asn Asn Asn Trp Gly Met Arg Pro Lys Ala Met Arg Val Lys Ile Phe
290                 295                 300

Asn Ile Gln Val Lys Glu Val Thr Thr Ser Asn Gly Glu Thr Thr Val
305                 310                 315                 320

Ala Asn Asn Leu Thr Ser Thr Val Gln Ile Phe Ala Asp Ser Ser Tyr
                325                 330                 335

Glu Leu Pro Tyr Val Met Asp Ala Gly Gln Glu Gly Ser Leu Pro Pro
                340                 345                 350

Phe Pro Asn Asp Val Phe Met Val Pro Gln Tyr Gly Tyr Cys Gly Leu
            355                 360                 365

Val Thr Gly Asn Thr Ser Gln Gln Gln Thr Asp Arg Asn Ala Phe Tyr
370                 375                 380

Cys Glu Tyr Phe Pro Ser Gln Met Leu Arg Thr Gly Asn Asn Phe Glu
385                 390                 395                 400

Ile Thr Tyr Ser Phe Glu Lys Val Pro Phe His Ser Met Tyr Ala His
                405                 410                 415

Ser Gln Ser Leu Asp Arg Leu Met Asn Pro Leu Ile Asp Gln Tyr Leu
                420                 425                 430

Trp Gly Leu Gln Ser Thr Thr Thr Gly Thr Thr Leu Asn Ala Gly Thr
            435                 440                 445

Ala Thr Thr Asn Phe Thr Lys Leu Arg Pro Thr Asn Phe Ser Asn Phe
450                 455                 460

Lys Lys Asn Trp Leu Pro Gly Pro Ser Ile Lys Gln Gln Gly Phe Ser
465                 470                 475                 480

Lys Thr Ala Asn Asn Tyr Lys Ile Pro Ala Thr Gly Ser Asp Ser Leu
                485                 490                 495

Ile Lys Tyr Glu Thr His Ser Thr Leu Asp Gly Arg Trp Ser Ala Leu
                500                 505                 510

Thr Pro Gly Pro Pro Met Ala Thr Ala Gly Pro Ala Asp Ser Lys Phe
            515                 520                 525

Ser Asn Ser Gln Leu Ile Phe Ala Gly Pro Lys Gln Asn Gly Asn Thr
            530                 535                 540

Ala Thr Val Pro Gly Thr Leu Ile Phe Thr Ser Glu Glu Glu Leu Ala
545                 550                 555                 560
```

-continued

```
Ala Thr Asn Ala Thr Asp Thr Asp Met Trp Gly Asn Leu Pro Gly Gly
                565                 570                 575

Asp Gln Ser Ser Asn Leu Pro Thr Val Asp Arg Leu Thr Ala Leu Gly
            580                 585                 590

Ala Val Pro Gly Met Val Trp Gln Asn Arg Asp Ile Tyr Tyr Gln Gly
        595                 600                 605

Pro Ile Trp Ala Lys Ile Pro His Thr Asp Gly His Phe His Pro Ser
610                 615                 620

Pro Leu Ile Gly Gly Phe Gly Leu Lys His Pro Pro Gln Ile Phe
625                 630                 635                 640

Ile Lys Asn Thr Pro Val Pro Ala Asn Pro Ala Thr Thr Phe Ser Ser
                645                 650                 655

Thr Pro Val Asn Ser Phe Ile Thr Gln Tyr Ser Thr Gly Gln Val Ser
            660                 665                 670

Val Gln Ile Asp Trp Glu Gln Lys Glu Arg Ser Lys Arg Trp Asn Pro
        675                 680                 685

Glu Val Gln Phe Thr Ser Asn Tyr Gly Gln Gln Asn Ser Leu Leu Trp
690                 695                 700

Ala Pro Asp Ala Ala Gly Lys Tyr Thr Glu Pro Arg Ala Ile Gly Thr
705                 710                 715                 720

Arg Tyr Leu Thr His His Leu
                725

<210> SEQ ID NO 5
<211> LENGTH: 716
<212> TYPE: PRT
<213> ORGANISM: Adeno-associated virus serotype 5

<400> SEQUENCE: 5

Ser Phe Val Asp His Pro Pro Asp Trp Leu Glu Glu Val Gly Glu Gly
1               5                   10                  15

Leu Arg Glu Phe Leu Gly Leu Glu Ala Gly Pro Pro Lys Pro Lys Pro
            20                  25                  30

Asn Gln Gln His Gln Asp Gln Ala Arg Gly Leu Val Leu Pro Gly Tyr
        35                  40                  45

Asn Tyr Leu Gly Pro Gly Asn Gly Leu Asp Arg Gly Glu Pro Val Asn
    50                  55                  60

Arg Ala Asp Glu Val Ala Arg Glu His Asp Ile Ser Tyr Asn Glu Gln
65                  70                  75                  80

Leu Glu Ala Gly Asp Asn Pro Tyr Leu Lys Tyr Asn His Ala Asp Ala
                85                  90                  95

Glu Phe Glu Lys Leu Ala Asp Asp Thr Ser Phe Gly Gly Asn Leu Gly
            100                 105                 110

Lys Ala Val Phe Gln Ala Lys Lys Arg Val Leu Glu Pro Phe Gly Leu
        115                 120                 125

Val Glu Glu Gly Ala Lys Thr Ala Pro Thr Gly Lys Arg Ile Asp Asp
    130                 135                 140

His Phe Pro Lys Arg Lys Lys Ala Arg Thr Glu Glu Asp Ser Lys Pro
145                 150                 155                 160

Ser Thr Ser Ser Asp Ala Glu Ala Gly Pro Ser Gly Ser Gln Gln Leu
                165                 170                 175

Gln Ile Pro Ala Gln Pro Ala Ser Ser Leu Gly Asp Thr Met Ser Ala
            180                 185                 190

Gly Gly Gly Gly Pro Leu Gly Asp Asn Asn Gln Gly Ala Asp Gly Val
        195                 200                 205
```

-continued

```
Gly Asn Ala Ser Gly Asp Trp His Cys Asp Ser Thr Trp Met Gly Asp
    210                 215                 220
Arg Val Val Thr Lys Ser Thr Arg Thr Trp Val Leu Pro Ser Tyr Asn
225                 230                 235                 240
Asn His Gln Tyr Arg Glu Ile Lys Ser Gly Ser Val Asp Gly Ser Asn
                245                 250                 255
Ala Asn Ala Tyr Phe Gly Tyr Ser Thr Pro Trp Gly Tyr Phe Asp Phe
            260                 265                 270
Asn Arg Phe His Ser His Trp Ser Pro Arg Asp Trp Gln Leu Ile Asn
        275                 280                 285
Asn Tyr Trp Gly Phe Arg Pro Arg Ser Leu Arg Val Lys Ile Phe Asn
    290                 295                 300
Ile Gln Val Lys Glu Val Thr Val Gln Asp Ser Thr Thr Ile Ala
305                 310                 315                 320
Asn Asn Leu Thr Ser Thr Val Gln Val Phe Thr Asp Asp Tyr Gln
                325                 330                 335
Leu Pro Tyr Val Val Gly Asn Gly Thr Glu Gly Cys Leu Pro Ala Phe
            340                 345                 350
Pro Pro Gln Val Phe Thr Leu Pro Gln Tyr Gly Tyr Ala Thr Leu Asn
        355                 360                 365
Arg Asp Asn Thr Glu Asn Pro Thr Glu Arg Ser Ser Phe Phe Cys Glu
    370                 375                 380
Tyr Phe Pro Ser Lys Met Leu Arg Thr Gly Asn Asn Phe Glu Phe Thr
385                 390                 395                 400
Tyr Asn Phe Glu Glu Val Pro Phe His Ser Ser Phe Ala Pro Ser Gln
                405                 410                 415
Asn Leu Phe Lys Leu Ala Asn Pro Leu Val Asp Gln Tyr Leu Tyr Arg
            420                 425                 430
Phe Val Ser Thr Asn Asn Thr Gly Gly Val Gln Phe Asn Lys Asn Leu
        435                 440                 445
Ala Gly Arg Tyr Ala Asn Thr Tyr Lys Asn Trp Phe Pro Gly Pro Met
    450                 455                 460
Gly Arg Thr Gln Gly Trp Asn Leu Gly Ser Gly Asn Arg Ala Ser Val
465                 470                 475                 480
Ser Ala Phe Ala Thr Thr Asn Arg Met Glu Leu Glu Gly Ala Ser Tyr
                485                 490                 495
Gln Val Pro Pro Gln Pro Asn Gly Met Thr Asn Asn Leu Gln Gly Ser
            500                 505                 510
Asn Thr Tyr Ala Leu Glu Asn Thr Met Ile Phe Asn Ser Gln Pro Ala
        515                 520                 525
Asn Pro Gly Thr Thr Ala Thr Tyr Leu Glu Gly Asn Met Leu Ile Thr
    530                 535                 540
Ser Glu Ser Glu Thr Gln Pro Val Asn Arg Val Ala Tyr Asn Val Gly
545                 550                 555                 560
Gly Gln Met Ala Thr Asn Asn Gln Ser Thr Thr Ala Pro Ala Thr Gly
                565                 570                 575
Thr Tyr Asn Leu Gln Glu Ile Val Pro Gly Ser Val Trp Met Glu Arg
            580                 585                 590
Asp Val Tyr Leu Gln Gly Pro Ile Trp Ala Lys Ile Pro Glu Thr Gly
        595                 600                 605
Ala His Phe His Pro Ser Pro Ala Met Gly Gly Phe Gly Leu Lys His
    610                 615                 620
```

```
Pro Pro Pro Met Met Leu Ile Lys Asn Thr Pro Val Pro Gly Asn Ile
625                 630                 635                 640

Thr Ser Phe Ser Asp Val Pro Val Ser Ser Phe Ile Thr Gln Tyr Ser
            645                 650                 655

Thr Gly Gln Val Thr Val Glu Met Glu Trp Glu Lys Lys Glu Asn Ser
            660                 665                 670

Lys Arg Trp Asn Pro Glu Ile Gln Tyr Thr Asn Asn Tyr Asn Asp Pro
        675                 680                 685

Gln Phe Val Asp Phe Ala Pro Asp Ser Thr Gly Glu Tyr Arg Thr Thr
    690                 695                 700

Arg Pro Ile Gly Thr Arg Tyr Leu Thr Arg Pro Leu
705                 710                 715

<210> SEQ ID NO 6
<211> LENGTH: 728
<212> TYPE: PRT
<213> ORGANISM: Adeno-associated virus serotype 6

<400> SEQUENCE: 6

Ala Ala Asp Gly Tyr Leu Pro Asp Trp Leu Glu Asp Asn Leu Ser Glu
1               5                   10                  15

Gly Ile Arg Glu Trp Trp Asp Leu Lys Pro Gly Ala Pro Lys Pro Lys
            20                  25                  30

Ala Asn Gln Gln Lys Gln Asp Asp Gly Arg Gly Leu Val Leu Pro Gly
        35                  40                  45

Tyr Lys Tyr Leu Gly Pro Phe Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Arg Tyr Asn His Ala Asp
                85                  90                  95

Ala Glu Phe Glu Arg Leu Gln Glu Asp Thr Ser Phe Gly Gly Asn Leu
            100                 105                 110

Gly Arg Ala Val Phe Gln Ala Lys Lys Arg Val Leu Glu Pro Phe Gly
        115                 120                 125

Leu Val Glu Glu Gly Ala Lys Thr Ala Pro Gly Lys Lys Arg Pro Val
    130                 135                 140

Glu Gln Ser Pro Gln Glu Pro Asp Ser Ser Gly Ile Gly Lys Thr
145                 150                 155                 160

Gly Gln Gln Pro Ala Lys Lys Arg Leu Asn Phe Gly Gln Thr Gly Asp
                165                 170                 175

Ser Glu Ser Val Pro Asp Pro Gln Pro Leu Gly Glu Pro Pro Ala Thr
            180                 185                 190

Pro Ala Ala Val Gly Thr Thr Met Ala Ser Gly Gly Gly Ala Pro Met
        195                 200                 205

Ala Asp Asn Asn Glu Gly Ala Asp Gly Val Gly Asn Ala Ser Gly Asn
    210                 215                 220

Trp His Cys Asp Ser Thr Trp Leu Gly Asp Arg Val Ile Thr Thr Ser
225                 230                 235                 240

Thr Arg Thr Trp Ala Leu Pro Thr Tyr Asn Asn His Leu Tyr Lys Gln
                245                 250                 255

Ile Ser Ser Ala Ser Thr Gly Ala Ser Asn Asp Asn His Tyr Phe Gly
            260                 265                 270

Tyr Ser Thr Pro Trp Gly Tyr Phe Asp Phe Asn Arg Phe His Cys His
        275                 280                 285
```

```
Phe Ser Pro Arg Asp Trp Gln Leu Ile Asn Asn Trp Gly Phe Arg
    290                 295                 300

Pro Lys Arg Leu Asn Phe Lys Leu Phe Asn Ile Gln Val Lys Glu Val
305                 310                 315                 320

Thr Thr Asn Asp Gly Val Thr Thr Ile Ala Asn Asn Leu Thr Ser Thr
                325                 330                 335

Val Gln Val Phe Ser Asp Ser Glu Tyr Gln Leu Pro Tyr Val Leu Gly
            340                 345                 350

Ser Ala His Gln Gly Cys Leu Pro Phe Pro Ala Asp Val Phe Met
        355                 360                 365

Ile Pro Gln Tyr Gly Tyr Leu Thr Leu Asn Asn Gly Ser Gln Ala Val
370                 375                 380

Gly Arg Ser Ser Phe Tyr Cys Glu Tyr Phe Pro Ser Gln Met Leu Arg
385                 390                 395                 400

Thr Gly Asn Asn Phe Thr Phe Ser Tyr Thr Phe Glu Asp Val Pro Phe
                405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Asn Arg Thr Gln Asn Gln Ser
        435                 440                 445

Gly Ser Ala Gln Asn Lys Asp Leu Leu Phe Ser Arg Gly Ser Pro Ala
450                 455                 460

Gly Met Ser Val Gln Pro Lys Asn Trp Leu Pro Gly Pro Cys Tyr Arg
465                 470                 475                 480

Gln Gln Arg Val Ser Lys Thr Lys Thr Asn Asn Asn Ser Asn Phe Thr
                485                 490                 495

Trp Thr Gly Ala Ser Lys Tyr Asn Leu Asn Gly Arg Glu Ser Ile Ile
            500                 505                 510

Asn Pro Gly Thr Ala Met Ala Ser His Lys Asp Asp Lys Asp Lys Phe
        515                 520                 525

Phe Pro Met Ser Gly Val Met Ile Phe Gly Lys Glu Ser Ala Gly Ala
530                 535                 540

Ser Asn Thr Ala Leu Asp Asn Val Met Ile Thr Asp Glu Glu Ile
545                 550                 555                 560

Lys Ala Thr Asn Pro Val Ala Thr Glu Arg Phe Gly Thr Val Ala Val
                565                 570                 575

Asn Leu Gln Ser Ser Thr Asp Pro Ala Thr Gly Asp Val His Val Met
            580                 585                 590

Gly Ala Leu Pro Gly Met Val Trp Gln Asp Arg Asp Val Tyr Leu Gln
        595                 600                 605

Gly Pro Ile Trp Ala Lys Ile Pro His Thr Asp Gly His Phe His Pro
610                 615                 620

Ser Pro Leu Met Gly Gly Phe Gly Leu Lys His Pro Pro Pro Gln Ile
625                 630                 635                 640

Leu Ile Lys Asn Thr Pro Val Pro Ala Asn Pro Ala Glu Phe Ser
                645                 650                 655

Ala Thr Lys Phe Ala Ser Phe Ile Thr Gln Tyr Ser Thr Gly Gln Val
            660                 665                 670

Ser Val Glu Ile Glu Trp Glu Gln Lys Glu Asn Ser Lys Arg Trp Asn
        675                 680                 685

Pro Glu Val Gln Tyr Thr Ser Asn Tyr Ala Lys Ser Ala Asn Val Asp
690                 695                 700
```

```
Phe Thr Val Asp Asn Asn Gly Leu Tyr Thr Glu Pro Arg Pro Ile Gly
705                 710                 715                 720

Thr Arg Tyr Leu Thr Arg Pro Leu
                725

<210> SEQ ID NO 7
<211> LENGTH: 729
<212> TYPE: PRT
<213> ORGANISM: Adeno-associated virus serotype 7

<400> SEQUENCE: 7

Ala Ala Asp Gly Tyr Leu Pro Asp Trp Leu Glu Asp Asn Leu Ser Glu
1               5                   10                  15

Gly Ile Arg Glu Trp Trp Asp Leu Lys Pro Gly Ala Pro Lys Pro Lys
                20                  25                  30

Ala Asn Gln Gln Lys Gln Asp Asn Gly Arg Gly Leu Val Leu Pro Gly
            35                  40                  45

Tyr Lys Tyr Leu Gly Pro Phe Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Arg Tyr Asn His Ala Asp
                85                  90                  95

Ala Glu Phe Glu Arg Leu Gln Glu Asp Thr Ser Phe Gly Gly Asn Leu
            100                 105                 110

Gly Arg Ala Val Phe Gln Ala Lys Lys Arg Val Leu Glu Pro Leu Gly
        115                 120                 125

Leu Val Glu Glu Gly Ala Lys Thr Ala Pro Ala Lys Lys Arg Pro Val
130                 135                 140

Glu Pro Ser Pro Gln Arg Ser Pro Asp Ser Ser Thr Gly Ile Gly Lys
                145                 150                 155                 160

Lys Gly Gln Gln Pro Ala Arg Lys Arg Leu Asn Phe Gly Gln Thr Gly
                165                 170                 175

Asp Ser Glu Ser Val Pro Asp Pro Gln Pro Leu Gly Glu Pro Pro Ala
            180                 185                 190

Ala Pro Ser Ser Val Gly Gly Thr Ala Ala Gly Gly Gly Ala Pro
        195                 200                 205

Met Ala Asp Asn Asn Glu Gly Ala Asp Gly Val Gly Asn Ala Ser Gly
            210                 215                 220

Asn Trp His Cys Asp Ser Thr Trp Leu Gly Asp Arg Val Ile Thr Thr
225                 230                 235                 240

Ser Thr Arg Thr Trp Ala Leu Pro Thr Tyr Asn Asn His Leu Tyr Lys
                245                 250                 255

Gln Ile Ser Ser Glu Thr Ala Gly Ser Thr Asn Asp Asn Thr Tyr Phe
            260                 265                 270

Gly Tyr Ser Thr Pro Trp Gly Tyr Phe Asp Phe Asn Arg Phe His Cys
        275                 280                 285

His Phe Ser Pro Arg Asp Trp Gln Leu Ile Asn Asn Asn Trp Gly Phe
    290                 295                 300

Arg Pro Lys Lys Leu Arg Phe Lys Leu Phe Asn Ile Gln Val Lys Glu
305                 310                 315                 320

Val Thr Thr Asn Asp Gly Val Thr Thr Ile Ala Asn Asn Leu Thr Ser
                325                 330                 335

Thr Ile Gln Val Phe Ser Asp Ser Glu Tyr Gln Leu Pro Tyr Val Leu
            340                 345                 350
```

Gly Ser Ala His Gln Gly Cys Leu Pro Pro Phe Pro Ala Asp Val Phe
            355                 360                 365

Met Ile Pro Gln Tyr Gly Tyr Leu Thr Leu Asn Asn Gly Ser Gln Ser
370                 375                 380

Val Gly Arg Ser Ser Phe Tyr Cys Glu Tyr Phe Pro Ser Gln Met Leu
385                 390                 395                 400

Arg Thr Gly Asn Asn Phe Glu Phe Ser Tyr Ser Phe Glu Asp Val Pro
                405                 410                 415

Phe His Ser Ser Tyr Ala His Ser Gln Ser Leu Asp Arg Leu Met Asn
            420                 425                 430

Pro Leu Ile Asp Gln Tyr Leu Tyr Tyr Leu Ala Arg Thr Gln Ser Asn
            435                 440                 445

Pro Gly Gly Thr Ala Gly Asn Arg Glu Leu Gln Phe Tyr Gln Gly Gly
            450                 455                 460

Pro Ser Thr Met Ala Glu Gln Ala Lys Asn Trp Leu Pro Gly Pro Cys
465                 470                 475                 480

Phe Arg Gln Gln Arg Val Ser Lys Thr Leu Asp Asn Asn Asn Ser Asn
                485                 490                 495

Phe Ala Trp Thr Gly Ala Thr Lys Tyr His Leu Asn Gly Arg Asn Ser
            500                 505                 510

Leu Val Asn Pro Gly Val Ala Met Ala Thr His Lys Asp Asp Glu Asp
            515                 520                 525

Arg Phe Phe Pro Ser Ser Gly Val Leu Ile Phe Gly Lys Thr Gly Ala
            530                 535                 540

Thr Asn Lys Thr Thr Leu Glu Asn Val Leu Met Thr Asn Glu Glu Glu
545                 550                 555                 560

Ile Arg Pro Thr Asn Pro Val Ala Thr Glu Glu Tyr Gly Ile Val Ser
                565                 570                 575

Ser Asn Leu Gln Ala Asn Thr Ala Ala Gln Thr Gln Val Val Asn Asn
            580                 585                 590

Gln Gly Ala Leu Pro Gly Met Val Trp Gln Asn Arg Asp Val Tyr Leu
            595                 600                 605

Gln Gly Pro Ile Trp Ala Lys Ile Pro His Thr Asp Gly Asn Phe His
            610                 615                 620

Pro Ser Pro Leu Met Gly Gly Phe Gly Leu Lys His Pro Pro Pro Gln
625                 630                 635                 640

Ile Leu Ile Lys Asn Thr Pro Val Pro Ala Asn Pro Pro Glu Val Phe
                645                 650                 655

Thr Pro Ala Lys Phe Ala Ser Phe Ile Thr Gln Tyr Ser Thr Gly Gln
            660                 665                 670

Val Ser Val Glu Ile Glu Trp Glu Gln Lys Glu Asn Ser Lys Arg Trp
            675                 680                 685

Asn Pro Glu Ile Gln Tyr Thr Ser Asn Phe Glu Lys Gln Thr Gly Val
            690                 695                 700

Asp Phe Ala Val Asp Ser Gln Gly Val Tyr Ser Glu Pro Arg Pro Ile
705                 710                 715                 720

Gly Thr Arg Tyr Leu Thr Arg Asn Leu
                725

<210> SEQ ID NO 8
<211> LENGTH: 730
<212> TYPE: PRT
<213> ORGANISM: Adeno-associated virus serotype 8

<400> SEQUENCE: 8

```
Ala Ala Asp Gly Tyr Leu Pro Asp Trp Leu Glu Asp Asn Leu Ser Glu
1               5                   10                  15

Gly Ile Arg Glu Trp Trp Ala Leu Lys Pro Gly Ala Pro Lys Pro Lys
            20                  25                  30

Ala Asn Gln Gln Lys Gln Asp Gly Arg Gly Leu Val Leu Pro Gly
        35                  40                  45

Tyr Lys Tyr Leu Gly Pro Phe Asn Gly Leu Asp Lys Gly Glu Pro Val
    50                  55                  60

Asn Ala Ala Asp Ala Ala Leu Glu His Asp Lys Ala Tyr Asp Gln
65                  70                  75                  80

Gln Leu Gln Ala Gly Asp Asn Pro Tyr Leu Arg Tyr Asn His Ala Asp
                85                  90                  95

Ala Glu Phe Glu Arg Leu Gln Glu Asp Thr Ser Phe Gly Gly Asn Leu
            100                 105                 110

Gly Arg Ala Val Phe Gln Ala Lys Lys Arg Val Leu Glu Pro Leu Gly
        115                 120                 125

Leu Val Glu Glu Gly Ala Lys Thr Ala Pro Gly Lys Lys Arg Pro Val
    130                 135                 140

Glu Pro Ser Pro Gln Arg Ser Pro Asp Ser Ser Thr Gly Ile Gly Lys
145                 150                 155                 160

Lys Gly Gln Gln Pro Ala Arg Lys Arg Leu Asn Phe Gly Gln Thr Gly
                165                 170                 175

Asp Ser Glu Ser Val Pro Asp Pro Gln Pro Leu Gly Glu Pro Pro Ala
            180                 185                 190

Ala Pro Ser Gly Val Gly Asn Thr Met Ala Ala Gly Gly Gly Ala Pro
        195                 200                 205

Met Ala Asp Asn Asn Glu Gly Ala Asp Gly Val Gly Ser Ser Ser Gly
    210                 215                 220

Asn Trp His Cys Asp Ser Thr Trp Leu Gly Asp Arg Val Ile Thr Thr
225                 230                 235                 240

Ser Thr Arg Thr Trp Ala Leu Pro Thr Tyr Asn Asn His Leu Tyr Lys
                245                 250                 255

Gln Ile Ser Asn Gly Thr Ser Gly Gly Ala Thr Asn Asp Asn Thr Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Leu Ile Asn Asn Asn Trp Gly
    290                 295                 300

Phe Arg Pro Lys Arg Leu Ser Phe Lys Leu Phe Asn Ile Gln Val Lys
305                 310                 315                 320

Glu Val Thr Gln Asn Glu Gly Thr Lys Thr Ile Ala Asn Asn Leu Thr
                325                 330                 335

Ser Thr Ile Gln Val Phe Thr Asp Ser Glu Tyr Gln Leu Pro Tyr Val
            340                 345                 350

Leu Gly Ser Ala His Gln Gly Cys Leu Pro Pro Phe Pro Ala Asp Val
        355                 360                 365

Phe Met Ile Pro Gln Tyr Gly Tyr Leu Thr Leu Asn Asn Gly Ser Gln
    370                 375                 380

Ala Val Gly Arg Ser Ser Phe Tyr Cys Glu Tyr Phe Pro Ser Gln Met
385                 390                 395                 400

Leu Arg Thr Gly Asn Asn Phe Gln Phe Thr Tyr Thr Phe Glu Asp Val
                405                 410                 415
```

Pro Phe His Ser Ser Tyr Ala His Ser Gln Ser Leu Asp Arg Leu Met
                420                 425                 430

Asn Pro Leu Ile Asp Gln Tyr Leu Tyr Tyr Leu Ser Arg Thr Gln Thr
            435                 440                 445

Thr Gly Gly Thr Ala Asn Thr Gln Thr Leu Gly Phe Ser Gln Gly Gly
        450                 455                 460

Pro Asn Thr Met Ala Asn Gln Ala Lys Asn Trp Leu Pro Gly Pro Cys
465                 470                 475                 480

Tyr Arg Gln Gln Arg Val Ser Thr Thr Thr Gly Asn Asn Asn Ser Asn
                485                 490                 495

Phe Ala Trp Thr Ala Gly Thr Lys Tyr His Leu Asn Gly Arg Asn Ser
            500                 505                 510

Leu Ala Asn Pro Gly Ile Ala Met Ala Thr His Lys Asp Asp Glu Glu
        515                 520                 525

Arg Phe Phe Pro Ser Asn Gly Ile Leu Ile Phe Gly Lys Gln Asn Ala
530                 535                 540

Ala Arg Asp Asn Ala Asp Tyr Ser Asp Val Met Leu Thr Ser Glu Glu
545                 550                 555                 560

Glu Ile Lys Thr Thr Asn Pro Val Ala Thr Glu Glu Tyr Gly Ile Val
                565                 570                 575

Ala Asp Asn Leu Gln Gln Asn Thr Ala Pro Gln Ile Gly Thr Val Asn
            580                 585                 590

Ser Gln Gly Ala Leu Pro Gly Met Val Trp Gln Asn Arg Asp Val Tyr
        595                 600                 605

Leu Gln Gly Pro Ile Trp Ala Lys Ile Pro His Thr Asp Gly Asn Phe
            610                 615                 620

His Pro Ser Pro Leu Met Gly Gly Phe Gly Leu Lys His Pro Pro Pro
625                 630                 635                 640

Gln Ile Leu Ile Lys Asn Thr Pro Val Pro Ala Asp Pro Pro Thr Thr
                645                 650                 655

Phe Asn Gln Ser Lys Leu Asn Ser Phe Ile Thr Gln Tyr Ser Thr Gly
            660                 665                 670

Gln Val Ser Val Glu Ile Glu Trp Glu Gln Lys Glu Asn Ser Lys Arg
        675                 680                 685

Trp Asn Pro Glu Ile Gln Tyr Thr Ser Asn Tyr Lys Ser Thr Ser
690                 695                 700

Val Asp Phe Ala Val Asn Thr Glu Gly Val Tyr Ser Glu Pro Arg Pro
705                 710                 715                 720

Ile Gly Thr Arg Tyr Leu Thr Arg Asn Leu
                725                 730

<210> SEQ ID NO 9
<211> LENGTH: 728
<212> TYPE: PRT
<213> ORGANISM: Adeno-associated virus serotype 9

<400> SEQUENCE: 9

Ala Ala Asp Gly Tyr Leu Pro Asp Trp Leu Glu Asp Asn Leu Ser Glu
1               5                   10                  15

Gly Ile Arg Glu Trp Trp Ala Leu Lys Pro Gly Ala Pro Gln Pro Lys
                20                  25                  30

Ala Asn Gln Gln His Gln Asp Asn Ala Arg Gly Leu Val Leu Pro Gly
            35                  40                  45

Tyr Lys Tyr Leu Gly Pro Gly Asn Gly Leu Asp Lys Gly Glu Pro Val

```
                50                  55                  60
Asn Ala Asp Ala Ala Ala Leu Glu His Asp Lys Ala Tyr Asp Gln
 65                  70                  75                  80

Gln Leu Lys Ala Gly Asp Asn Pro Tyr Leu Lys Tyr Asn His Ala Asp
                 85                  90                  95

Ala Glu Phe Glu Arg Leu Lys Glu Asp Thr Ser Phe Gly Gly Asn Leu
            100                 105                 110

Gly Arg Ala Val Phe Gln Ala Lys Lys Arg Leu Leu Glu Pro Leu Gly
            115                 120                 125

Leu Val Glu Glu Ala Ala Lys Thr Ala Pro Gly Lys Lys Arg Pro Val
130                 135                 140

Glu Gln Ser Pro Gln Glu Pro Asp Ser Ser Ala Gly Ile Gly Lys Ser
145                 150                 155                 160

Gly Ala Gln Pro Ala Lys Lys Arg Leu Asn Phe Gly Gln Thr Gly Asp
                165                 170                 175

Thr Glu Ser Val Pro Asp Pro Gln Pro Ile Gly Glu Pro Pro Ala Ala
            180                 185                 190

Pro Ser Gly Val Gly Leu Thr Met Ala Ser Gly Gly Ala Pro Val
            195                 200                 205

Ala Asp Asn Asn Glu Gly Ala Asp Gly Val Gly Ser Ser Ser Gly Asn
210                 215                 220

Trp His Cys Asp Ser Gln Trp Leu Gly Asp Arg Val Ile Thr Thr Ser
225                 230                 235                 240

Thr Arg Thr Trp Ala Leu Pro Thr Tyr Asn Asn His Leu Tyr Lys Gln
                245                 250                 255

Ile Ser Asn Ser Thr Ser Gly Gly Ser Ser Asn Asp Asn Ala Tyr Phe
            260                 265                 270

Gly Tyr Ser Thr Pro Trp Gly Tyr Phe Asp Phe Asn Arg Phe His Cys
            275                 280                 285

His Phe Ser Pro Arg Asp Trp Gln Leu Ile Asn Asn Asn Trp Gly Phe
            290                 295                 300

Arg Pro Lys Arg Leu Asn Phe Lys Leu Phe Asn Ile Gln Val Lys Glu
305                 310                 315                 320

Val Thr Asp Asn Asn Gly Val Lys Thr Ile Ala Asn Asn Leu Thr Ser
                325                 330                 335

Thr Val Gln Val Phe Thr Asp Ser Asp Tyr Gln Leu Pro Tyr Val Leu
            340                 345                 350

Gly Ser Ala His Glu Gly Cys Leu Pro Pro Phe Pro Ala Asp Val Phe
            355                 360                 365

Met Ile Pro Gln Tyr Gly Tyr Leu Thr Leu Asn Asp Gly Ser Gln Ala
            370                 375                 380

Val Gly Arg Ser Ser Phe Tyr Cys Glu Tyr Phe Pro Ser Gln Met Leu
385                 390                 395                 400

Arg Thr Gly Asn Asn Phe Gln Phe Ser Tyr Glu Phe Glu Asn Val Pro
                405                 410                 415

Phe His Ser Ser Tyr Ala His Ser Gln Ser Leu Asp Arg Leu Met Asn
            420                 425                 430

Pro Leu Ile Asp Gln Tyr Leu Tyr Tyr Leu Ser Lys Thr Ile Asn Gly
            435                 440                 445

Ser Gly Gln Asn Gln Gln Thr Leu Lys Phe Ser Val Ala Gly Pro Ser
            450                 455                 460

Asn Met Ala Val Gln Gly Arg Asn Tyr Ile Pro Gly Pro Ser Tyr Arg
465                 470                 475                 480
```

```
Gln Gln Arg Val Ser Thr Thr Val Thr Asn Asn Asn Ser Glu Phe Ala
                485                 490                 495

Trp Pro Gly Ala Ser Ser Trp Ala Leu Asn Gly Arg Asn Ser Leu Met
            500                 505                 510

Asn Pro Gly Pro Ala Met Ala Ser His Lys Glu Gly Glu Asp Arg Phe
        515                 520                 525

Phe Pro Leu Ser Gly Ser Leu Ile Phe Gly Lys Gln Gly Thr Gly Arg
    530                 535                 540

Asp Asn Val Asp Ala Asp Lys Val Met Ile Thr Asn Glu Glu Glu Ile
545                 550                 555                 560

Lys Thr Thr Asn Pro Val Ala Thr Glu Ser Tyr Gly Gln Val Ala Thr
                565                 570                 575

Asn His Gln Ser Gln Ala Gln Ala Gln Thr Gly Trp Val Gln Asn Gln
            580                 585                 590

Gly Ile Leu Pro Gly Met Val Trp Gln Asp Arg Asp Val Tyr Leu Gln
        595                 600                 605

Gly Pro Ile Trp Ala Lys Ile Pro His Thr Asp Gly Asn Phe His Pro
    610                 615                 620

Ser Pro Leu Met Gly Gly Phe Gly Met Lys His Pro Pro Gln Ile
625                 630                 635                 640

Leu Ile Lys Asn Thr Pro Val Pro Ala Asp Pro Pro Thr Ala Phe Asn
                645                 650                 655

Lys Asp Lys Leu Asn Ser Phe Ile Thr Gln Tyr Ser Thr Gly Gln Val
            660                 665                 670

Ser Val Glu Ile Glu Trp Glu Gln Lys Glu Asn Ser Lys Arg Trp Asn
        675                 680                 685

Pro Glu Ile Gln Tyr Thr Ser Asn Tyr Tyr Lys Ser Asn Asn Val Glu
    690                 695                 700

Phe Ala Val Asn Thr Glu Gly Val Tyr Ser Glu Pro Arg Pro Ile Gly
705                 710                 715                 720

Thr Arg Tyr Leu Thr Arg Asn Leu
                725

<210> SEQ ID NO 10
<211> LENGTH: 738
<212> TYPE: PRT
<213> ORGANISM: Adeno-associated virus serotype 10

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
```

-continued

```
                115                 120                 125
Leu Gly Leu Val Glu Glu Gly Ala Lys Thr Ala Pro Gly Lys Lys Arg
            130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
            195                 200                 205

Gly Ala Pro Met Ala Asp Asn Asn Glu Gly Ala Asp Gly Val Gly Ser
            210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
            290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
            530                 535                 540
```

```
Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu
```

ENHANCING AAV-MEDIATED TRANSDUCTION OF OCULAR TISSUES WITH HYALURONIC ACID

RELATED APPLICATIONS

This application is a continuation of U.S. application Ser. No. 16/914,230, filed Jun. 26, 2020, which claims the benefit of U.S. Provisional Application No. 62/867,596, filed on Jun. 27, 2019, which is incorporated herein by reference in its entirety.

STATEMENT REGARDING FEDERALLY SPONSORED RESEARCH

This invention was made with government support under Grant No. EY024280 awarded by the National Institutes of Health. The government has certain rights in the invention.

BACKGROUND OF THE INVENTION

Major advances in the field of gene therapy have been achieved by using viruses to deliver therapeutic genetic material. The adeno-associated virus (AAV) has attracted considerable attention as a highly effective viral vector for gene therapy due to its low immunogenicity and ability to effectively transduce non-dividing cells. AAV has been shown to infect a variety of cell and tissue types, and significant progress has been made over the last decade to adapt this viral system for use in human gene therapy. AAV treatments for ocular tissues have been the focus of much research this decade, and a handful of AAV therapies have recently been approved for use in patients by the FDA.

SUMMARY OF THE INVENTION

Described herein are methods of delivering a cargo to an eye of a subject. In some embodiments, a subject is in need thereof. In some embodiments, the method comprises administering to an eye of a subject a rAAV particle. In some embodiments, a rAAV particle comprises (a) a capsid that is admixed with hyaluronic acid (HA) and (b) a cargo. In some embodiments, a rAAV particle comprises one or both of (a) a capsid that is admixed with hyaluronic acid (HA) and (b) a cargo. In some embodiments, a cargo is delivered to an eye.

In some embodiments, the HA is in direct contact with a rAAV particle capsid. In some embodiments, a rAAV capsid is at least partially coated with HA. These methods may be used in gene therapy-based treatment of several diseases of the eye. In some embodiments, a rAAV particle is administered intravitreally. In some embodiments, capsid comprises one or more surface-exposed patches of positively-charged residues. In some embodiments, the serotype of a capsid is rAAV2, or a variant thereof. In some embodiments, the serotype of a capsid is rAAV6, or a variant thereof. In some embodiments, the method further comprises pre-incubating a capsid with HA prior to administering the rAAV particle to the eye. In some embodiments, the capsid is pre-incubated with a buffer that comprises HA. In some embodiments, a buffer comprises HA in a concentration of 0.1%, 0.2%, 0.25%, 0.3%, 0.35%, 0.4%, 0.45%, 0.5%, 0.6%, 0.75%, or 1.0% weight by volume. In some embodiments, a rAAV particle is administered to the eye of a subject in a titer of about $1\times10^{10}$ vg/ml, $5\times10^{10}$ vg/ml, $1\times10^{11}$ vg/ml, $5\times10^{11}$ vg/ml, $1\times10^{12}$ vg/ml, $2\times10^{12}$ vg/ml, $3\times10^{12}$ vg/ml, $4\times10^{12}$ vg/ml, about $5\times10^{12}$ vg/ml, about $1\times10^{13}$ vg/ml, or about $5\times10^{13}$ vg/ml. In some embodiments, a rAAV particle is administered to the eye of a subject in a titer of less than $5\times10^{11}$ vg/ml. In some embodiments, a cargo comprises a polynucleotide comprising a heterologous nucleic acid sequence. In some embodiments, a heterologous nucleic acid sequence is operably linked to a regulatory sequence that direct expression of the heterologous nucleic acid sequence in a photoreceptor cell, retinal pigment epithelium cell, retinal ganglion cell, bipolar cell, Müller glial cell or astrocyte cell. In some embodiments, a regulatory sequence is selected from the group consisting of: a woodchuck hepatitis virus post-transcription regulatory element (WPRE), a polyadenylation signal sequence, an intron/exon junctions/splicing signal and any combination thereof. In some embodiments, a heterologous nucleic acid sequence encodes a therapeutic agent. In some embodiments, a therapeutic agent is a neurotrophic factor. In some embodiments, a neurotrophic factor is selected from the group consisting of: brain derived neurotrophic factor (BDNF), nerve growth factor (NGF), neurotrophin-3, ciliary neurotrophic factor (CNTF), an ephrin, glial cell line-derived neurotrophic factors (GDNF) and a combination thereof. In some embodiments, a therapeutic agent is an optogenetic actuator. In some embodiments, a optogenetic actuator is selected from the group consisting of: a bacteriorhodopsin, a halorhodopsin, a channelrhodopsin, a microbial sensory rhodopsin, a mammalian rhodopsin, a cone opsin, a melanopsin and a combination thereof. In some embodiments, a cargo is administered to treat a disease selected from the group consisting of: retinitis pigmentosa, leber Congenital Amaurosis, age related macular degeneration (AMD), wet AMD, dry AMD, uveitis, best disease, stargardts disease, usher syndrome, geographic atrophy, diabetic retinopathy, retinoschisis, achromatopsia, choroideremia, bardet biedl syndrome, a glycogen storage disease and a combination thereof. In some embodiments, the rAAV particle comprises an AAV7m8, an AAV-DJ, an AAV2/2-MAX, an AAVSHh10, an AAVSHh10Y, an AAV3, an AAV3b, or an AAVLK03 capsid. In some embodiments, a capsid sequence is at least about 70%, 75%, 80%, 85%, 90%, 95%, 96%, 97%, 98%, 99% or 100% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10.

Described herein, in certain embodiments, is a method comprising co-administering an rAAV particle with hyaluronic acid. In some embodiments, the rAAV particle with hyaluronic acid is administered by intravitreal injection to one or both eyes of a mammal. In some embodiments, the AAV particle comprises a capsid comprising one or more surface-exposed patches of positively-charged residues. In some embodiments, the serotype of the capsid is AAV2 or a variant thereof. In some embodiments, the serotype of the capsid is AAV6 or a variant thereof. In some embodiments, the rAAV particle comprises an AAV7m8, an AAV-DJ, an AAV2/2-MAX, an AAVSHh10, an AAVSHh10Y, an AAV3, an AAV3b, or an AAVLK03 capsid. In some embodiments, the capsid of the rAAV particle is pre-incubated with hyaluronic acid (HA) prior to administration to one or both eyes of a mammal. In some embodiments, the capsid is pre-incubated with a buffer that comprises HA. In some embodiments, the capsid is pre-incubated with HA for a duration of at least about 5 minutes, about 15 minutes, about 30 minutes, about 45 minutes, about 60 minutes or about 75 minutes. In some embodiments, the capsid is pre-incubated for a duration of about 15 minutes. In some embodiments, the capsid is pre-incubated with HA in a concentration of at least about 0.1%, 0.2%, 0.25%, 0.3%, 0.35%, 0.4%, 0.45%, 0.5%, 0.6%, 0.75%, 1.0%, 1.5%, 2.5%, 3.0%, 3.5%, 4%, 5% or 10% weight by volume. In some embodiments, the rAAV particle is administered in a titer of about $1\times10^{10}$ vg/ml, $5\times10^{10}$ vg/ml, $1\times10^{11}$ vg/ml, $5\times10^{11}$ vg/ml, $1\times10^{12}$ vg/ml, $2\times10^{12}$ vg/ml, $3\times10^{12}$ vg/ml, $4\times10^{12}$ vg/ml, about $5\times10^{12}$ vg/ml, about $1\times10^{13}$ vg/ml, or about $5\times10^{13}$ vg/ml. In some embodiments, the rAAV particle is administered in a titer of less than $5\times10^{11}$ vg/ml. In some embodiments, the intravitreal injection is provided in a volume of about 200 μL, about 175 μL, about 160 μL, about 145 μL, about 130 μL, about 115 μL, about 100 μL, about 90 μL, about 80 μL, about 70 μL, about 60 μL, about 55 μL, about 50 μL, about 45 μL, about 35 μL, about 20 μL, about 10 μL, or about 5 μL. In some embodiments, the intravitreal injection is administered in a volume of about 50 μL. In some embodiments, the rAAV particle further comprises a polynucleotide comprising a heterologous nucleic acid sequence. In some embodiments, a heterologous nucleic acid sequence or protein is a cargo of the rAAV. In some embodiments, the heterologous nucleic acid sequence is operably linked to regulatory sequences which direct expression of the heterologous nucleic acid sequence in a photoreceptor cell, retinal pigment epithelium cell, retinal ganglion cell, bipolar cell, Müller glial cell or astrocyte cell. In some embodiments, the heterologous nucleic acid sequence encodes a therapeutic agent. In some embodiment, the therapeutic agent is for the treatment of a disease, condition or condition. In some embodiments, the therapeutic agent is selected from an neurotrophic factor or an optogenetic actuator. In some embodiments, the disease, disorder or condition is age-related macular degeneration (AMD), wet AMD, dry AMD, or geographic atrophy. In some embodiments, the mammal is human. In some embodiments, production of the therapeutic agent a) preserves one or more photoreceptor cells or one or more RPE cells, b) restores one or more rod- and/or cone-mediated functions, c) restores visual behavior in one or both eyes, or d) any combination thereof. In some embodiments, production of the therapeutic agent persists in the one or more photoreceptor cells or the one or more RPE cells substantially for a period of at least three months following an initial administration of the rAAV particle into the one or both eyes of the mammal. In some embodiments, production of the therapeutic agent preserves one or more retinal ganglion cells, Müller glial cells or astrocyte cells. In some embodiments, the therapeutic agent comprises a neurotrophic factor. In some embodiments, a neurotrophic factor is selected from the group consisting of: brain derived neurotrophic factor (BDNF), nerve growth factor (NGF), neurotrophin-3, ciliary neurotrophic factor (CNTF), an ephrin, glial cell line-derived neurotrophic factors (GDNF) and a combination thereof. In some embodiments, the disease, disorder or condition is retinitis pigmentosa or glaucoma. In some embodiments, production of the therapeutic agent preserves one or more retinal ganglion cells or retinal bipolar cells. In some embodiments, the therapeutic agent comprises an optogenetic actuator. In some embodiments, the optogenetic actuator is selected from a bacteriorhodopsin, a halorhodopsin, a channelrhodopsin, a microbial sensory rhodopsin, a mammalian rhodopsin, a cone opsin, a melanopsin, or a combination thereof. In some embodiment, the rAAV particle is not comprised in a chimeric viral/non-viral nanoparticle. In some embodiments, a capsid sequence is at least about 70%, 75%, 80%, 85%, 90%, 95%, 96%, 97%, 98%, 99% or 100% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10.

In some embodiments, described herein is a method for providing a mammal in need thereof with a therapeutically effective amount of a therapeutic agent. In some embodiments, the method comprises intravitreally co-administering an rAAV particle with hyaluronic acid (HA) to one or both eyes of a mammal. In some embodiments, HA is in direct association with the rAAV capsid. In some embodiments, co-administering of an rAAV particle with hyaluronic acid is for a time effective to provide the mammal with a therapeutically-effective amount of the therapeutic agent. In some embodiments, the rAAV particle comprises an AAV2 or an AAV6 capsid, or a variant thereof. In some embodiments, the rAAV particle comprises a capsid variant selected from AAV7m8, an AAV-DJ, an AAV2/2-MAX, an AAVSHh10, an AAVSHh10Y, an AAV3, an AAV3b, and an AAVLK03 capsid. In some embodiments, the therapeutic agent is a heterologous nucleic acid sequence. In some embodiments, the rAAV particle comprises a polynucleotide comprising a heterologous nucleic acid sequence. In some embodiments, the heterologous nucleic acid sequence is operably linked to regulatory sequences which direct expression of the heterologous nucleic acid sequence in a photoreceptor cell, retinal pigment epithelium cell, retinal ganglion cell, bipolar cell, Müller glial cell or astrocyte cell. In some embodiments, the heterologous nucleic acid sequence encodes the therapeutic agent. In some embodiments, the therapeutic agent is selected from an neurotrophic factor or an optogenetic actuator.

In some embodiment, the therapeutic agent is for treatment of a disease, condition or disorder. In some embodiments, the disease, disorder or condition is age-related macular degeneration (AMD), wet AMD, dry AMD, or geographic atrophy. In some embodiments, the mammal is human. In some embodiments, production of the therapeutic agent a) preserves one or more photoreceptor cells or one or more RPE cells, b) restores one or more rod- and/or cone-mediated functions, c) restores visual behavior in one or both eyes, or d) any combination thereof. In some embodiments, production of the therapeutic agent persists in the one or more photoreceptor cells or the one or more RPE cells substantially for a period of at least three months following an initial administration of the rAAV particle into the one or both eyes of the mammal. In some embodiments, production of the therapeutic agent preserves one or more retinal ganglion cells, Müller glial cells or astrocyte cells. In some embodiments, the therapeutic agent comprises a neurotrophic factor. In some embodiments, a neurotrophic factor is selected from the group consisting of: brain derived neurotrophic factor (BDNF), nerve growth factor (NGF), neurotrophin-3, ciliary neurotrophic factor (CNTF), an ephrin, glial cell line-derived neurotrophic factors (GDNF) and a combination thereof. In some embodiments, the disease, disorder or condition is retinitis pigmentosa or glaucoma. In some embodiments, production of the therapeutic agent preserves one or more retinal ganglion cells or retinal bipolar cells. In some embodiments, the therapeutic agent comprises an optogenetic actuator. In some embodiments, the optogenetic actuator is selected from a bacteriorhodopsin, a halorhodopsin, a channelrhodopsin, a microbial sensory rhodopsin, a mammalian rhodopsin, a cone opsin, a melanopsin, or a combination thereof. In some embodiment, the rAAV particle is not comprised in a chimeric viral/non-viral nanoparticle. In some embodiments, a capsid sequence is at least about 70%, 75%, 80%, 85%, 90%, 95%, 96%, 97%, 98%, 99% or 100% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10.

In some embodiments, described herein is a method for treating or ameliorating one or more symptoms of a disease, disorder or condition. In some embodiments, the method comprises intravitreally co-administering an rAAV particle with hyaluronic acid to one or both eyes of a mammal in need thereof. In some embodiments, the co-administration is for a time sufficient to treat or ameliorate one or more symptoms of a disease, disorder or condition in the mammal. In some embodiments, the rAAV particle comprises i) a polynucleotide encoding a therapeutic agent and ii) an AAV2 or an AAV6 capsid, or a variant thereof. In some embodiments, the rAAV particle comprises an AAV7m8, an AAV-DJ, an AAV2/2-MAX, an AAVSHh10, an AAVSHh10Y, an AAV3, an AAV3b, or an AAVLK03 capsid. In some embodiments, the disease, disorder or condition is age-related macular degeneration (AMD), wet AMD, dry AMD, or geographic atrophy. In some embodiments, the mammal is human. In some embodiments, production of the therapeutic agent a) preserves one or more photoreceptor cells or one or more RPE cells, b) restores one or more rod- and/or cone-mediated functions, c) restores visual behavior in one or both eyes, or d) any combination thereof. In some embodiments, production of the therapeutic agent persists in the one or more photoreceptor cells or the one or more RPE cells substantially for a period of at least three months following an initial administration of the rAAV particle into the one or both eyes of the mammal. In some embodiments, production of the therapeutic agent preserves one or more retinal ganglion cells, Müller glial cells or astrocyte cells. In some embodiments, the therapeutic agent comprises a neurotrophic factor. In some embodiments, a neurotrophic factor is selected from the group consisting of: brain derived neurotrophic factor (BDNF), nerve growth factor (NGF), neurotrophin-3, ciliary neurotrophic factor (CNTF), an ephrin, glial cell line-derived neurotrophic factors (GDNF) and a combination thereof. In some embodiments, the disease, disorder or condition is retinitis pigmentosa or glaucoma. In some embodiments, production of the therapeutic agent preserves one or more retinal ganglion cells or retinal bipolar cells. In some embodiments, the therapeutic agent comprises an optogenetic actuator. In some embodiments, the optogenetic actuator is selected from a bacteriorhodopsin, a halorhodopsin, a channelrhodopsin, a microbial sensory rhodopsin, a mammalian rhodopsin, a cone opsin, a melanopsin, or a combination thereof. In some embodiment, the rAAV particle is not comprised in a chimeric viral/non-viral nanoparticle.

In some embodiments, described herein is a method for providing a mammal in need thereof with a therapeutically effective amount of a therapeutic agent. In some embodiments the method comprises intravitreally co-administering an rAAV particle with hyaluronic acid to one or both eyes of a mammal. In some embodiments, the co-administering of an rAAV particle with hyaluronic acid to one or both eyes of a mammal is for a time effective to provide the mammal with a therapeutically-effective amount of the therapeutic agent. In some embodiments, the rAAV particle comprises an AAV7m8, an AAV-DJ, an AAV2/2-MAX, an AAVSHh10, an AAVSHh10Y, an AAV3, an AAV3b, or an AAVLK03 capsid. In some embodiments, a capsid sequence is at least about 70%, 75%, 80%, 85%, 90%, 95%, 96%, 97%, 98%, 99% or 100% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10.

In certain aspects, described herein is a method for treating or ameliorating one or more symptoms of a disease, disorder or condition. In some embodiments, a method comprises intravitreally co-administering an rAAV particle with hyaluronic acid to one or both eyes of a mammal in need thereof for a time sufficient to treat or ameliorate the one or more symptoms of the disease, disorder or condition in the mammal. In some embodiments, the rAAV particle comprises i) a polynucleotide encoding a therapeutic agent and ii) an AAV7m8, an AAV-DJ, an AAV2/2-MAX, an AAVSHh10, an AAVSHh10Y, an AAV3, an AAV3b, or an AAVLK03 capsid. In some embodiments, the capsid is selected from AAV7m8, AAV-DJ, AAV2/2-MAX, AAVSHh10, and AAVSHh10Y. In some embodiments, the capsid is selected from AAV3, AAV3b, and AAVLK03. In some embodiments, the capsid comprises non-native amino acid substitutions at amino acid residues of a wild-type AAV2 capsid as set forth in SEQ ID NO: 2. In some embodiments, the non-native amino acid substitutions comprise one or more of Y272F, Y444F, T491V, Y500F, Y700F, Y704F and Y730F. In some embodiments, the capsid comprises non-native amino acid substitutions at amino acid residues of a wild-type AAV6 capsid as set forth in SEQ ID NO: 6. In some embodiments, the non-native amino acid substitutions comprise one or more of Y445F, Y705F, Y731F, T492V and S663V. In some embodiments, the capsid comprises a non-native amino acid substitution at amino acid residue 531 of a wild-type AAV1 capsid as set forth in SEQ ID NO: 1. In some embodiments, the non-native amino acid substitution is E531K. In some embodiments, the capsid comprises AAV7BP2. In some embodiments, the capsid comprises AAV2G9. In some embodiments, the capsid comprises non-native amino acid substitutions at amino acid residues 533 and/or 733 of a wild-type AAV8 capsid as set forth in SEQ ID NO: 8. In some embodiments, the non-native amino acid substitution is E533K and/or Y733F. In some embodiments, the capsid comprises non-native amino acid substitutions of a wild-type AAV2 capsid as set forth in SEQ ID NO: 2. In some embodiments, the non-native amino acid substitutions comprise: (a) Y444F; (b) Y444F+Y500F+Y730F; (c) Y272F+Y444F+Y500F+Y730F; (d) Y444F+Y500F+Y730F+T491V; or (e) Y272F+Y444F+Y500F+Y730F+T491V, or at equivalent amino acid positions corresponding thereto in any one of the wild-type AAV1, AAV3, AAV4, AAV5, AAV7, AAV9, or AAV10 capsid proteins, as set forth, respectively, in SEQ ID NO: 1, SEQ ID NO: 3, SEQ ID NO: 4, SEQ ID NO: 5, SEQ ID NO: 7, SEQ ID NO: 9, or SEQ ID NO: 10. In some embodiments, the capsid comprises non-native amino acid substitutions of a wild-type AAV6 capsid as set forth in SEQ ID NO: 6, wherein the non-native amino acid substitutions comprise: (a) Y445F; (b) Y705F+Y731F; (c) T492V; (d) Y705F+Y731F+T492V; (e) S663V; or (f) S663V+T492V. In some embodiments, the disease, disorder or condition is age-related macular degeneration (AMD), wet AMD, dry AMD, or geographic atrophy. In some embodiments, the mammal is human. In some embodiments, production of the therapeutic agent a) preserves one or more photoreceptor cells or one or more RPE cells, b) restores one or more rod- and/or cone-mediated functions, c) restores visual behavior in one or both eyes, or d) any combination thereof. In some embodiments, production of the therapeutic agent persists in the one or more photoreceptor cells or the one or more RPE cells substantially for a period of at least three months following an initial administration of the rAAV particle into the one or both eyes of the mammal. In some embodiments, production of the therapeutic agent preserves one or more retinal ganglion cells, Müller glial cells or astrocyte cells. In some embodiments, the therapeutic agent comprises a neurotrophic factor. In some embodiments, a neurotrophic factor is selected from the group consisting of: brain derived neurotrophic factor (BDNF), nerve growth factor (NGF), neurotrophin-3, ciliary neurotrophic factor (CNTF), an ephrin, glial cell line-derived neurotrophic factors (GDNF) and a combination thereof. In some embodiments, the disease, disorder or condition is retinitis pigmentosa or glaucoma. In some embodiments, production of the therapeutic agent preserves one or more retinal ganglion cells or retinal bipolar cells. In some embodiments, the therapeutic agent comprises an optogenetic actuator.

In some embodiments, the optogenetic actuator is selected from a bacteriorhodopsin, a halorhodopsin, a channelrhodopsin, a microbial sensory rhodopsin, a mammalian rhodopsin, a cone opsin, a melanopsin, or a combination thereof. In some embodiment, the rAAV particle is not comprised in a chimeric viral/non-viral nanoparticle. In some embodiments, a capsid sequence is at least about 70%, 75%, 80%, 85%, 90%, 95%, 96%, 97%, 98%, 99% or 100% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10.

In certain embodiments, described herein is a buffer for storing a mixture of AAV and hyaluronic acid (HA). In some embodiments, the buff comprises: (a) HA in a concentration of about 0.1%, 0.2%, 0.25%, 0.3%, 0.35%, 0.4%, 0.45%, 0.5%, 0.6%, 0.75%, 1.0%, 2.0%, 3.0%, 5.0% or 10% weight by volume; (b) balanced salt solution (BSS); (c) artificial cerebrospinal fluid; and/or (d) phosphate buffered saline (PBS). In some embodiments, the buffer further comprises (e) Ringer's lactate solution; (f) TMN200 solution; (g) Polysorbate 20; and/or(h) poloxamer 188. In some embodiments, the HA is in a concentration of 0.4% weight by volume.

BRIEF DESCRIPTIONS OF THE DRAWINGS

The following drawings form part of the present specification and are included to demonstrate certain aspects of the present disclosure. The disclosure may be better understood by reference to the following description taken in conjunction with the accompanying drawings, in which like reference numerals identify like elements, and in which:

FIG. 1 is a schematic of the chemical structure of Hyaluronic Acid (HA), which is a linear concatemer of a dimer of D-glucaronic acid and N-axcetyl-D-glucosamine.

FIGS. 2A-2B illustrate the effects of the administration to 661 W murine photoreceptor cells in vitro of rAAV particles whose capsids had been pre-incubated with HA (brand name Healon®) at 5 minutes, 15 minutes, and 1 hour prior to infection. Pre-treatment with HA increases transduction of 661 W cells in AAV2 (FIG. 2A). 661W cells in AAV5 are illustrated in FIG. 2B. Capsids were preincubated with Healon® in a ratio of 3:1 (AAV:Healon®) and there after injected into cells at a multiplicity of infection (MOI) of 2000. Controls included uninfected cells and cells infected with vector alone.

FIG. 3 illustrates the effects of administration to HEK293T cells in vitro injected at MOIs of 5000 and 10,000 of self-complementary (sc) rAAV6-based particles expressing an mCherry reporter transgene operably controlled by an smCBA promoter. Where indicated, AAV6 capsid and AAV6 capsid variants were pre-incubated with HA prior to infection. Variants tested include AAV6(D532N) and AAV6-3 pmut. mCherry expression was calculated by fluorescence-activated cell sorting (FACS) by multiplying the percentage of positive cells by the mean fluorescence intensity in each sample. Error bars represent—1 standard deviation. HA pre-treatment substantially increased transduction of HEK293T cells by these particles.

FIGS. 4A-4C illustrate the results of a validation experiment in which immunohistochemistry (IHC) was evaluated against CD44 cell surface receptor in three cell lines. ARPE-19 cells (FIG. 4A), a human RPE line, exhibited CD44 expression (as indicated by arrows); whereas HEK293T (FIG. 4C) and 661 W cells (FIG. 4B) did not express CD44.

Figure 6A:
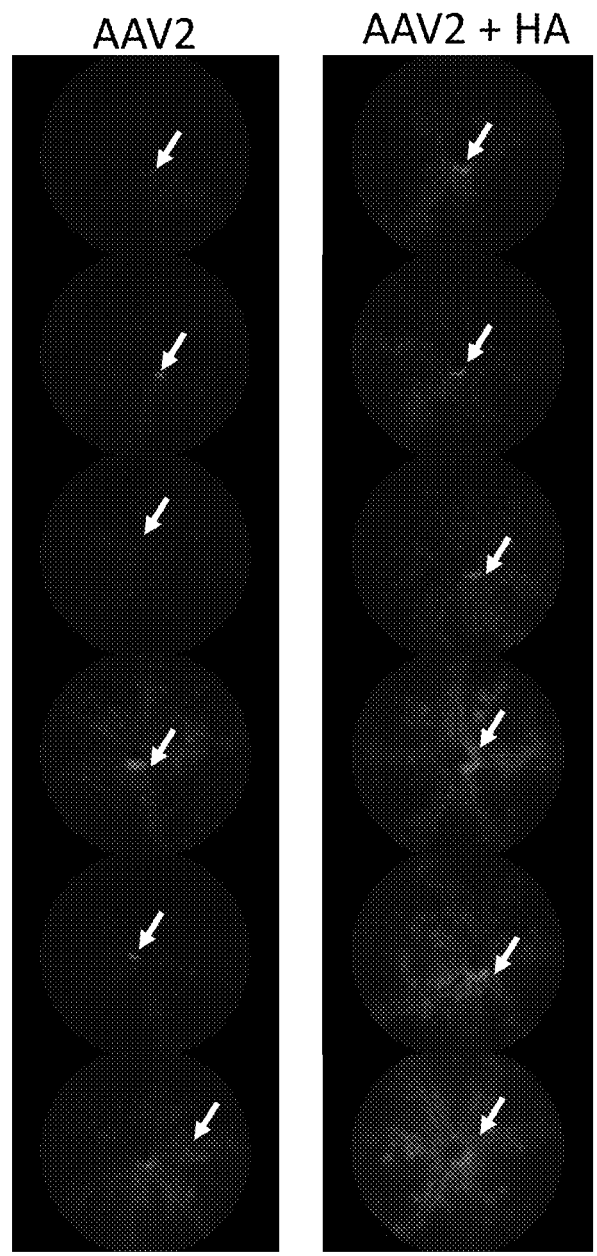
Figure 6B:
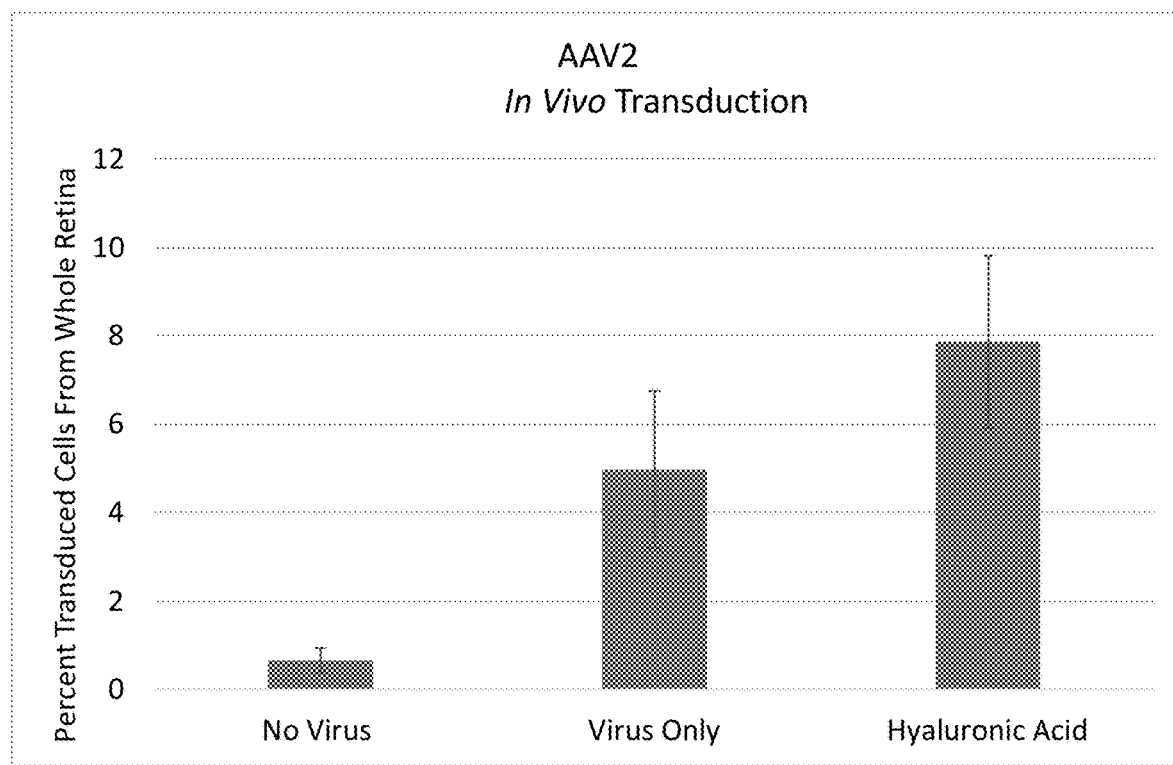

FIGS. 6A-6B illustrate the effects of HA pre-incubation and co-administration on transduction of AAV2-mediated mCherry expression after intravitreal injection of rAAV2 into whole mouse retina in vivo. Controls included uninfected cells and cells infected with vector alone. FIG. 6B represents a quantification of mCherry expression observed in FIG. 6A, as measured by flow cytometry. mCherry expression is indicated by arrows in FIG. 6A.

Figure 7A:
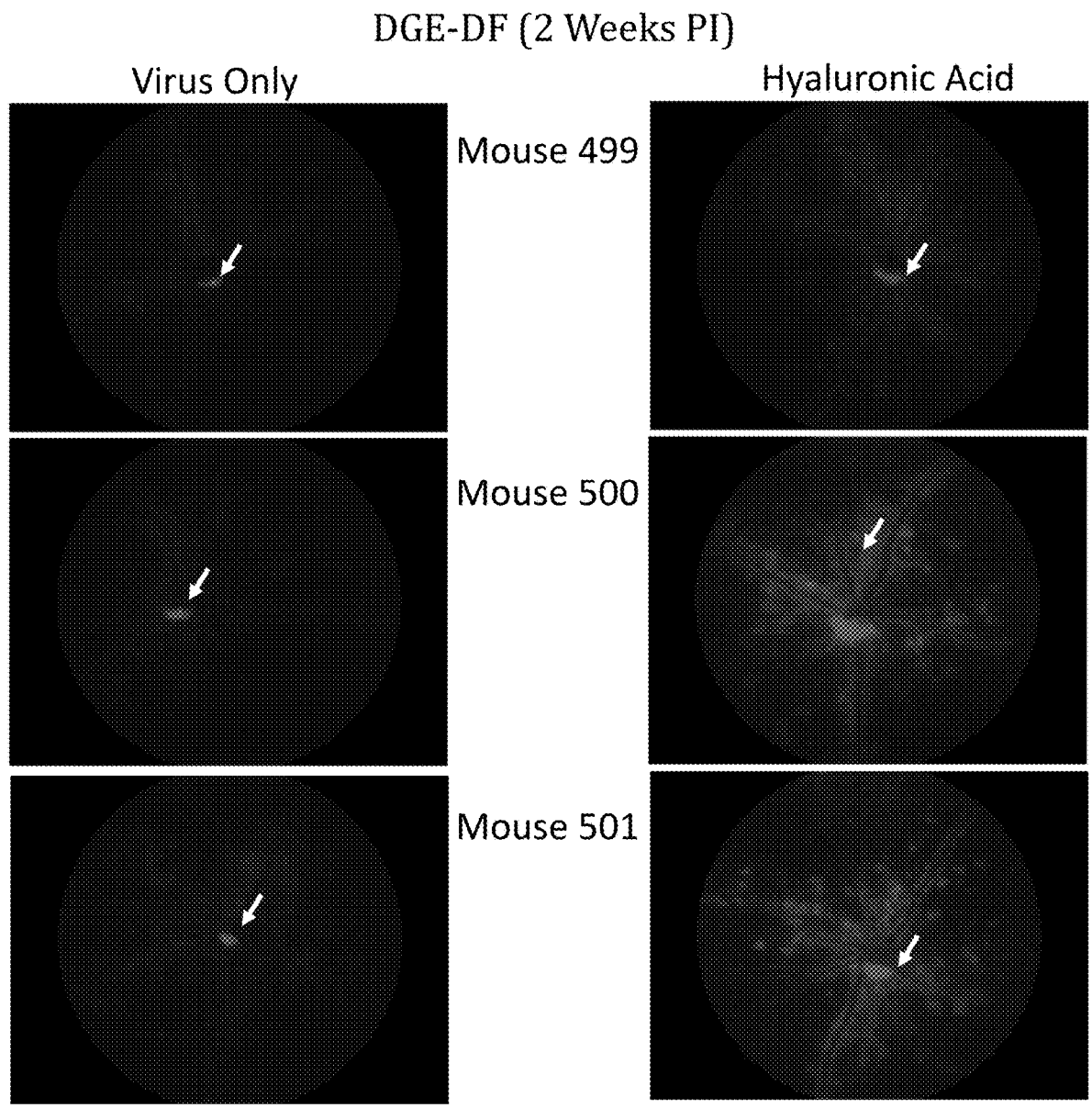
Figure 7B:
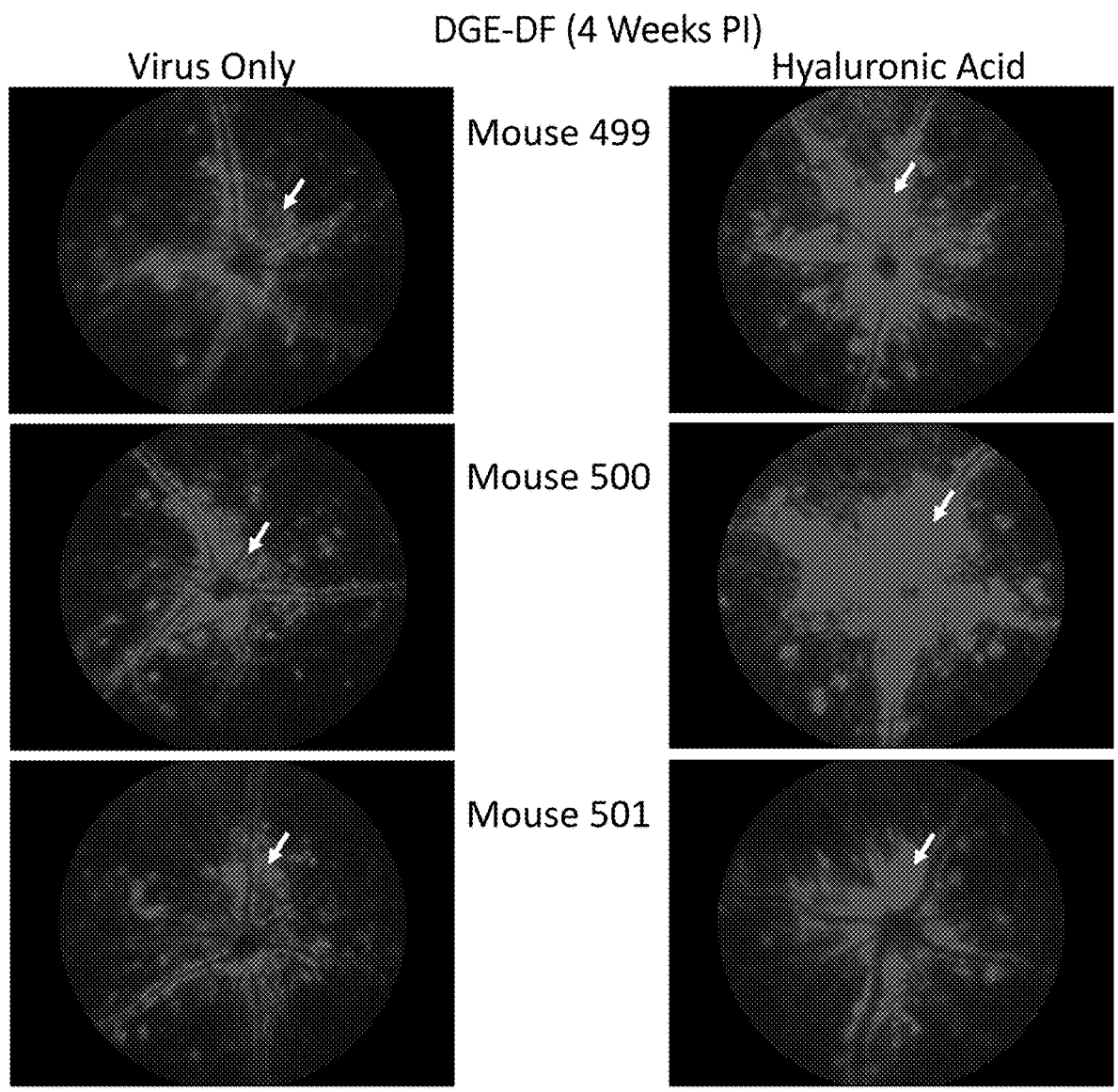
Figure 7C:
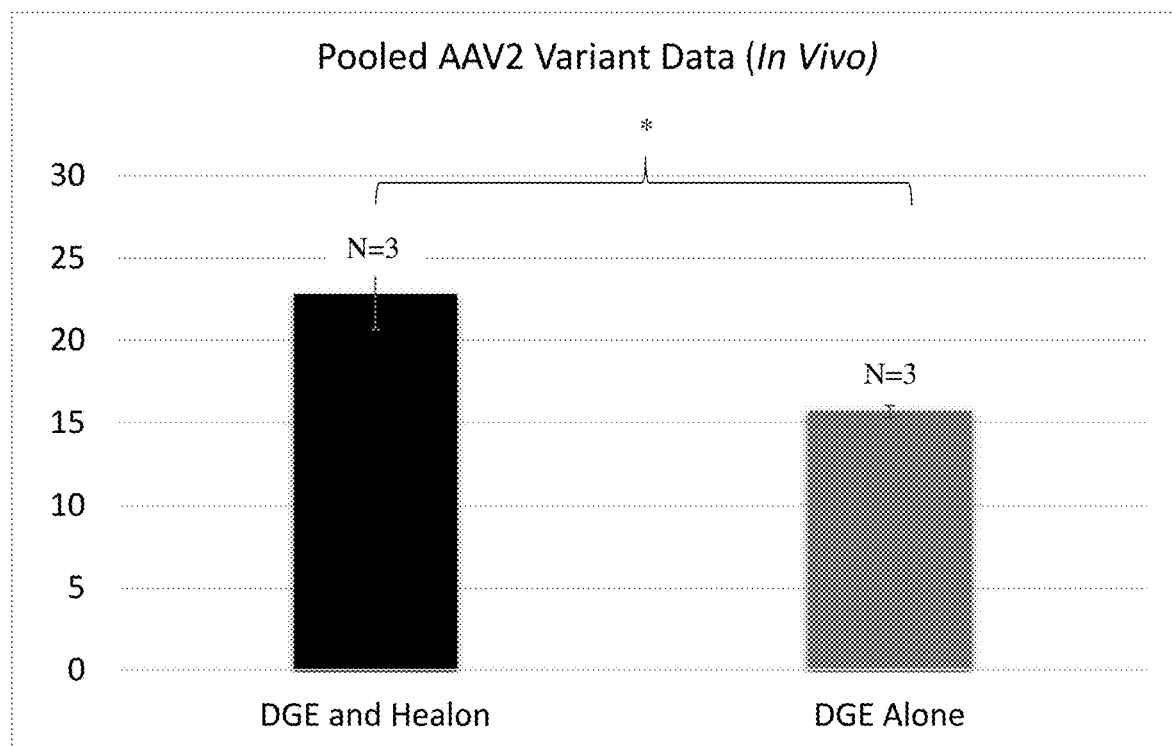
Figure 8A:
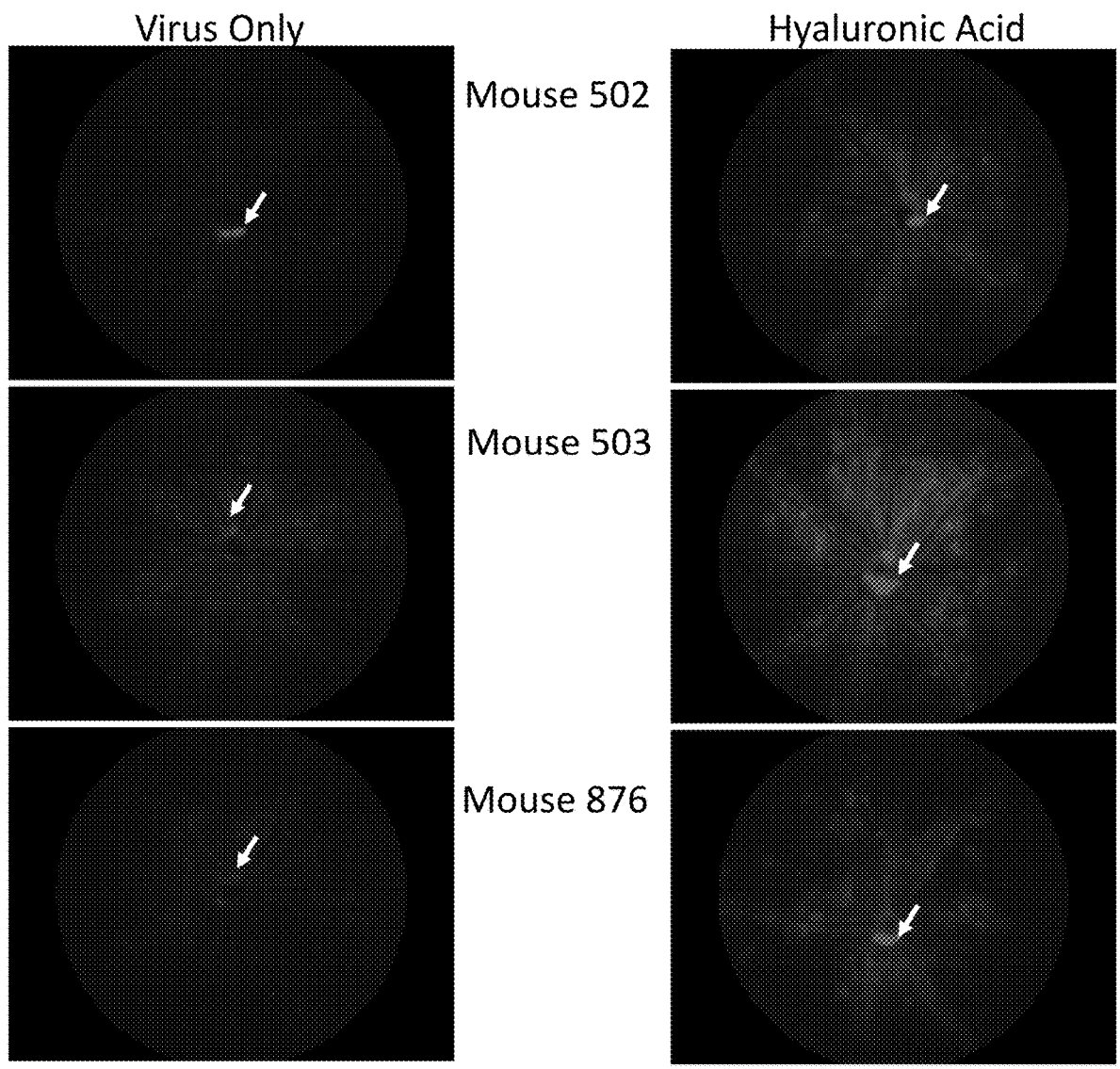
Figure 8B:
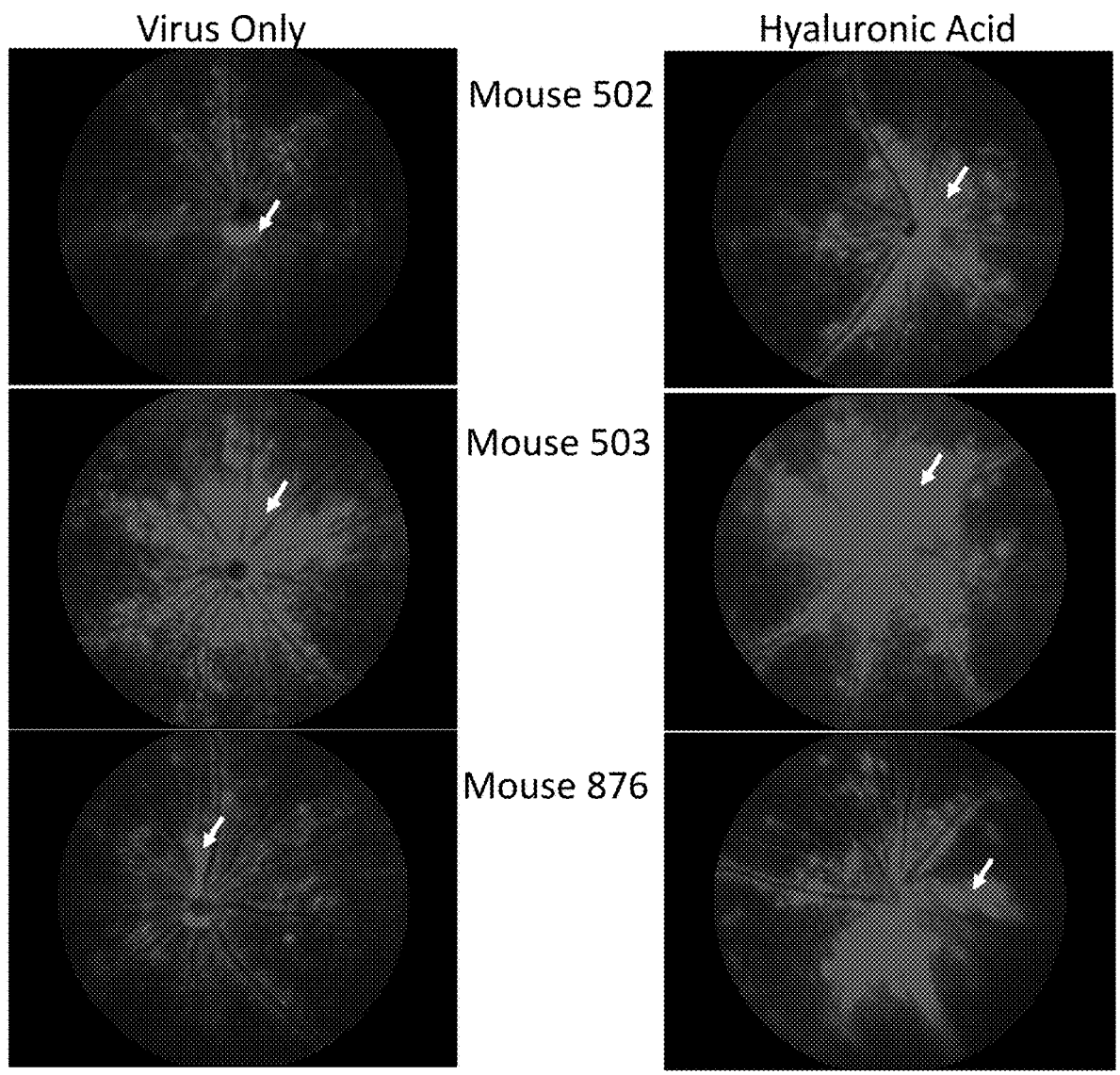
Figure 8C:
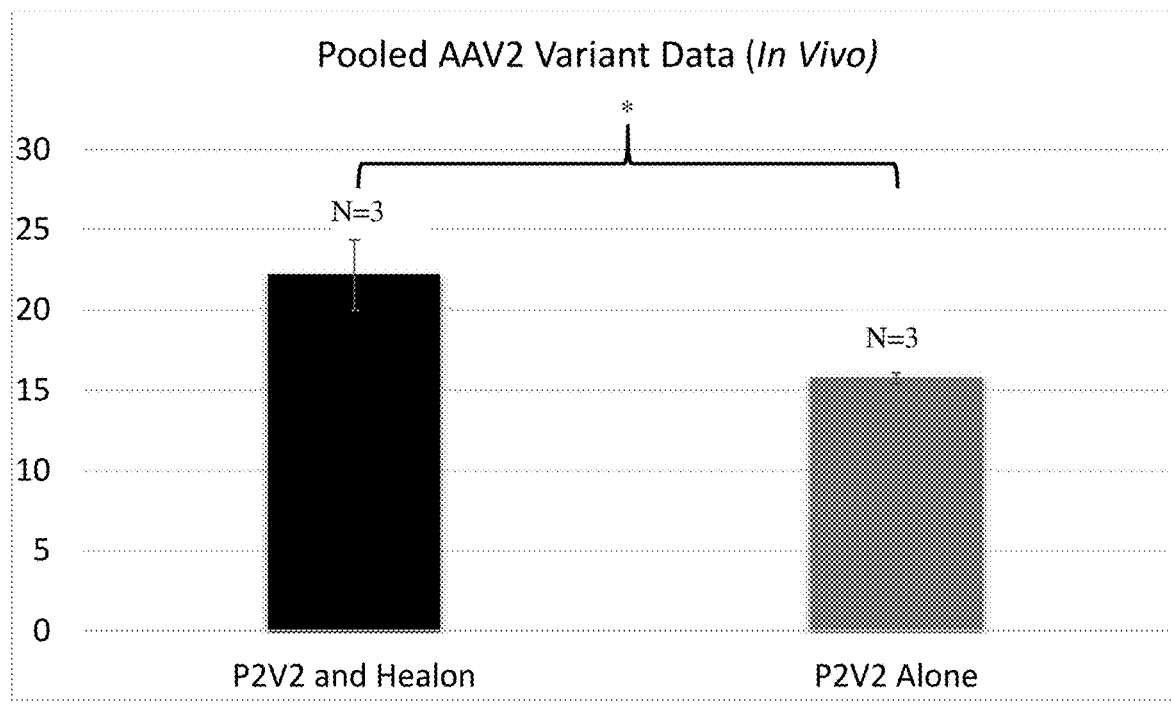

FIGS. 7A-7C illustrate the effects of intravitreal injection of rAAV particles comprising AAV2 capsid variant DGE-DF, with or without pre-treatment of the capsid with HA, into three 4-week old Nrl-GFP mice. Fundus images taken at 2 weeks (FIG. 7A) and 4 weeks (FIG. 7B) post-injection are shown. FIG. 7C represents a quantification of the mCherry expression observed in FIGS. 7A and 7B, as measured by flow cytometry data aggregated among the three mice. mCherry expression is indicated by arrows in FIGS. 7A-7B FIGS. 8A-8C illustrate the effects of intravitreal injection of rAAV particles comprising AAV2 capsid variant P2-V2, with or without pre-treatment of the capsid with HA, into three Nrl-GFP mice. Fundus images taken at 2 weeks (FIG. 8A) and 4 weeks (FIG. 8B) post-injection are shown. FIG. 8C represents a quantification of the mCherry expression observed in FIGS. 8A and 8B, as measured by flow cytometry data aggregated among the three mice. mCherry expression is indicated by arrows in FIGS. 8A-8B.

Figure 9A:
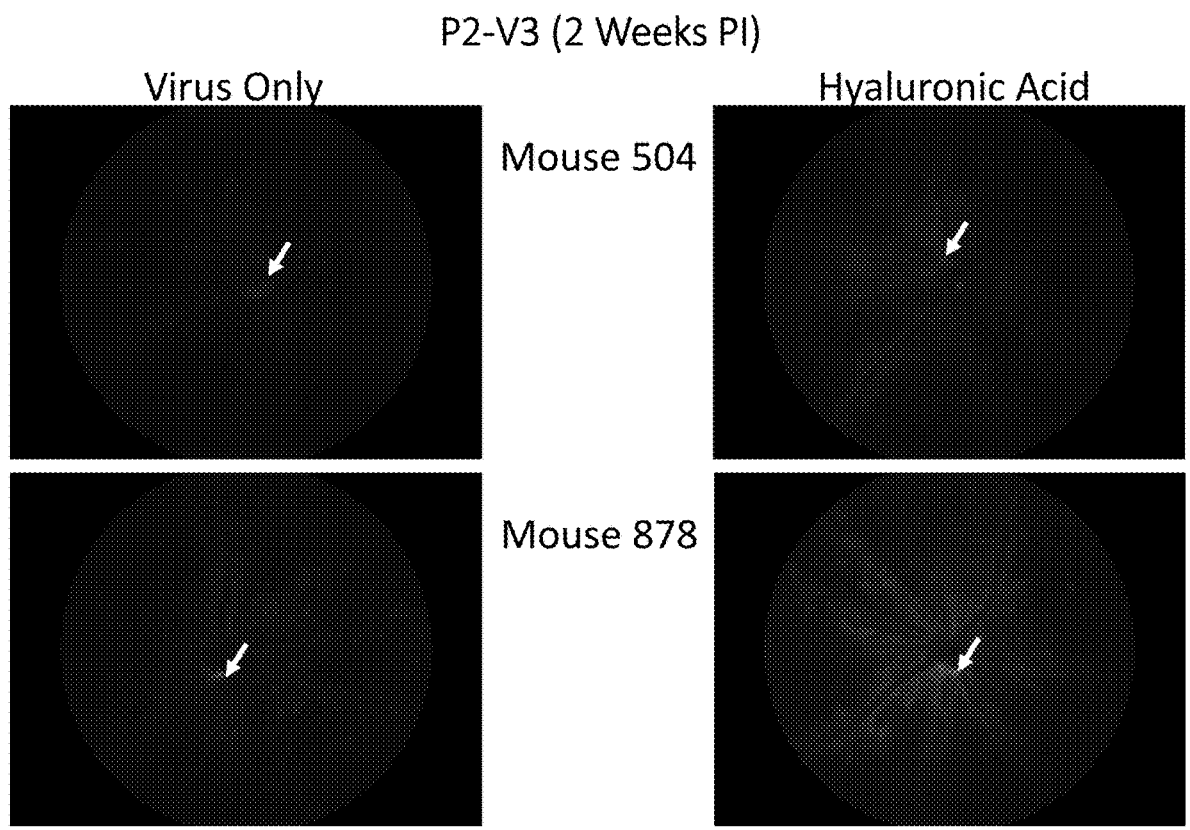
Figure 9B:
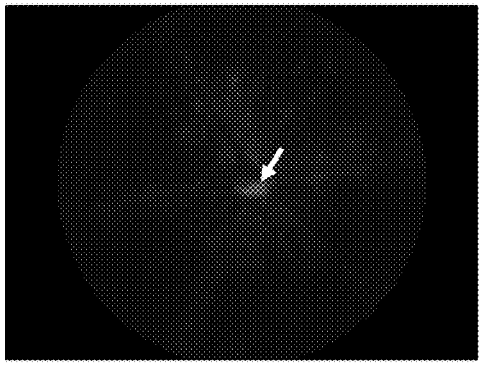
Figure 9B:
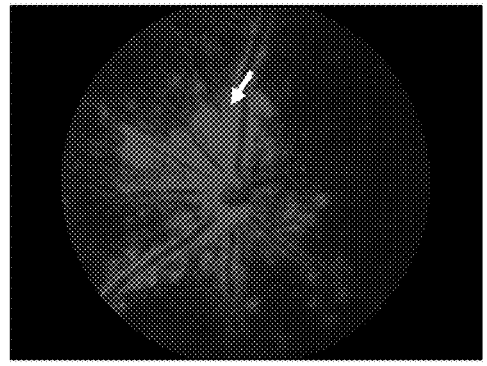
Figure 9B:
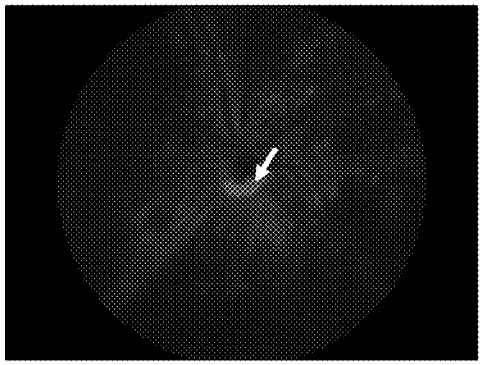
Figure 9B:
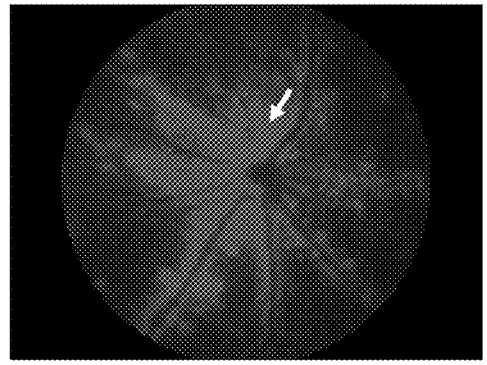
Figure 9C:
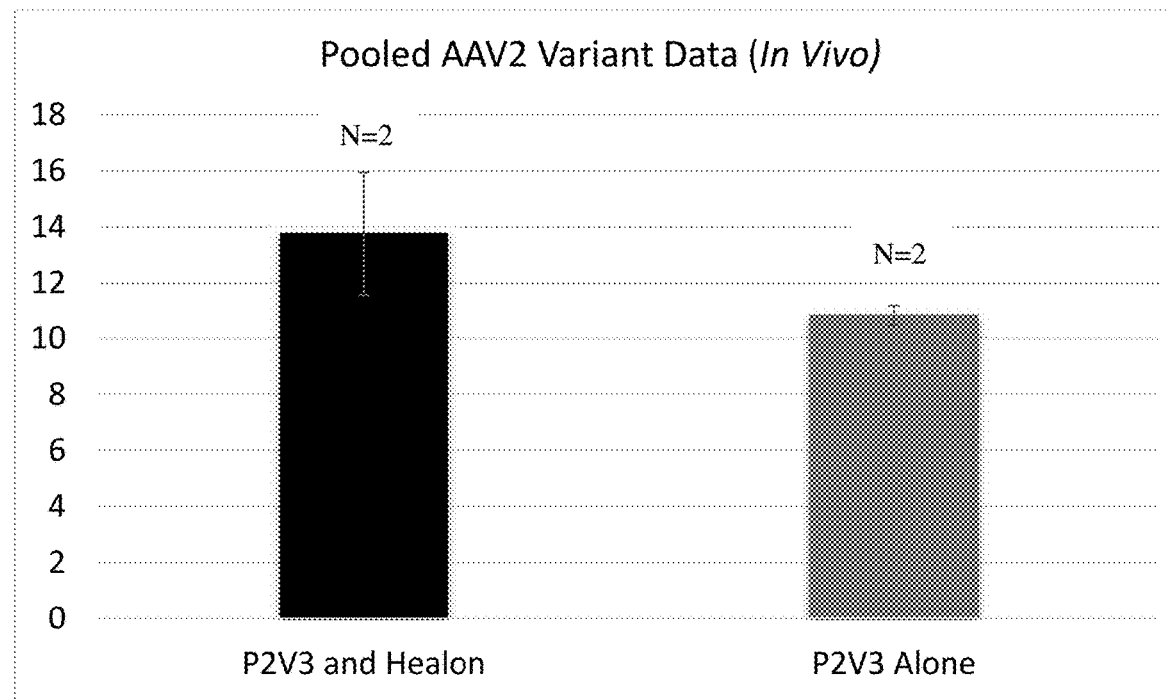

FIGS. 9A-9C illustrate the effects of intravitreal injection of rAAV particles comprising AAV2 capsid variant P2-V3, with or without pre-treatment of the capsid with HA, into Nrl-GFP mice. Fundus images taken at 2 weeks (FIG. 9A) and 4 weeks (FIG. 9B) post-injection are shown. FIG. 9C represents a quantification of the mCherry expression observed in FIGS. 9A and 9B, as measured by flow cytometry data aggregated among the two mice. mCherry expression is indicated by arrows in FIGS. 9A-9B.

Figure 10B:
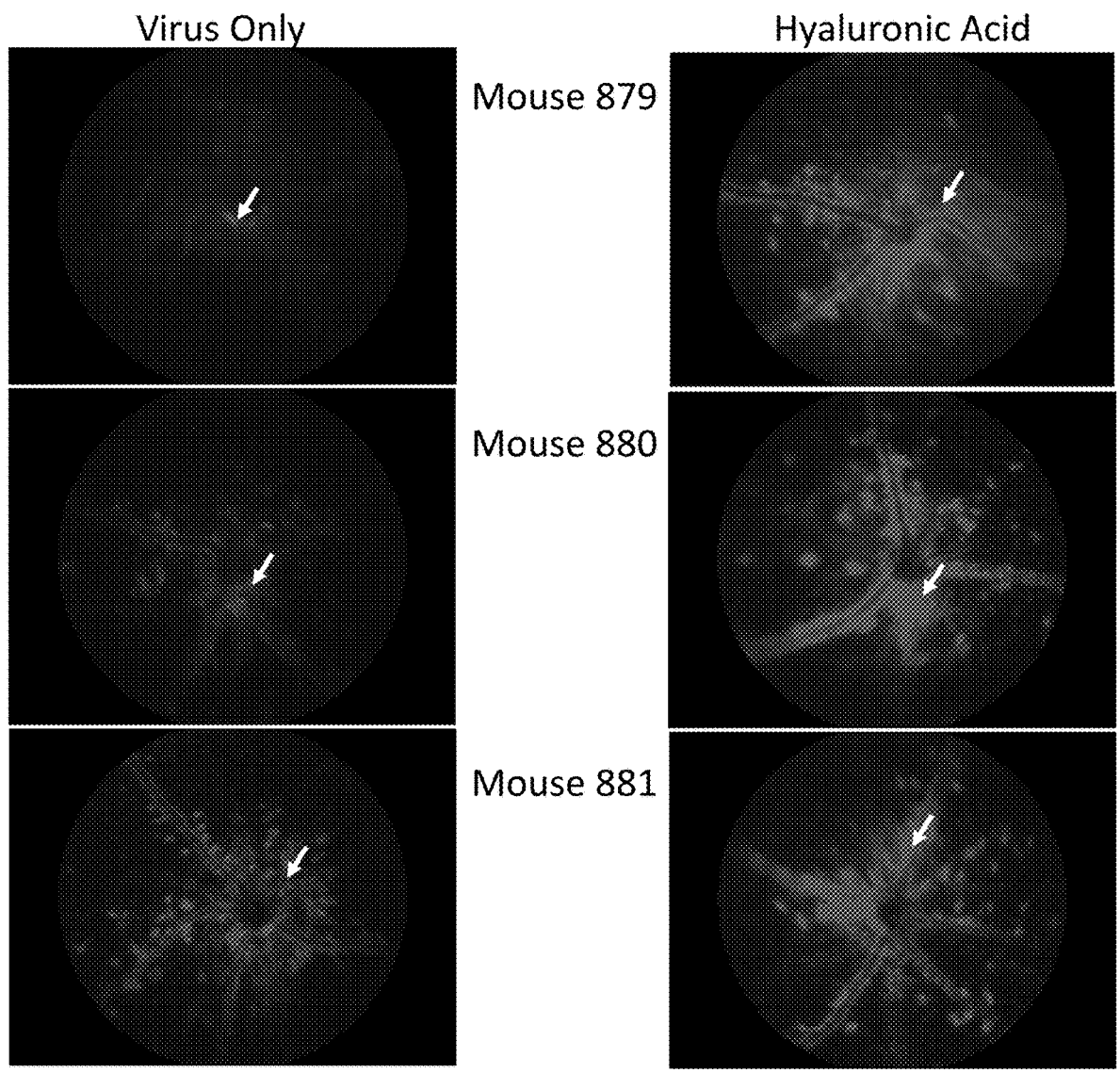
Figure 10C:
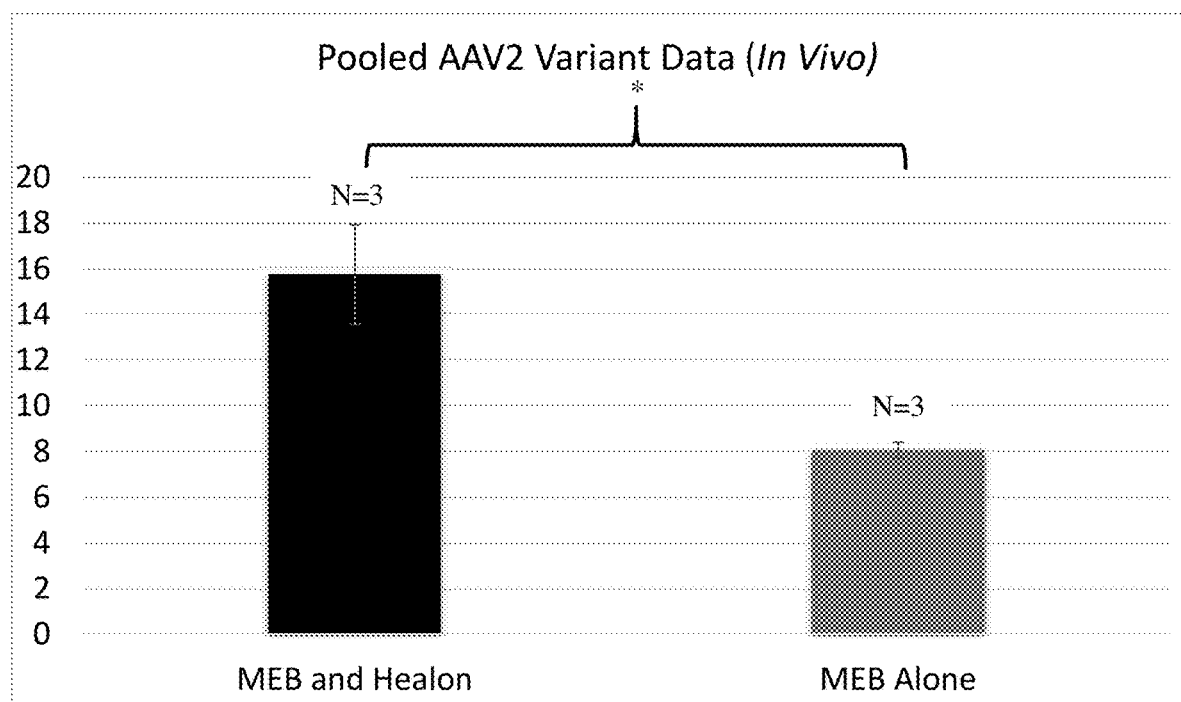

FIGS. 10A-10C illustrate the effects of intravitreal injection of rAAV particles comprising AAV2 capsid variant ME–B(Y–F+T–V), with or without pre-treatment of the capsid with HA, into three Nrl-GFP mice. Fundus images taken at 2 weeks (FIG. 10A) and 4 weeks (FIG. 10B) post-injection are shown. FIG. 10C represents a quantification of the mCherry expression observed in FIGS. 10A and 10B, as measured by flow cytometry data aggregated among the three mice. mCherry expression is indicated by arrows in FIGS. 10A-10B.

Figure 11:
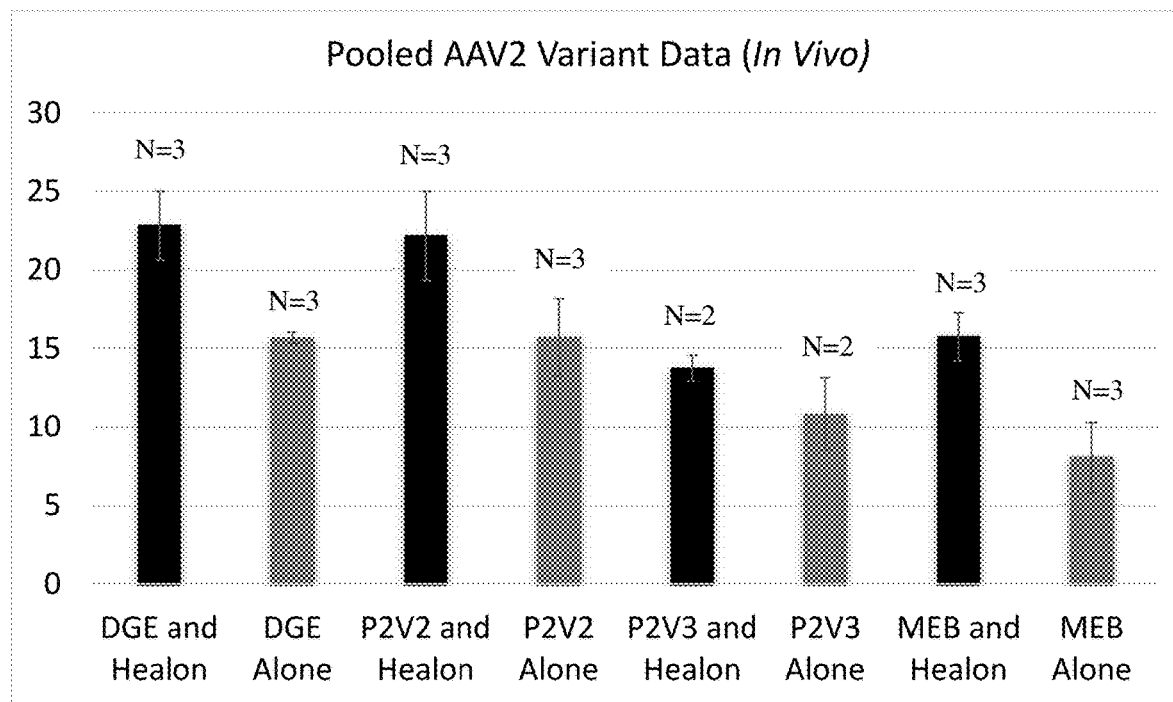

FIG. 11 is a schematic depicting the aggregated flow cytometry data for four capsids: DGE-DF, P2-V2, P2-V3, and ME-B(Y-F+T-V).

Figure 12A:
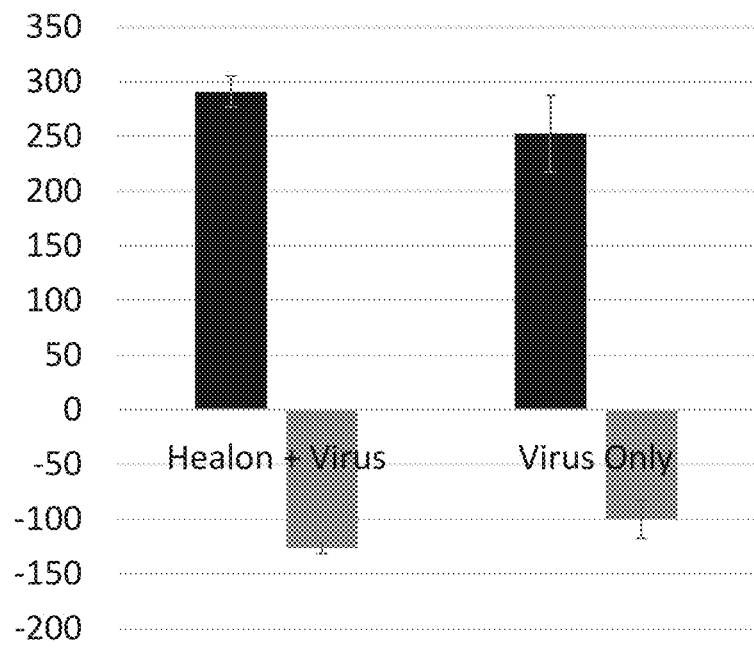
Figure 12A:
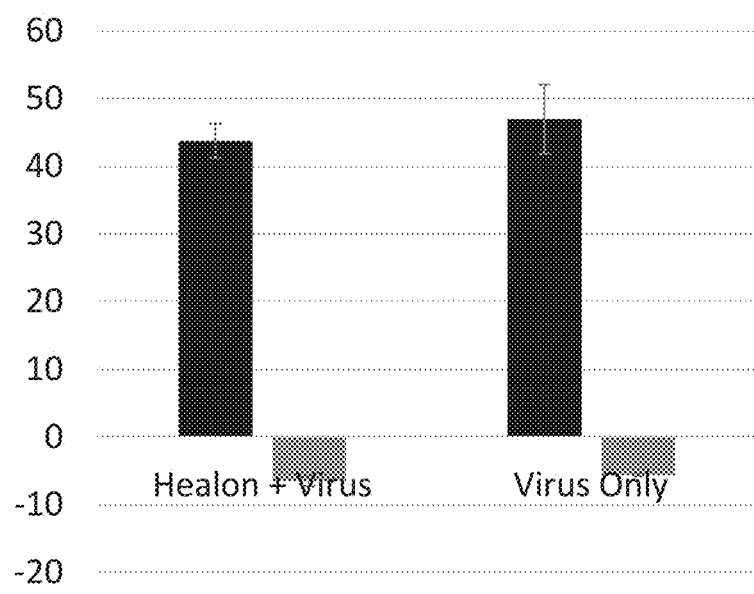
Figure 12B:
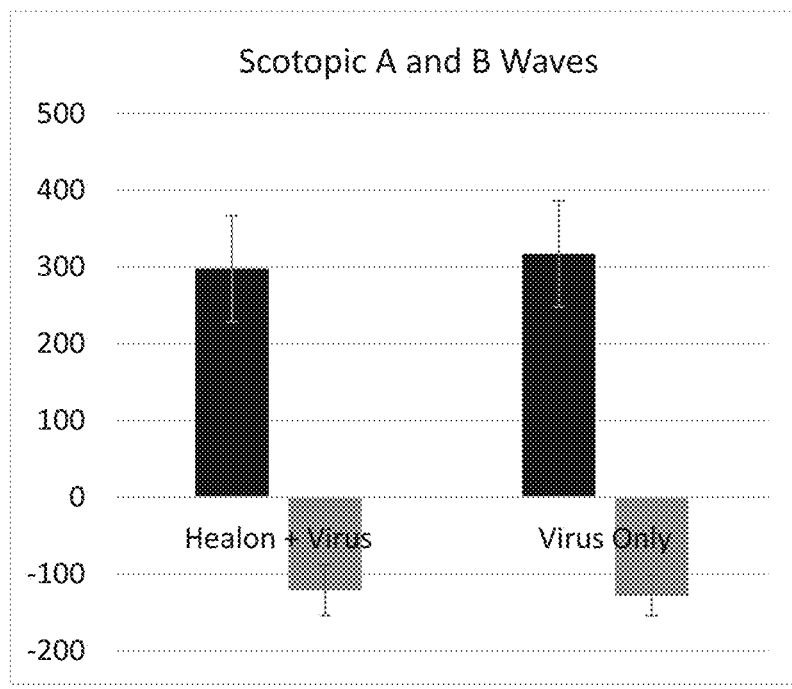
Figure 12B:
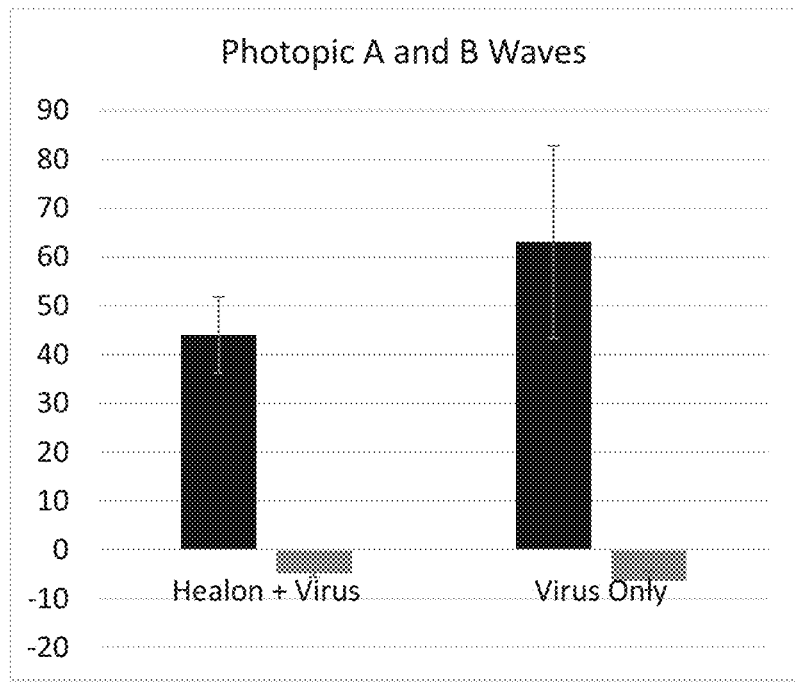
Figure 12C:
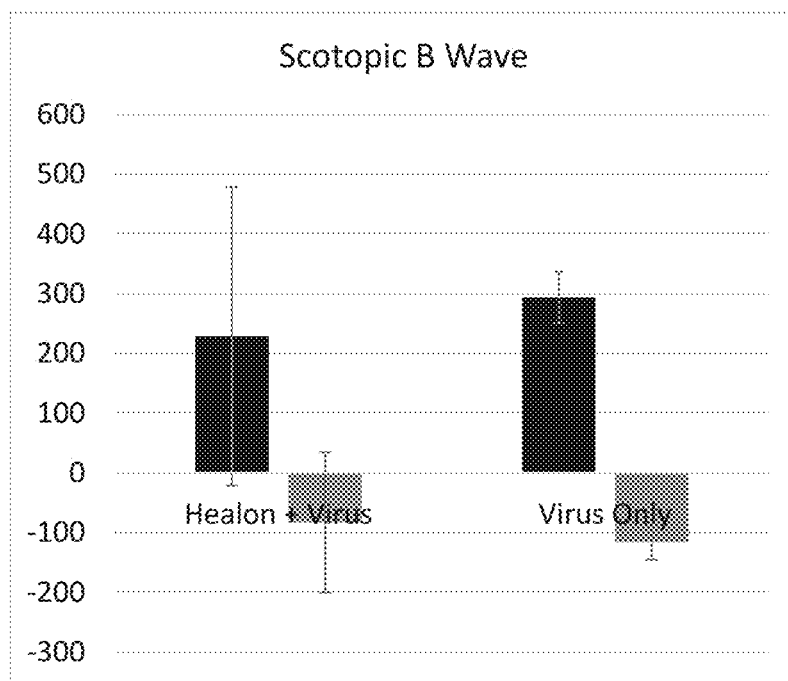
Figure 12C:
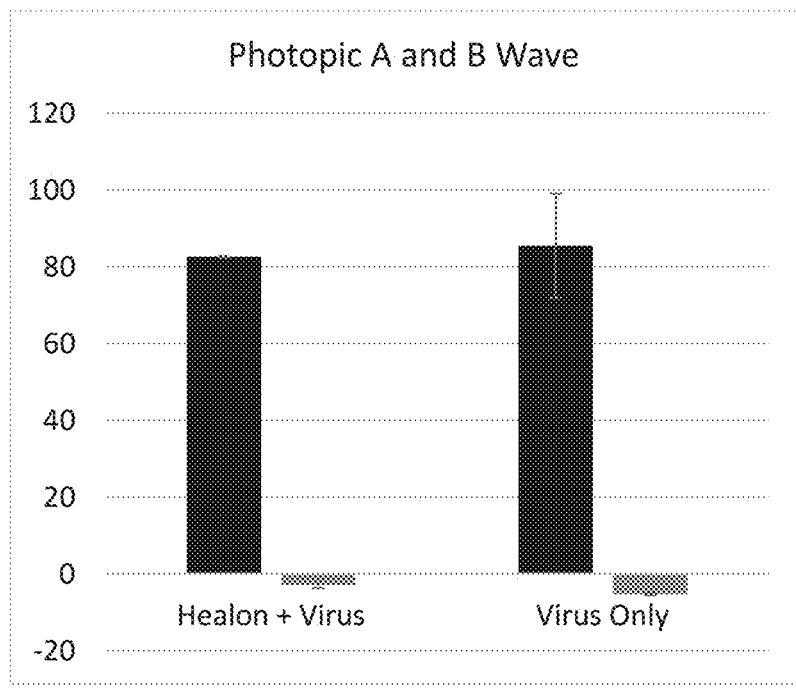
Figure 12D:
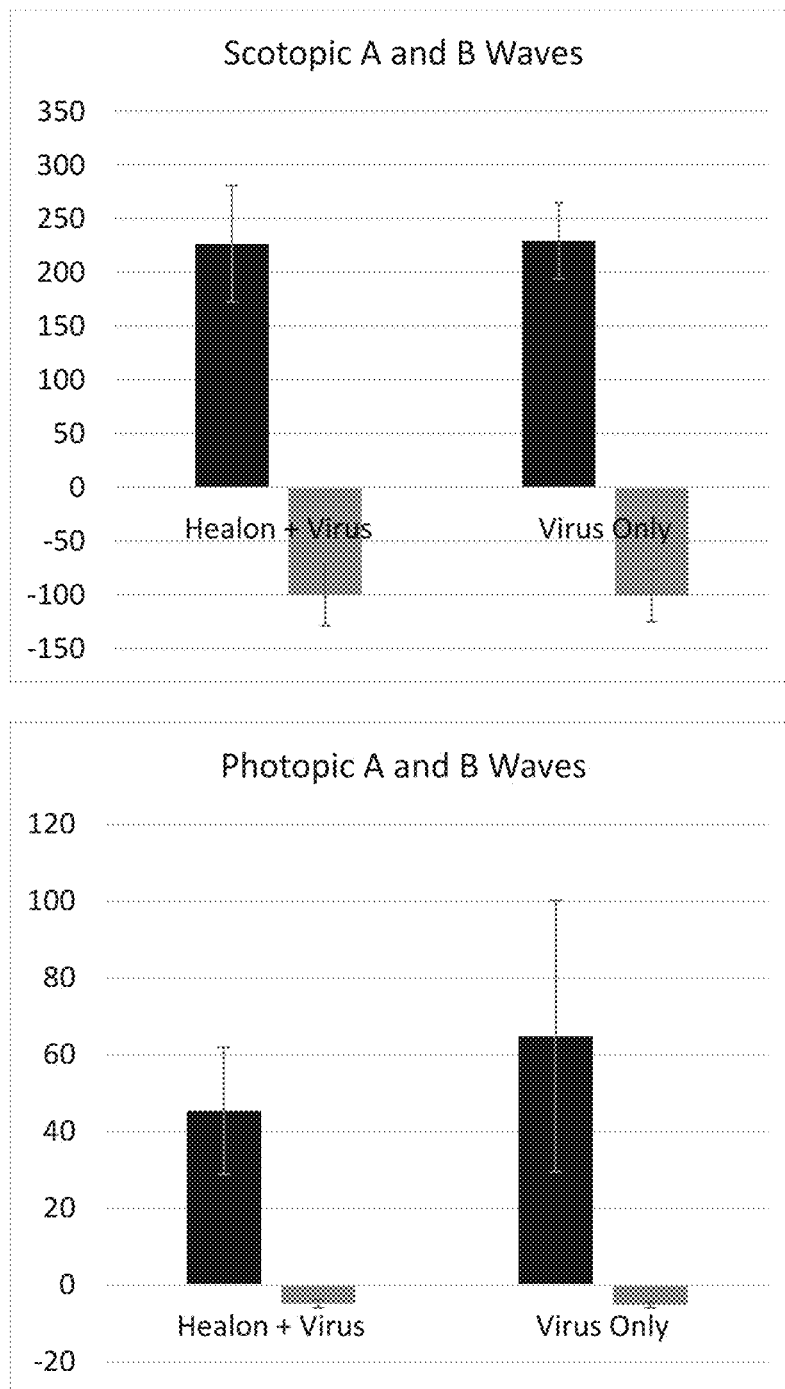
Figure 12E:
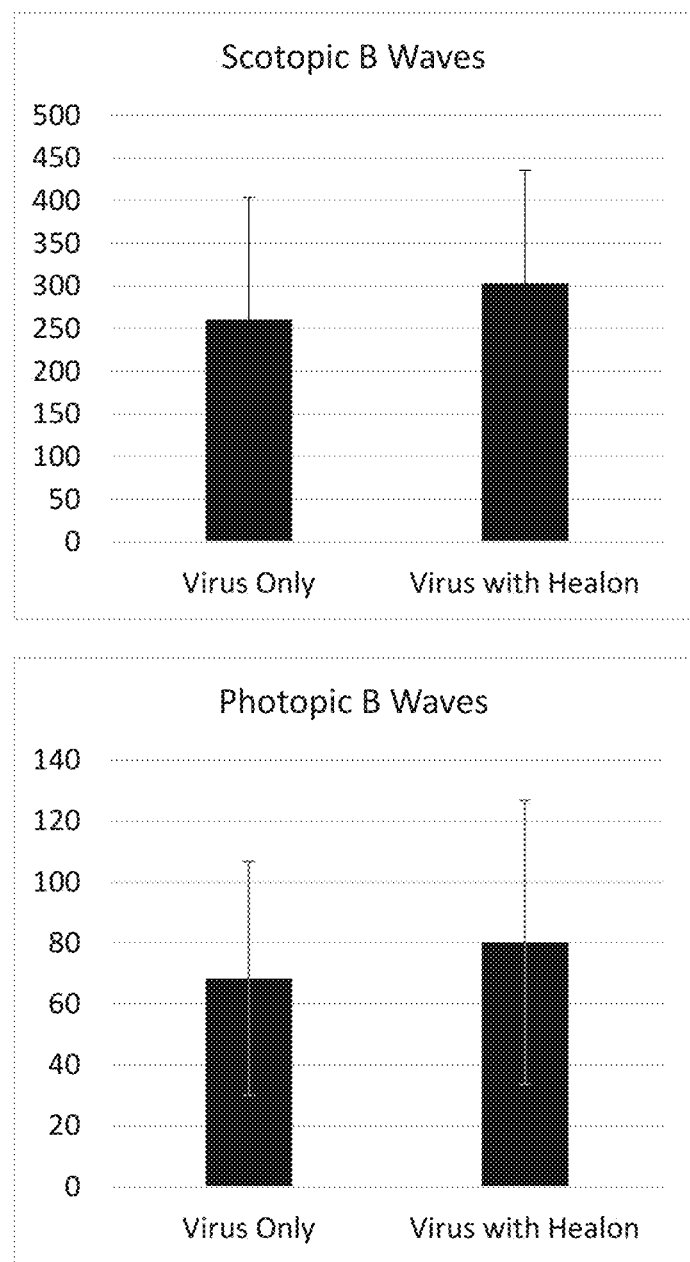

FIGS. 12A-12E are schematics showing the electroretinogram (ERG) results following intravitreal administration of HA-treated DGE-DF (FIG. 12A), P2-V2 (FIG. 12B), P2-V3 (FIG. 12C), ME-B(Y-F+T-V) (FIG. 12D) and aggregated data (FIG. 12E). Treatment and co-administration with HA had no impact on retinal cell function. In the top graph of FIG. 12E, N=11. P-value=0.478132. In the bottom graph of FIG. 12E, N=11. P-value=0.524563.

DETAILED DESCRIPTION

The present disclosure provides novel methods, compositions and buffers for administration of rAAV particles having enhanced transduction properties, comprising the pre-incubation and/or co-administration of AAV capsids and hyaluronic acid. In some embodiments, methods disclosed herein rely on treatment with a natural material that is already comprised in the mammalian eye. In some embodiments, methods disclosed herein do not rely on the modification of the capsid and function through a mechanism that does not interfere with AAV adhesion, thus fulfilling a long-felt need in the art. Advantageously, the novel methods of rAAV particle administration disclosed herein have improved efficiency in transducing the retina of the mammalian eye, and in particular, in transducing the photoreceptor (PR) and retinal pigment epithelial (RPE) cells in vivo.

Intraocular AAV therapies generally suffer from poor transduction profiles. Achieving adequate transduction of rAAV particles of the AAV2 serotype has been particularly elusive in view of the propensity of AAV2 capsids to aggregate. This aggregation is in large part due to the presence of positively-charged amino acid residues on the capsid surface. AAV6 capsids, along with several pseudotypes and variants of AAV6, AAV2 and other capsids, have similar positively-charged "patches" of residues on their surfaces that are exposed to a milieu.

Two common approaches of gene delivery into the retina are intravitreal and subretinal injections. Subretinal injections require administration into the subretinal space between the retinal pigment epithelium (RPE) and photoreceptors to transduce these neurons. To achieve delivery of the vector, a needle must penetrate the retina and, in doing so, detaches the photoreceptor cell layer from the RPE.

Intravitreal injection is less invasive, and is thus a preferred route of administration that is routinely performed for clinical human subjects. Nonetheless, few AAV serotypes have exhibited efficient transduction by intravitreal delivery. This occurs in part due to presence of the inner limiting membrane (ILM), a basement membrane between the vitreous and neural retina that is replete with heparan sulfate proteoglycans, which acts as a barrier for effective spread of the vector through the retina by sequestering capsids. with high heparan sulfate affinity. In particular, AAV2 vectors have generally failed to transduce photoreceptor cells upon administration by intravitreal injection.

Inherited retinal degenerative diseases are a clinically promising focus of AAV-mediated gene therapy. These diseases arise from pathogenic mutations in mRNA transcripts expressed in the eye's photoreceptor cells or retinal pigment epithelium (RPE), leading to cell death and structural deterioration. Prior methods designed to reduce aggregation of AAV2 and AAV6 capsids have involved pre-treatment of capsids with high-salt buffers. But these buffers are toxic to the eye, making administration after pre-treatment infeasible.

Hyaluronic acid (HA) is an anionic, non-sulfated glycosaminoglycan that is the major component of the human vitreous, where it is covalently linked to extracellular matrix. In addition, HA is an FDA-approved substance with optical and viscoelastic properties that make it a good substitute for human vitreous. HA typically enters cells through endocytosis by cell surface glycoproteins, and in particular the receptor CD44. HA can also enter the cell also by micropinocytosis.

Adenovirus transduction occurred via a mechanism dependent on CD44 which did not purport to impact the efficiency of adenovirus infectivity. Gains in transduction were primarily a function of increased transgene expression mediated by liberation of the intracellular domain of CD44 which occurred as a consequence of HA binding to CD44. However, results in adenoviral therapies cannot readily be recapitulated in recombinant AAV therapies. Further, because excipient binding to CD44 receptors may interfere with the ability of the AAV capsid to bind the heparan sulfate proteoglycan (HSPG) component of the ILM, which is critical for cell recognition and internalization, a need exists for administration with an excipient that functions through a CD44-independent mechanism.

An alternative, "subILM" injection method has been developed in which AAV vector is placed in a surgically induced, hydrodissected space, or bleb, between the ILM and neural retina. SubILM injections generally avoid the ILM barrier to AAV spread, as described above.

The described methods provide for effective vector transduction through noninvasive intravitreal delivery at potentially lower vector doses than those of subILM delivery. The disclosure is based, at least in part, on the discovery that coating AAV capsids having positively-charged patches on the surface prevents aggregation of these particles in the vitreous. As used herein, "surface-exposed patches" of the capsid refer to three-dimensional areas of contiguous or abutting (or substantially contiguous or abutting) cationic residues on the capsid that are exposed to milieu. Prevention of capsid aggregation enables the lateral spread of single particle suspensions of AAV to spread throughout the retina to reach target cells such as retinal ganglion cells (RGCs), Müller glia cells, and other PRs. This enhanced spread of AAV suggests that current intravitreal doses of AAV may be reduced to achieve the same transduction efficiency in target cells, which provides for a safer gene therapy.

As described herein, the pre-incubation of capsids having cationic patches with hyaluronic acid increases retinal transduction by intravitreally-delivered rAAV particles, and is independent of the capsid sequence. In some embodiments, enhancement of transduction by HA function independently of CD44. In some embodiments, HA as a vehicle does not interfere with AAV binding of HSPG in the ILM and vitreous.

In some embodiments, the described methods are suitable for use with a variety of AAV capsid serotypes and presudotypes. The described methods improve vector potency, thus lowering the concentration of rAAV particle required to achieve the desired effect. Accordingly, the described methods are capable of increasing safety and reducing expense of manufacturing or rAAV. These methods minimize the surgical risks associated with intravitreal injection, lower the cost of care, and increase the accessibility of gene therapies. The described methods increase retinal transduction of AAV in any clinical setting where AAV2 or AAV6-based capsids are delivered by intravitreal injection.

Certain Terminology

Unless defined otherwise, all technical and scientific terms used herein have the same meaning as commonly understood by one of ordinary skill in the art to which this disclosure belongs. Although any methods and compositions similar or equivalent to those described herein can be used in the practice or testing of the present disclosure, the preferred methods and compositions are described herein. For purposes of the present disclosure, the following terms are defined below:

As used herein, the terms "hyaluronic acid" and "HA" encompass hyaluronic acid, hyaluronan, Healon®, and sodium hyaluronate, without regard to the molecular weight or mass thereof. That is, these terms are meant to encompass hyaluronic acids of any molecular weight known or used in the art. The term also encompasses variants of hyaluronic acid, including but not limited to truncated and chemically modified versions of HA. A "variant" of HA is at least about 80% identical, at least about 90% identical, at least about 95% identical, at least about 96% identical, at least about 97% identical, at least about 98% identical, at least about 99% identical, at least about 99.5% identical, or at least about 99.9% identical to a wild type HA sequence.

As used herein, the terms "intravitreal injection," "intravitreal delivery," and "intravitreal administration," refer to injection of material in and to the vitreous of the eye. This term does not encompass the leakage of material, e.g. AAV vector or particles, from a bleb created by a subILM injection to the vitreous or retina.

As used herein, the term "optogenetic actuator" refers to light-sensitive ion channel proteins that are capable of modulating the activities of neurons in living tissue, e.g. neurons in retinal tissue, that have been genetically modified to express these proteins. Exemplary optogenic actuators include, but are not limited to, halorhodopsin, melanopsin, cone opsins, channel rhodopsins, bacteriorhodopsin, mammalian rhodopsin and archea-associated opsins.

The term "subject," as used herein, describes an organism, including mammals such as primates, to which treatment with the compositions according to the present disclosure can be provided. Mammalian species that can benefit from the described methods of treatment include, but are not limited to, apes; chimpanzees; orangutans; humans; monkeys; domesticated animals such as dogs and cats; livestock such as horses, cattle, pigs, sheep, goats, and chickens; and other animals such as mice, rats, guinea pigs, and hamsters.

The term "treatment" or any grammatical variation thereof (e.g., treat, treating, and treatment etc.), as used herein, includes but is not limited to, alleviating a symptom of a disease or condition; and/or reducing, suppressing, inhibiting, lessening, ameliorating or affecting the progression, severity, and/or scope of a disease or condition. Accordingly, the term "treating" includes the administration of the compounds, compositions, constructs or agents of the present invention to prevent, delay, alleviate, arrest or inhibit development of the symptoms or conditions associated with a disease. The term "therapeutic effect" refers to the reduction, elimination, or prevention of the disease, symptoms of the disease, or side effects of the disease in the subject.

As used herein, the term "pre-treatment" in some embodiments refers to the application of exogenous material to an AAV vector, prior to administration of the vector to a subject or subject cell.

The term "effective amount," as used herein, refers to an amount that is capable of treating or ameliorating a disease or condition or otherwise capable of producing an intended therapeutic effect.

As used herein, the terms "engineered" and "recombinant" cells are intended to refer to a cell into which an exogenous polynucleotide segment (such as DNA segment that leads to the transcription of a biologically active molecule) has been introduced. Therefore, engineered cells are distinguishable from naturally occurring cells, which do not contain a recombinantly introduced exogenous DNA segment. Engineered cells are, therefore, cells that comprise at least one or more heterologous nucleic acid segments introduced through the hand of man.

The term "promoter," as used herein refers to a region or regions of a nucleic acid sequence that regulates transcription.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The tern "vector," as used herein, refers to a nucleic acid molecule (typically comprised of DNA) capable of replication in a host cell and/or to which another nucleic acid segment can be operatively linked so as to bring about replication of the attached segment. A plasmid, cosmid, or a virus is an exemplary vector.

The term "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared. The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (1988) and blastn computer program based on the algorithm of Brutlag et al. (Comp. App. Biosci. 6:237-245 (1990). A preferred method for determining the best overall match between a query sequence (e.g., a sequence of the present disclosure) and a subject sequence, also referred to as a global sequence alignment, can be determined using the FASTA or blastn. In a sequence alignment the query and subject sequences are either both nucleotide sequences or both amino acid sequences. The result of said global sequence alignment is expressed as percent identity. Preferred parameters used in a FASTA amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. Whether a nucleotide is matched/aligned is determined by results of the FASTA sequence alignment. This percentage is then subtracted from the percent identity, calculated by the above FASTA program using the specified parameters, to arrive at a final percent identity score. This final percent identity score is what is used for the purposes of the present disclosure.

"Percent (%) identity" refers to the extent to which two sequences (nucleotide or amino acid) have the same residue at the same positions in an alignment. For example, "an amino acid sequence is X % identical to SEQ ID NO: Y" refers to % identity of the amino acid sequence to SEQ ID NO: Y and is elaborated as X % of residues in the amino acid sequence are identical to the residues of sequence disclosed in SEQ ID NO: Y. Generally, computer programs are employed for such calculations. Exemplary programs that compare and align pairs of sequences, include ALIGN (Myers and Miller, 1988), FASTA (Pearson and Lipman, 1988; Pearson, 1990) and gapped BLAST (Altschul et al., 1997), BLASTP, BLASTN, or GCG (Devereux et al., 1984).

The term "operably linked," as used herein, refers to that the nucleic acid sequences being linked are typically contiguous, or substantially contiguous, and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

As used herein, the term "variant" refers to a molecule (e.g. a capsid) having characteristics that deviate from what occurs in nature, e.g., a "variant" is at least about 80% identical, at least about 90% identical, at least about 95% identical, at least about 96% identical, at least about 97% identical, at least about 98% identical, at least about 99% identical, at least about 99.5% identical, or at least about 99.9% identical to the wild type capsid. Variants of a protein molecule, e.g. a capsid, may contain modifications to the amino acid sequence (e.g., having 1, 2, 3, 4, 5, 6, 7, 8, 9, 10, 10-15, or 15-20 amino acid substitutions) relative to the wild type protein sequence, which arise from point mutations installed into the nucleic acid sequence encoding the capsid protein. These modifications include chemical modifications as well as truncations, such as truncations at the N- or C-terminus of a capsid protein sequence.

As used herein, singular forms "a", "and," and "the" include plural referents unless the context clearly indicates otherwise.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes 91%, 92%, 93%, 94%, 95%, 95%, 96%, 97%, etc., as well as 91.1%, 91.2%, 91.3%, 91.4%, 91.5%, etc., 92.1%, 92.2%, 92.3%, 92.4%, 92.5%, etc., and so forth.

"About" a number, as used herein, refers to range including the number and ranging from 10% below that number to 10% above that number. "About" a range refers to 10% below the lower limit of the range, spanning to 10% above the upper limit of the range Methods Illustrative embodiments of the disclosure are described below. In some embodiments, the present disclosure provides methods of use of HA as a vehicle for administration of AAV particles to the eyes of a mammal via intravitreal injection. In some embodiments, the presently described methods provide for pre-incubation with HA and/or co-administration with HA. In some embodiments, the disclosure further provides buffers for storage of HA and AAV capsids.

In some embodiments, the intravitreal administration methods described herein are capable of enhancing the transduction capacity of any AAV capsid or capsid variant having one or more surface-exposed patches of positively-charged residues. In some embodiments, a patch of positively charged residues comprises a plurality of positively-charged residues. In some embodiments, a patch of positively-charged residues comprises at least about 2, 3, 4, 5, 6, 7, 8, 9, 10, 11, 12, 13, 15, 20, 30, 50, 60 positively-charged residues. In some embodiments, the negative charge of the hyaluronic acid interacts electrostatically with the positively-charged resides of the capsid. In some embodiments, the HA is in direct contact or association with the AAV capsid. In some embodiments, HA is not in direct contact with the AAV capsid. In some embodiments, the AAV capsid is at least partially coated by the HA. In some embodiments, the HA effectively coats the cationic patches of the capsid, shielding it from aggregating with the cationic patches of other capsids after administration to the eye. In some embodiments, this shielding effect liberates the capsid to spread laterally throughout the vitreous and transduce target RPE and PR cells, such as RGCs, Müller cells, astrocytes, and bipolar cells.

In some embodiments, the endogenous hyaluronic acid molecules covalently linked to the extracellular matrix of the vitreous and ILM of the host cell do not exert any deterrent effect on the diffusion or transduction of AAV capsids administered with HA.

In some embodiments, the mechanism of enhancement of AAV transduction and diffusion provided by pre-treatment and administration with HA is independent of interaction with the CD44 cell surface receptor. In some embodiments, the methods provided herein do not interfere with basal AAV capsid interaction with HSPG on target cell surfaces or cell surface recognition, while still facilitating AAV particles to diffuse freely throughout the vitreous.

Figure 1:
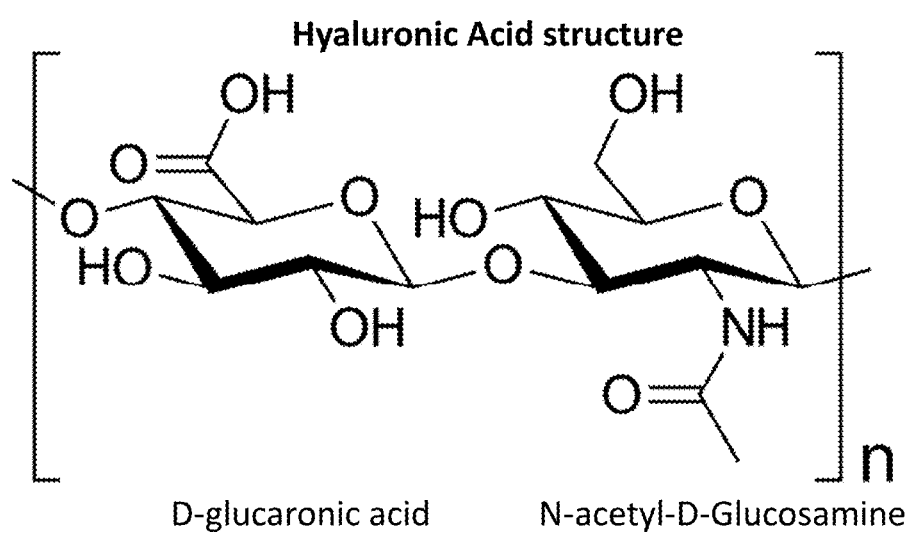

The vitreous humor is composed of 99% water, collagen fibrils and glycosaminoglycans (GAGs). The vast majority of GAGs is hyaluronic acid (HA), with the concentration of HA in the human eye being 200 ug/mL. HA is a linear concatemer of a dimer of D-glucaronic acid and N-acetyl-D-glucosamine (see FIG. 1). HA forms folds, loops and turns creating 'network' structure, which confers a viscoelastic property to the molecule. HA may concatermize into a variety of lengths which results in a variety of different molecular weights, ranging from at least 20 kilodaltons (kDa) to 5,000 kDa.

In some embodiments, provided herein are methods comprising administering rAAV particles and HA by intravitreal injection to the eyes of a subject, and/or pre-treating rAAV particles with HA prior to administration to a subject, wherein the rAAV capsid has one or more surface-exposed cationic patches, i.e., three-dimensional areas of contiguous or abutting (or substantially contiguous or abutting) cationic residues on surfaces of the capsid that are exposed to milieu. The relevant mileu may be the vitreous, the inner limiting membrane (ILM), the subretinal space, an extracellular matrix, a cell membrane, and/or a cell cytosol. In some embodiments, administration is sequential administration or co-administration.

Pre-Incubations

In some embodiments, in the methods described herein, the capsid is pre-incubated with the HA for a duration of at least about 1 minute, about 3 minutes, about 5 minutes, about 15 minutes, about 30 minutes, about 45 minutes, about 60 minutes, about 90 minutes, about 120 minutes or about 175 minutes or more prior to administration to a subject. In some embodiments, the HA is in direct contact with the AAV capsid. In some embodiments, the capsid is pre-incubated with HA for about 15 minutes. In some embodiments, the capsid is pre-incubated with HA for more than about 15 minutes.

In some embodiments, the capsid is pre-incubated with a buffer comprising HA for at least about 1 minute, about 3 minutes, about 5 minutes, about 15 minutes, about 30 minutes, about 45 minutes, about 60 minutes, about 90 minutes, about 120 minutes or about 175 minutes or more minutes. In some embodiments, the capsid is pre-incubated with a buffered comprising HA for about 15 minutes, or more than about 15 minutes. In some embodiments, the capsid is pre-incubated with a buffer comprising HA in a concentration of at least about 0.1%, 0.2%, 0.25%, 0.3%, 0.35%, 0.4%, 0.45%, 0.5%, 0.6%, 0.75%, 1.0%, 2%, 3%, 5%, 10%, 15% or 20.0% weight by volume (w/v) and BSS. In some embodiments, the capsid is pre-incubated with buffer comprising HA in a concentration of about 0.4% w/v, and one or more of BSS, artificial cerebrospinal fluid (CSF), and PBS. In some embodiments, the capsid is pre-incubated with a buffer comprising HA in a concentration of about 0.4% w/v, and one or more of BSS, artificial CSF, PBS, Ringer's lactate solution, TMN200 solution, polysorbate 20, and poloxamer 188.

In some embodiments of the described methods, the capsid is pre-incubated with HA in a concentration of at least about 0.1%, 0.2%, 0.25%, 0.3%, 0.35%, 0.4%, 0.45%, 0.5%, 0.6%, 0.75%, 1.0%, 2%, 3%, 5%, 10%, 15% or 20.0% w/v. In some embodiments, the capsid is pre-incubated with HA in a concentration of about 0.4% w/v. In some embodiments, the capsid is pre-incubated with HA in a concentration of about 0.5% w/v.

Dosage In some embodiments, the rAAV particle is administered via intravitreal injection. In some embodiments, the rAAV particle is administered via intravitreal administration in a titer of at least about $1\times10^3$ vg/ml, $1\times10^4$ vg/ml, $1\times10^5$ vg/ml, $1\times10^6$ vg/ml, $1\times10^7$ vg/ml, $1\times10^8$ vg/ml, $1\times10^9$ vg/ml, $1\times10^{10}$ vg/ml, $5\times10^{10}$ vg/ml, $1\times10^{11}$ vg/ml, $5\times10^{11}$ vg/ml, $1\times10^{12}$ vg/ml, $2\times10^{12}$ vg/ml, $3\times10^{12}$ vg/ml, $4\times10^{12}$ vg/ml, about $5\times10^{12}$ vg/ml, about $1\times10^{13}$ vg/ml, $5\times10^{13}$ vg/ml, $1\times10^{14}$ vg/ml, $5\times10^{15}$ vg/ml or $1\times10^{14}$ vg/ml In some embodiments, the rAAV particle is administered in a titer of less than $5\times10^{11}$ vg/ml. In some embodiments, the lower end of these titers represents substantially lower doses than those doses routinely used in subretinal AAV delivery.

In some embodiments, mixture of rAAV and HA is administered in an intravitreal injection. In some embodiments, the intravitreal injection is provided in a volume of about 1000 μL, about 900 μL, about 800 μL, about 700 μL, about 600 μL, about 500 μL, about 400 μL, about 300 μL, about 200 μL, about 175 μL, about 160 μL, about 145 μL, about 130 μL, about 115 μL, about 100 μL, about 90 μL, about 80 μL, about 70 μL, about 60 μL, about 55 μL, about 50 μL, about 45 μL, about 35 μL, about 20 μL, about 10 μL, about 5 μL, about 4 μL, about 3 μL, about 2 μL, about 1 μL or about 0.5 μL. In some embodiments, the intravitreal injection is provided in a volume of about 50 μL.

In certain aspects of the described methods, higher concentrations of AAV vector is delivered in a given volume of administration by intravitreal injection.

Hyaluronic Acid

In some embodiments, the HA suitable for use in the described methods is of any molecular weight known or used in the art. In some embodiments, the HA for administration and/or pre-treatment or use according the described methods has a molecular weight of at least about 4 kDa, 5 kDa, 20 kDa, 25 kDa, 30 kDa, 40 kDa, 50 kDa, 75 kDa, 100 kDa, 150 kDa, 200 kDa, 350 kDa, 500 kDa, 750 kDa, 1000 kDa, 1500 kDa, 2000 kDa, 2500 kDa, 3000 kDa, 3200 kDa, 3500 kDa, 4000 kDa or 5000 kDa. In some embodiments, the HA for administration and/or pre-treatment or use according the described methods has a molecular weight of less than about 4 kDa, 5 kDa, 20 kDa, 25 kDa, 30 kDa, 40 kDa, 50 kDa, 75 kDa, 100 kDa, 150 kDa, 200 kDa, 350 kDa, 500 kDa, 750 kDa, 1000 kDa, 1500 kDa, 2000 kDa, 2500 kDa, 3000 kDa, 3200 kDa, 3500 kDa, 4000 kDa or 5000 kDa. In some embodiments, the HA has a molecular weight in the range of about 20 kDa to about 200 kDa. In some embodiments, the HA has a molecular weight of about 20 kDa or 25 kDa. In some embodiments, the HA is uniform in molecular weight. In some embodiments, the HA has varying molecular weight. In some embodiments, administration is sequential administration or co-administration.

Administration

In some embodiments, a method for providing a mammal in need thereof with a therapeutically-effective amount of a selected therapeutic agent is described herein. In some embodiments, the therapeutic agent is encoded in a heterologous nucleic acid, or transgene, that is inserted into a recombinant AAV nucleic acid vector. In some embodiments, the nucleic acid vector comprises one or more heterologous nucleic acids comprising a sequence encoding a protein or polypeptide of interest operably linked to a promoter, wherein the one or more transgenes are flanked on each side with an ITR sequence. In some embodiments, the nucleic acid vector further comprises a region encoding a Rep protein as described herein, either contained within the region flanked by ITRs or outside the region or nucleic acid) operably linked to a promoter (e.g. an hGRK1 promoter), wherein the one or more nucleic acid regions. The ITR sequences can be derived from any AAV serotype (e.g., 1, 2, 3, 4, 5, 6, 7, 8, 9, or 10) or can be derived from more than one serotype. In some embodiments, the ITR sequences are derived from AAV2 or AAV6. In some embodiments, the ITR sequences of the first serotype are derived from AAV3, AAV2 or AAV6. In other embodiments, the ITR sequences of the first serotype are derived from AAV1, AAV5, AAV8, AAV9 or AAV10. In some embodiments, the ITR sequences are the same serotype as the capsid (e.g., AAV3 ITR sequences and AAV3 capsid, etc.).

ITR sequences and plasmids containing ITR sequences are known in the art and commercially available (see, e.g., products and services available from Vector Biolabs, Philadelphia, Pa.; Cellbiolabs, San Diego, Calif.; Agilent Technologies, Santa Clara, Ca; and Addgene, Cambridge, Mass.; and Gene delivery to skeletal muscle results in sustained expression and systemic delivery of a therapeutic protein. In some embodiments, the nucleic acid vector comprises a pTR-UF-11 plasmid backbone, which is a plasmid that contains AAV2 ITRs. This plasmid is commercially available from the American Type Culture Collection (ATCC MBA-331).

In some embodiments, the method includes at least the step of administering to one or both eyes of the mammal, an amount of one or more of the rAAV particles described herein; for a time effective to provide the mammal with a therapeutically-effective amount of the selected therapeutic agent.

In some embodiments, the described admixing or administration of rAAV and HA is a co-administration. In some embodiments, administration of rAAV and HA is a sequential administration. In some embodiments, administration of rAAV and HA is following a pre-incubation period of admixing.

In some embodiments, the method includes the step of intravitreally administering (a single time or multiple times) to either one or both eyes of the mammal, an amount of one or more rAAV particles described herein; and for a time effective to provide the mammal with a therapeutically-effective amount of the selected diagnostic or therapeutic agent.

In some embodiments, the therapeutic agent is a therapeutic protein. In some embodiments, the therapeutic protein is a neurotrophic factor or an optogenetic actuator. In some embodiments, the neurotrophic factor is BDNF, NGF, neurotrophin-3, ciliary neurotrophic factor (CNTF), ephrins and glial cell line-derived neurotrophic factors (GDNF), or a combination thereof.

In some embodiments, the optogenetic actuators of the described methods is a bacteriorhodopsin, a halorhodopsin, a channelrhodopsin, a microbial sensory rhodopsin, a mammalian rhodopsin, a cone opsin, a melanopsin; and a combination thereof. In some embodiments, the optogenetic actuator is channelrhodopsin-2 (ChR-2). In some embodiments, the disclosure provides a method for treating or ameliorating one or more symptoms of a disease, a disorder, a dysfunction, an injury, an abnormal condition, or trauma in a mammal. In some embodiments, the method includes at least the step of administering to one or both eyes of the mammal in need thereof, one or more of the described rAAV particles herein, in an amount and for a time sufficient to treat or ameliorate the one or more symptoms of the disease, the disorder, the dysfunction, the injury, the abnormal condition, or the trauma in the mammal.

In some embodiments, the disclosure provides a method for expressing a heterologous nucleic acid segment in one or more photoreceptor cells or one or more RPE cells of a mammal (e.g., a human). In some embodiments, the method includes administering (e.g. directly administering intravitreally) to one or both eyes of the mammal one or more of the rAAV particles described herein, wherein the polynucleotide further comprises at least a first polynucleotide that comprises a PR- or an RPE-cell-specific promoter operably linked to at least a first heterologous nucleic acid segment that encodes a therapeutic agent or a biologically functional fragment thereof, for a time effective to produce the therapeutic agent in the one or more PR cells or RPE cells of the mammal. In some embodiments, the therapeutic agent or a biologically functional is stably expressed in a photoreceptor cell, retinal pigment epithelium cell, retinal ganglion cell, bipolar cell, Müller glial cell or astrocyte cell, or combinations thereof.

In some embodiments, the mammal is a human. In some embodiments, the human is a neonate, a newborn, an infant, a juvenile, an adult, or a senior. In some embodiments, the subject is at least about 1 day old to more than about 100 years old. In some embodiments, the human has, is suspected of having, is at risk for developing, or has been diagnosed with one or more retinal disorders, diseases, or dystrophies. In some embodiments, the retinal disorders, diseases, and dystrophies are genetically linked, or inheritable.

In some embodiments, the production of the therapeutic agent or a biologically active fragment thereof in the cells targeted for administration of the therapeutic construct a) preserves one or more photoreceptor cells or one or more RPE cells, b) restores one or more rod- and/or cone-mediated functions, c) restores visual behavior in one or both eyes, or d) any combination thereof. In some embodiments, production of the therapeutic agent in the described methods preserves one or more PR cells, RPE cells, retinal ganglion cells, bipolar cells Müller glial cells or astrocyte cells.

In some embodiments, production of the therapeutic agent or a biologically active fragment thereof persists in the one or more photoreceptor cells or the one or more RPE cells substantially for a period of at least about one week, at least about two weeks, at least about three weeks, at least about one month, at least about two months, at least about three months, at least about six months, at least about nine months, or at least a year or more, following an initial administration of the rAAV gene therapy construct into the one or both eyes of the mammal.

In some embodiments, the described methods comprise providing a mammal in need thereof with channelrhodopsin-2, cone-opsin or biologically active fragments thereof to the ON bipolar cells of the subject. In some embodiments, the described methods comprise providing a mammal in need thereof with channelrhodopsin-2, cone-opsin, or biologically active fragments thereof to the RGCs and the Müller glial cells on the subject.

In some embodiments, a rAAV vector construct disclosed herein can be administered via an intravitreal injection, subretinal injection, orally, parenterally, intraocularly, intravenously, intranasally, intra-articularly, intramuscularly, subcutaneously, or a combination thereof. In some embodiments, a rAAV vector construct disclosed herein is administered a single time to a subject. In some embodiments, the rAAV vector construct is administered to the subject in one or more administration periods, for example at least once a day, twice a day, three times per day, once a week, twice a week, once a month, twice a month or at least one a year. In some embodiments, the AAV vector-based therapeutics may be provided successively in one or more daily, weekly, monthly, or less-frequent periods, as may be necessary to achieve treatment, or amelioration of one or more symptoms of the disease or disorder being treated. In some embodiments, a pharmaceutical composition disclosed herein can be administered a single time or multiple times, for example daily, weekly, biweekly, or monthly, hourly, or is administered upon recurrence, relapse or progression of the disease, disorder or condition being treated.

Vectors

In some embodiments, the vector described herein is a self-complementary rAAV (scAAV) vector. In some embodiments, the vector is provided to the one or both eyes by one or more administrations of an infectious adeno-associated viral particle, an rAAV virion, or a plurality of infectious rAAV particles in an amount and for a time sufficient to treat or ameliorate one or more symptoms of the disease or condition being treated.

In some embodiments, the disclosure provides improved rAAV particles that have been derived from a number of different serotypes, including but not limited to AAV1, AAV2, AAV3, AAV4, AAV5, AAV6, AAV7, AAV8, AAV9, AAV10 and combinations thereof. In some embodiments, the capsid protein sequences are set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10. In some embodiments, the capsid protein sequences comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10. In some embodiments, the capsid protein sequences comprises at least about 70%, 75%, 80%, 85%, 90%, 95%, 96%, 97%, 98%, 99% or 100% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10.

In some embodiments, the intravitreal administration methods described herein are suitable for delivery of, and enhance the transduction capacity of, any capsid having cationic patches of amino acid residues on its surface. In some embodiments, the capsid comprises AAV2, AAV6 and capsids derived from AAV2 and AAV6. In some embodiments, the capsid comprises AAV7m8, AAV-DJ, AAV2/2-MAX, AAVSHh10, AAVSHh10Y, AAV3, AAV3b, AAVLK03, AAV7BP2, AAV1(E531K), AAV6(D532N), AAV6-3 pmut, AAV2G9 or elements thereof.

In some embodiments, AAV-DJ comprises the insertion of 7 amino acids into the HSPG binding domain of the AAV2 capsid and has high expression efficiency in Müller cells following intravitreal injection. In some embodiments, the AAV7m8 capsid is closely related to AAV-DJ. In some embodiments, the AAV2/2-MAX capsid comprises five point mutations, Y272F, Y444F, Y500F, Y730F, T491V. In some embodiments, the AAVSHh10 and AAV6(D532N) capsids are derivatives of AAV6. In some embodiments, the AAV6-3 pmut is (also known as AAV6(TM6) and AAV6 (Y705+Y731F+T492V)).

In some embodiments, the capsid comprises capsids comprising non-native amino acid substitutions at amino acid residues of a wild-type AAV2 capsid as set forth in SEQ ID NO: 2. In some embodiments, the non-native amino acid substitutions comprise one or more of Y272F, Y444F, T491V, Y500F, Y700F, Y704F Y730F or a combination thereof. In some embodiments, the capsids comprises non-native amino acid substitutions at amino acid residues of a wild-type AAV6 capsid as set forth in SEQ ID NO: 6. In some embodiments, the non-native amino acid substitutions comprise one or more of Y445F, Y705F, Y731F, T492V, S663V or a combination thereof.

In some embodiments, the capsid comprises AAV2G9, a variant of AAV2.

In some embodiments, the capsid comprises a non-native amino acid substitution at amino acid residue 533 of a wild-type AAV8 capsid as set forth in SEQ ID NO: 8. In some embodiments, the non-native amino acid substitution is E533K, Y733F, or a combination thereof. In some embodiments, the capsid comprises AAV7BP2, a variant of AAV8.

In some embodiments, the capsid comprises non-native amino acid substitutions of a wild-type AAV2 capsid as set forth in SEQ ID NO: 2. In some embodiments, the capsid comprises one or more of:
 (a) Y444F;
 (b) Y444F+Y500F+Y730F;
 (c) Y272F+Y444F+Y500F+Y730F;
 (d) Y444F+Y500F+Y730F+T491V; or
 (e) Y272F+Y444F+Y500F+Y730F+T491V, or at equivalent amino acid positions corresponding thereto in any one of the wild-type AAV1, AAV3, AAV4, AAV5, AAV7, AAV9, or AAV10 capsid proteins, as set forth, respectively, in SEQ ID NO: 1, SEQ ID NO: 3, SEQ ID NO: 4, SEQ ID NO: 5, SEQ ID NO: 7, SEQ ID NO: 9, or SEQ ID NO: 10.

In some embodiments, the capsid comprises non-native amino acid substitutions of a wild-type AAV6 capsid as set forth in SEQ ID NO: 6. In some embodiments, the capsid comprises one or more of:
 (a) Y445F;
 (b) Y705F+Y731F;
 (c) T492V;
 (d) Y705F+Y731F+T492V;
 (e) S663V; or
 (f) S663V+T492V.

In various embodiments, the rAAV particles comprise one of the following capsids, i.e., capsid variants of AAV2: DGE-DF (also known as 'V1V4 VR–V'), P2-V2, P2-V3, and ME–B(Y–F+T–V). The DGE-DF capsid variant contains aspartic acid, glycine, glutamic acid, aspartic acid, and phenylalanine at amino acid positions 492, 493, 494, 499, and 500 of wild-type AAV2 VP1. The P2-V2 capsid variant contains alanine, threonine, proline, aspartic acid, phenylalanine, and aspartic acid at positions 263, 490, 492, 499, 500, and 530 of AAV2 VP1. The P2-V3 capsid variant contains asparagine, alanine, phenylalanine, alanine, asparagine, valine, threonine, arginine, aspartic acid, and aspartic acid at positions 263, 264, 444, 451, 454, 455, 459, 527, 530, and 531 of AAV2 VP1. The ME–B(Y–F+T–V) capsid variant contains aspartic acid, glycine, glutamic acid, aspartic acid, and phenylalanine at positions 492, 493, 494, 499, and 500 of AAV2 VP1, respectively, SAAGADXAXDS (SEQ ID NO: 5) at positions 546-556 of AAV2 VP1, and the following substitutions: Y272F, Y444F, and T491V.

In other embodiments, the rAAV particles comprise a capsid selected from AAV6(3 pMut), AAV2(quadYF+T–V), or AAV2(trpYF). In some embodiments, the rAAV particles comprise any of the capsid variants described in International Patent Publication No. WO 2018/156654.

In some embodiments, described herein are methods of administering HA with rAAV particles comprising a DGE-DF capsid, P2-V2 capsid, P2-V3 capsid, or ME-B(Y-F+T-V) capsid for the enhanced transduction of said rAAV particles in retinal cells. In some embodiments, the described methods comprise the administration of HA with rAAV particles comprising a capsid selected from AAV2(Y444F), AAV2 (Y444F+Y500F+Y730F), AAV2(Y272F+Y444F+Y500F+Y730F), AAV2(Y444F+Y500F+Y730F+T491V) and AAV2 (Y272F+Y444F+Y500F+Y730F+T491V), AAV6(Y445F), AAV6(Y705F+Y731F), AAV6(Y705F+Y731F+T492V), AAV6(S663V), AAV6(T492V) or AAV6(S663V+T492V).

In some embodiments, the rAAV polynucleotide or nucleic acid vectors of the present disclosure may be comprised within a virion having a serotype that is selected from the group consisting of AAV serotype 1, AAV serotype 2, AAV serotype 3, AAV serotype 4, AAV serotype 5, AAV serotype 6, AAV serotype 7, AAV serotype 8, AAV serotype 9, or AAV serotype 10, or any other serotype as known to one of ordinary skill in the viral arts.

Cargo

In some embodiments, the disclosure further provides populations and pluralities of rAAV polynucleotide or nucleic acid vectors, virions, infectious viral particles, or host cells that comprise a multi-mutated capsid protein and one or more nucleic acid segments that include an RPE- or a PR-cell-specific promoter operably linked to a selected polynucleotide encoding at least a first diagnostic and/or a first therapeutic molecule.

In some embodiments, the disclosure provides composition and formulations that include one or more of the proteins or biological active fragments thereof, nucleic acid segments or biological active fragments thereof, viral polynucleotide or biological active fragments thereof, nucleic acid vectors, host cells, or viral particles of the present disclosure together with one or more pharmaceutically-acceptable buffers, diluents, or excipients. In some embodiments, the compositions are included in one or more diagnostic or therapeutic kits, for diagnosing, preventing, treating or ameliorating one or more symptoms of a mammalian disease, injury, disorder, trauma or dysfunction. In some embodiments, the diagnostic or therapeutic kit comprises a kit for delivery of a therapeutic agent to photoreceptors and/or RPE cells of the mammalian eye.

In some embodiments, described herein is a method for providing a mammal in need thereof with a diagnostically- or therapeutically-effective amount of a selected therapeutic agent, the method comprising providing to a cell, tissue or organ of a mammal in need thereof, an amount of one or more of the described rAAV multi-capsid mutant particles or nucleic acid vectors; and for a time effective to provide the mammal with a diagnostically- or a therapeutically-effective amount of the selected therapeutic agent.

In some embodiments, the disclosure provides a method for diagnosing, preventing, treating, or ameliorating at least one or more symptoms of a disease, a disorder, a dysfunction, an injury, an abnormal condition, or trauma in a mammal. In some embodiments, the method includes at least the step of administering to a mammal in need thereof one or more of the described rAAV particles or nucleic acid vectors, in an amount and for a time sufficient to diagnose, prevent, treat or ameliorate the one or more symptoms of the disease, disorder, dysfunction, injury, abnormal condition, or trauma in the mammal.

In some embodiments, the disclosure provides a method of transducing a population of mammalian cells, and particular one or more ocular cells in the human eye. In some embodiments, the method includes at least the step of introducing into one or more cells of the population, a composition that comprises an effective amount of one or more of the rAAV particles or nucleic acid vectors described herein. In some embodiments, delivery of the described gene therapy constructs to one or more cells subretinally, permitted the high-efficiency transduction of photoreceptors and RPE cells.

In some embodiments, the disclosure provides isolated nucleic acid segments that encode one or more of the AAV mutant capsid proteins as described herein, and provides recombinant nucleic acid vectors comprising said segments.

In some embodiments, the present disclosure provides compositions, as well as therapeutic and/or diagnostic kits that include one or more of the described AAV particle or nucleic acid vector compositions, formulated with one or more additional ingredients, or prepared with one or more instructions for their use.

In some embodiments, the disclosure provides compositions comprising recombinant adeno-associated viral (AAV) vectors, virions, viral particles, and pharmaceutical formulations thereof, useful in methods for delivering genetic material encoding one or more beneficial or therapeutic product(s) to mammalian cells and tissues. In some embodiments, the compositions and methods of the disclosure provide a significant advancement in the art through their use in the treatment, prevention, and/or amelioration of symptoms of one or more mammalian diseases.

In some embodiments, the rAAV particles of the described methods additionally includes a vector comprising a heterologous nucleic acid sequence that encodes at least a first diagnostic or biologically active fragment thereof, or therapeutic agent or a biologically active fragment thereof operably linked to an RPE- or a PR-cell-specific promoter capable of expressing the segment in one or more cells that have been transformed with the vector. In some embodiments, the PR-cell-specific promoter is human rhodopsin kinase (hGRK1), IRBP, rod opsin, NRL, GNAT2e-IRBP, L/M opsin, cone arrestin promoter, a biologically active fragment of any of these or combination thereof. In some embodiments, a RPE-cell-specific promoter comprises VMD2 (BEST1) or RPE65 promoter.

In some embodiments, the surface-exposed amino acid-modified rAAV particles or nucleic acid vectors of the present disclosure comprises one or more enhancer sequences that are each operably linked to the nucleic acid segment that encodes the diagnostic or therapeutic molecule of interest or biologically active fragments thereof. The surface-exposed amino acid-modified rAAV particles or nucleic acid vectors of the present disclosure comprises one or more enhancer sequences. In some embodiments, the enhancer sequence is CMV enhancer, a synthetic enhancer, a photoreceptor-specific-specific enhancer, a retinal pigment epithelial cell-specific enhancer, a vascular-specific enhancer, an ocular-specific enhancer, a neural cell-specific enhancer, a retinal cell-specific enhancer, biologically active fragments of these, and any combination thereof.

In some embodiments, the promoter is a tissue-specific promoter. In some embodiments, the tissue-specific promoter is a photoreceptor specific- and/or a RPE cell-specific promoter.

In some embodiments, the nucleic acid vector comprises a post-transcriptional regulatory sequences or a polyadenylation signals. In some embodiments, the nucleic acid vector comprises a woodchuck hepatitis virus post-transcription regulatory element (WPRE), a polyadenylation signal sequence, an intron/exon junctions/splicing signal, or any combination thereof.

In some embodiments, a cargo described herein is a nucleic acid sequence, a gene, an encoded protein, or an encoded active fragment of a protein disclosed herein.

In some embodiments, the improved rAAV particle comprise a sequence that encodes a diagnostic or therapeutic protein, polypeptide or a biologically active fragment of a molecular marker, a photosensitive opsin, an adrenergic agonist, an anti-apoptosis factor, an apoptosis inhibitor, a cytokine receptor, a cytokine, a cytotoxin, an erythropoietic agent, a glutamic acid decarboxylase, a glycoprotein, a growth factor, a growth factor receptor, a hormone, a hormone receptor, an interferon, an interleukin, an interleukin receptor, a kinase, a kinase inhibitor, a nerve growth factor, a netrin, a neuroactive peptide, a neuroactive peptide receptor, a neurogenic factor, a neurogenic factor receptor, a neuropilin, a neurotrophic factor, a neurotrophin, a neurotrophin receptor, an N-methyl-D-aspartate antagonist, a plexin, a protease, a protease inhibitor, a protein decarboxylase, a protein kinase, a protein kinase inhibitor, a proteolytic protein, a proteolytic protein inhibitor, a semaphorin, a semaphorin receptor, a serotonin transport protein, a serotonin uptake inhibitor, a serotonin receptor, a serpin, a serpin receptor, a tumor suppressor, or any combination thereof. In some embodiments, a photosensitive opsin comprises a rhodopsin, a melanopsin, a cone opsin, a channel rhodopsin, or a bacterial, archea-associated opsin, biologically active fragments of any of these or combinations thereof.

In some embodiments, the rAAV particles of the present disclosure comprises a nucleic acid segment that encodes the polypeptide RPE65, Bestrophin (BEST1), REP1, MERTK, SOD2, MYO6A, MFRP, LRAT, KCNJ13, ornithine aminotransferase (OAT), a biologically active fragment of any of these or any combination thereof.

In some embodiments, the rAAV particle comprises a nucleic acid segment that encodes the polypeptide CNTF, GDNF, BDNF, IL6, LIF, XIAP, STAT3, a biologically active fragment of any of these or any combination thereof.

In certain embodiments, the rAAV particle comprises a nucleic acid segment that encodes nyctalopin (nyx), metabotropic glutamate receptor 6-mGluR6 (Grm6), transient receptor potential melastatin 1 (TRPM1), G protein coupled receptor 179 (GPR179), and G proteins, G$\beta$5, G$\beta$3, G$\alpha 0_{1/2}$, G$\gamma$13, RGS7, RGS11, R8AP, and any combination or peptide fragment thereof.

In some embodiments, described herein is a rAAV nucleic acid vector that comprises at least a first nucleic acid segment that encodes one or more diagnostic, therapeutic agents or biologically active fragments thereof that alter, inhibit, reduce, prevent, eliminate, or impair the activity of one or more endogenous biological processes in a mammalian cell suitably transformed with the vector of interest. In some embodiments, the diagnostic, therapeutic agent or biologically active fragment thereof comprises a molecule that selectively inhibits or reduces the effects of one or more metabolic processes, dysfunctions, disorders, or diseases.

In some embodiments, the defect is caused by injury or trauma to the mammal for which treatment is desired. In some embodiments, the defect is caused by the over-expression of an endogenous biological compound. In some embodiments; the defect is caused by the under-expression or lack of one or more endogenous biological compounds.

In some embodiments, the rAAV nucleic acid vectors and expression systems of the present disclosure comprises a second nucleic acid segment that comprises, consists essentially of, or consists of, a enhancer, a regulatory element, one or more transcriptional elements, or any combination thereof, that alter, improve, regulate, and/or affect the transcription of the nucleotide sequence of interest expressed by the rAAV particles.

In some embodiments, the rAAV nucleic acid vectors of the present disclosure comprises a second nucleic acid segment that comprises, consists essentially of, or consists of, a CMV enhancer, a synthetic enhancer, a cell-specific enhancer, a tissue-specific enhancer, or any combination thereof. In some embodiments, the second nucleic acid segment further comprises, consists essentially of, or consists of, one or more intron sequences, one or more post-transcriptional regulatory elements, or one or more enhancers from rhodopsin, melanopsin, cone opsins, channel rhodopsins, bacterial or archea-associated opsins, an adrenergic agonist, an anti-apoptosis factor, an apoptosis inhibitor, a cytokine receptor, a cytokine, a cytotoxin, an erythropoietic agent, a glutamic acid decarboxylase, a glycoprotein, a growth factor, a growth factor receptor, a hormone, a hormone receptor, an interferon, an interleukin, an interleukin receptor, a kinase, a kinase inhibitor, a nerve growth factor, a netrin, a neuroactive peptide, a neuroactive peptide receptor, a neurogenic factor, a neurogenic factor receptor, a neuropilin, a neurotrophic factor, a neurotrophin, a neurotrophin receptor, an N-methyl-D-aspartate antagonist, a plexin, a protease, a protease inhibitor, a protein decarboxylase, a protein kinase, a protein kinase inhibitor, a proteolytic protein, a proteolytic protein inhibitor, a semaphorin, a semaphorin receptor, a serotonin transport protein, a serotonin uptake inhibitor, a serotonin receptor, a serpin, a serpin receptor, or a tumor suppressor. In some embodiments, the second nucleic acid segment further comprises, consists essentially of, or consists of, one or more intron sequences, one or more post-transcriptional regulatory elements, or one or more enhancers from RPE65, Bestrophin (BEST1), REP1, MERTK, SOD2, MYO6A, MFRP, LRAT, KCNJ13, or ornithine aminotransferase (OAT). In some embodiments, the second nucleic acid segment comprises, consists essentially of, or consists of, one or more intron sequences, one or more post-transcriptional regulatory elements, or one or more enhancers from RPE65, Bestrophin (BEST1), REP1, MERTK, SOD2, MYO6A, MFRP, LRAT, KCNJ13, ornithine aminotransferase (OAT), CNTF, GDNF, BDNF, IL6, LIF, XIAP, or STAT3.

In some embodiments, the rAAV particles comprise a polynucleotide that comprises, consists essentially of, or consists of, one or more polylinkers, restriction sites, and/or multiple cloning region(s) to facilitate insertion (cloning) of one or more selected genetic elements, genes of interest, and/or one or more therapeutic or diagnostic molecules into the rAAV particle at a selected site within the vector.

In some embodiments, the exogenous polynucleotide(s) is delivered into suitable host cells by the rAAV particles comprising nucleic acid vectors described herein are of mammalian origin, with polynucleotides encoding one or more polypeptides or peptides of, e.g., human, non-human primate, porcine, bovine, ovine, feline, canine, equine, epine, caprine, or lupine origin.

In some embodiments, the exogenous polynucleotide(s) that is delivered into host cells by the described particles or viral vectors in some embodiments encodes one or more proteins, one or more polypeptides, one or more peptides, one or more enzymes, or one or more antibodies (or antigen-binding fragments thereof), a biologically active fragment of any of these or any combination thereof. In some embodiments, the exogenous polynucleotides express one or more siRNAs, ribozymes, antisense oligonucleotides, PNA molecules, or any combination thereof. In some embodiments, two or more different molecules is produced from a single rAAV expression system, or alternatively, a selected host cell may be transfected with two or more unique rAAV expression systems, each of which may comprise one or more distinct polynucleotides that encode a therapeutic agent.

In some embodiments, provided herein are rAAV nucleic acid vectors that are comprised within an infectious adeno-associated viral particle or a virion, as well as pluralities of such virions or infectious particles. In some embodiments, the vectors and virions disclosed herein is in a composition with one or more diluents, buffers, physiological solutions or pharmaceutical vehicles, formulated for administration to a mammal in one or more diagnostic, therapeutic, and/or prophylactic regimens. In some embodiments, the vectors, virus particles, virions, and pluralities thereof of the present disclosure are provided in excipient formulations that are acceptable for veterinary administration to selected livestock, exotics, domesticated animals, and companion animals (including pets and such like), as well as to non-human primates, zoological or otherwise captive specimens.

In embodiments, described herein are recombinant adeno-associated virus virion particles (e.g., improved transduction efficiency particles), compositions, and host cells that comprise, consist essentially of, or consist of, one or more of the rAAV particles described herein, such as for example pharmaceutical formulations of the vectors intended for intravitreal or subretinal administration to a mammalian eye.

Kits

In some embodiments, described herein are kits comprising one or more of the described rAAV particles or nucleic acid vectors (as well as one or more virions, viral particles, transformed host cells or pharmaceutical compositions comprising such vectors); and instructions for using such kits in one or more therapeutic, diagnostic, and/or prophylactic clinical embodiments are also provided by the present disclosure. In some embodiments, the kits further comprise one or more reagents, restriction enzymes, peptides, therapeutics, pharmaceutical compounds, or means for delivery of the composition(s) to host cells, or to an animal (e.g., syringes, injectables, and the like). In some embodiments, the kits disclosed herein is treating, preventing, or ameliorating the symptoms of a disease, deficiency, dysfunction, and/or injury. In some embodiments, the kit includes components for the large-scale production of the viral vectors themselves, such as for commercial sale, or for use by others, including e.g., virologists, medical professionals, and the like.

Use

In some embodiments, described herein are methods of use of the described rAAV particles or vectors, virions, expression systems, compositions, and host cells described herein in the preparation of medicaments for diagnosing, preventing, treating or ameliorating at least one or more symptoms of a disease, a dysfunction, a disorder, an abnormal condition, a deficiency, injury, or trauma in an animal, and in particular, in the eye. In some embodiments, the methods comprise direct administration to the vitreous of one or both eyes of a mammal in need thereof, one or more of the described vectors, virions, viral particles, host cells, compositions, or pluralities thereof, in an amount and for a time sufficient to diagnose, prevent, treat, or lessen one or more symptoms of such a disease, dysfunction, disorder, abnormal condition, deficiency, injury, or trauma in one or both eyes of the affected animal.

In some embodiments, described herein are compositions comprising one or more of the described rAAV particles, expression systems, infectious AAV particles, and host cells. In some embodiments, the compositions further comprise at least a first pharmaceutically-acceptable excipient for use in the manufacture of medicaments and methods involving therapeutic administration of such rAAV particles or nucleic acid vectors. In some embodiments, pharmaceutical formulations are suitable for intravitreal administration into one or both eyes of a human or other mammal.

In some embodiments, described herein are methods of use of the particles, vectors, virions, expression systems, compositions, and host cells described herein in a method for treating or ameliorating the symptoms or in the preparation of medicaments for treating or ameliorating the symptoms of various deficiencies in an eye of a mammal, and in particular one or more deficiencies in human photoreceptors or RPE cells. In some embodiments, the diseases and disorders of the eye (e.g., caused by one or more genetic deficiencies in a PR or PRE cell) for treatment or amelioration of symptoms include Retinitis pigmentosa, Leber Congenital Amaurosis, Age Related Macular Degeneration (AMD) wet AMD, dry AMD, uveitis, Best disease, Stargardts disease, Usher Syndrome, Geographic Atrophy, Diabetic Retinopathy, Retinoschisis, Achromatopsia, Choroideremia, Bardet Biedl Syndrome, glycogen storage diseases (ocular manifestation) or a combination thereof. In some embodiments, the methods comprise intravitreal or subretinal administration to one or both eyes of a subject in need thereof, one or more of the described particles vectors, virions, host cells, or compositions, in an amount and for a time sufficient to treat or ameliorate the symptoms of such a deficiency in the affected mammal. In some embodiments, the methods comprise prophylactic treatment of an animals suspected of having such conditions, or administration of such compositions to those animals at risk for developing such conditions either following diagnosis, or prior to the onset of symptoms. In some embodiments, the rAAV particle is not comprised in a chimeric viral/non-viral nanoparticle.

Storage and Manufacturing Buffers

In some embodiments, provided herein are buffers for storage and manufacturing of rAAV particles disclosed herein. In some embodiments, a pharmaceutical composition disclosed herein comprises a buffered solution.

In some embodiments, described herein are buffers for storage of a mixture of rAAV vectors or capsids and HA. In some embodiments, the described buffers comprise HA in a concentration of at least about 0.05%, 0.1%, 0.2%, 0.25%, 0.3%, 0.35%, 0.4%, 0.45%, 0.5%, 0.6%, 0.75%, 1.0%, 2%, 3%, 4%, 5%, 6%, 7%, 8%, 9%, 10%, or 15% weight by volume (w/v) and BSS. In some embodiments, the described buffers comprise HA in a concentration of at least about 0.1%, 0.2%, 0.25%, 0.3%, 0.35%, 0.4%, 0.45%, 0.5%, 0.6%, 0.75%, 1.0%, 2%, 3%, 4%, 5%, 6%, 7%, 8%, 9%, 10%, or 15% weight by volume (w/v) and BSS, and one or more of the following excipients: artificial cerebrospinal fluid (CSF), PBS, Ringer's lactate solution, TMN200 solution, polysorbate 20, and poloxamer 188 (known commercially as Pluronic F-68®), and/or additional excipients or combinations thereof.

In some embodiments, the buffer comprises HA in a concentration of about 0.4% w/v, and one or more of BSS, artificial CSF, or PBS. In some embodiments, the buffer comprises HA in a concentration of about 0.4% w/v, and one or more of BSS, artificial CSF, PBS, Ringer's lactate solution; and optionally TMN200 solution, polysorbate 20 (Tween 20), and poloxamer 188. In some embodiments, the described buffers comprise Tween 20 in a concentration of about at least 0.005%, 0.009%, 0.01% 0.014%, 0.02%, 0.1%, 0.2% 0.5% or 1% and poloxamer 100 in a concentration of about 0.005%, 0.009%, 0.01%, 0.02%, 0.1%, 0.2% 0.5% or 1%.

In some embodiments, the described buffers consist essentially of HA in a concentration of about HA in a concentration of 0.1%, 0.2%, 0.25%, 0.3%, 0.35%, 0.4%, 0.45%, 0.5%, 0.6%, 0.75%, or 1.0% w/v, BSS, artificial CSF, PBS and Ringer's lactate solution.

In some embodiments, described herein are elution buffers for manufacturing rAAV particles that comprise HA. In some embodiments, the buffers may be used to elute AAV capsids from an affinity column immediately prior to packaging and formulation to a final product. In some embodiments, the buffers prevent aggregation of AAV capsids having surface-exposed cationic patches from aggregating during manufacturing. In some embodiments, the buffers comprise a pH lower than 7. In some embodiments, the buffers comprise a pH lower than 5. In some embodiments, the buffers are acidic. In some embodiments, the buffers are basic. In some embodiments, a pharmaceutical composition disclosed herein is acidic. In some embodiments, a pharmaceutical composition disclosed herein s basic. In some embodiments, a pharmaceutical composition disclosed herein is neutral. In some embodiments, a composition described herein can have a pH of 1, 2, 3, 4, 5, 6, 7, 8, 9, 10, 11, 12, 13, or 14.

In some embodiments, the buffers comprise HA in a concentration of 0.1%, 0.2%, 0.25%, 0.3%, 0.35%, 0.4%, 0.45%, 0.5%, 0.6%, 0.75%, or 1.0% w/v.

In some embodiments, described herein are methods of manufacturing an rAAV particle comprising purifying AAV capsids wherein capsids are eluted from an affinity column containing a resin selected from AAV-X or AVB affinity resins, or another resin known in the art.

rAAV Particles

Aspects of the disclosure relate to recombinant adeno-associated virus (rAAV) particles or preparations of such particles for delivery of one or more nucleic acid vectors comprising a sequence encoding a Rep protein, and/or a protein or polypeptide of interest, into various tissues, organs, and/or cells. In some embodiments, the rAAV particle is delivered to a host cell in the presence of a Rep protein as described herein.

Recombinant adeno-associated virus (rAAV) vectors have been used successfully for in vivo gene transfer in numerous pre-clinical animal models of human disease, and have been used successfully for long-term expression of a wide variety of therapeutic. AAV vectors have also generated long-term clinical benefit in humans when targeted to immune-privileged sites, e.g., ocular delivery for Leber's congenital amaurosis. An advantage of this vector is its comparatively low immune profile, eliciting only limited inflammatory responses and, in some cases, even directing immune tolerance to transgene products. Nonetheless, the therapeutic efficiency, when targeted to non-immune privileged organs, has been limited in humans due to antibody and $CD8^+$ T cell responses against the viral capsid, while in animal models, adaptive responses to the transgene product have also been reported.

Adeno-associated virus (AAV) is used for ocular gene therapy due to its efficiency, persistence and low immunogenicity. Identifying vectors capable of transducing PRs via the vitreous has historically relied on identifying which serotypes have native tropism for this cell type following local delivery. Several serotypes have been used to successfully target transgene to PRs following subretinal injection (including, e.g., AAV2, AAV5 and AAV8) with all three demonstrating efficacy in experiments performed across multiple mammalian species (e.g., mouse, rat, dog, pig and non-human primate).

In some embodiments, AAV2 and AAV8 vectors comprises point mutations of surface-exposed tyrosine residues (tyrosine to phenylalanine,Y—F) display to increase transgene expression in retinal cell types relative to unmodified vectors following both subretinal and intravitreal injection. In some embodiments, AAV2 comprises a triple mutant (designated "triple Y→F"). In some embodiments, an AAV2 comprises a quadruple mutant ("quad Y→F"). In some embodiments, an AAV comprises directed mutagenesis of surface-exposed threonine (T) or serine (S) residues to non-native amino acids at one of more of those amino acids. In some embodiments, an AAV comprises an Y→F and/or T→V/T→A mutations.

In some embodiments, the rAAV is an rAAV described herein.

In some embodiments, the rAAV nucleic acid vector comprises a single-stranded (ss) or self-complementary (sc) AAV nucleic acid vectors, such as single-stranded or self-complementary recombinant viral genomes. In some embodiments, the rAAV particle is not comprised in a chimeric viral/non-viral nanoparticle.

The wild-type AAV genome is a single-stranded deoxyribonucleic acid (ssDNA), either positive- or negative-sensed. The genome comprises two inverted terminal repeats (ITRs), one at each end of the DNA strand, two open reading frames (ORFs): rep and cap between the ITRs, and an insert nucleic acid positioned between the ITRs and optionally comprising a transgene. The rep ORF comprises four overlapping genes encoding Rep proteins required for the AAV life cycle. The cap ORF comprises overlapping genes encoding capsid proteins: VP1, VP2 and VP3, which interact together to form the viral capsid. VP1, VP2 and VP3 are translated from one mRNA transcript, which can be spliced in two different manners: either a longer or shorter intron can be excised resulting in the formation of two isoforms of mRNAs: a~2.3 kb- and a~2.6 kb-long mRNA isoform. The capsid forms a supramolecular assembly of approximately 60 individual capsid protein subunits into a non-enveloped, T-1 icosahedral lattice capable of protecting the AAV genome. The mature capsid is composed of VP1, VP2, and VP3 (molecular masses of approximately 87, 73, and 62 kDa respectively) in a ratio of about 1:1:10.

Recombinant AAV (rAAV) particles may comprise a nucleic acid vector, which may comprise at a minimum: (a) one or more transgenes comprising a sequence encoding a protein or polypeptide of interest or an RNA of interest (e.g., a siRNA or microRNA), or one or more nucleic acid regions comprising a sequence encoding a Rep protein; and (b) one or more regions comprising inverted terminal repeat (ITR) sequences) flanking the one or more heterologous nucleic acid regions (e.g., transgenes). In some embodiments, the nucleic acid vector is between 4kb and 5kb in size (e.g., 4.2 to 4.7 kb in size). In some embodiments, the nucleic acid vector further comprises a region encoding a Rep protein as described herein. Any nucleic acid vector described herein may be encapsidated by a viral capsid, such as an AAV6 capsid or another serotype (e.g., a serotype that is of the same serotype as the ITR sequences), which may comprises a modified capsid protein as described herein. In some embodiments, the nucleic acid vector is circular. In some embodiments, the nucleic acid vector is single-stranded. In some embodiments, the nucleic acid vector is double-stranded. In some embodiments, a double-stranded nucleic acid vector may be, for example, a self-complimentary vector that contains a region of the nucleic acid vector that is complementary to another region of the nucleic acid vector, initiating the formation of the double-strandedness of the nucleic acid vector.

Accordingly, in some embodiments, an rAAV particle or rAAV preparation containing such particles comprises a viral capsid and a nucleic acid vector as described herein, which is encapsidated by the viral capsid. In some embodiments, the insert nucleic acid of the nucleic acid vector comprises (1) one or more transgenes comprising a sequence encoding a protein or polypeptide of interest, (2) one or more nucleic acid regions comprising a sequence that facilitates expression of the transgene (e.g., a promoter), and (3) one or more nucleic acid regions comprising a sequence that facilitate integration of the transgene (optionally with the one or more nucleic acid regions comprising a sequence that facilitates expression) into the genome of the subject.

Helper Plasmids

In some embodiments a plasmid containing the nucleic acid vector sequence disclosed herein is combined with one or more helper plasmids, e.g., that contain a rep gene (e.g., encoding Rep78, Rep68, Rep52 and Rep40) and a cap gene (encoding VP1, VP2, and VP3, including a modified VP3 region as described herein). In some embodiments, a helper plasmid is transfected into a producer cell line such that the rAAV particle can be packaged and subsequently purified.

In some embodiments, the one or more helper plasmids comprises a first helper plasmid comprising a rep gene and a cap gene and/or a second helper plasmid comprising a E1a gene, a E1b gene, a E4 gene, a E2a gene, a VA gene or a combination thereof. In some embodiments, the rep gene is a rep gene derived from AAV2. In some embodiments the cap gene is derived from AAV2. In some embodiments, the cap gene includes modifications to the gene in order to produce a modified capsid protein described herein. In certain embodiments, the rep gene comprises Rep78, Rep68, Rep52 or Rep40. In certain embodiments, the cap gene comprises VP1, VP2, VP3 or variants thereof. In some embodiments, the helper plasmid comprises pDM, pDG, pDPlrs, pDP2rs, pDP3rs, pDP4rs, pDP5rs, pDP6rs, pDG (R484E/R585E), or pDP8.ape plasmids.

Production

In some embodiments, described herein is a method of rAAV particle production. In some embodiments, one or more helper plasmids are produced or obtained. In some embodiments, the one or more helper plasmids comprise rep and cap ORFs for the desired AAV serotype and the adenoviral VA, E2A (DBP), and E4 genes. In some embodiments, the rep and cap ORFs for the desired AAV serotype and the adenoviral VA, E2A (DBP), and E4 genes are under the transcriptional control of their native promoters. In some embodiments, the cap ORF comprises one or more modifications to produce a modified capsid protein as described herein. In some embodiments, HEK293 cells (available from ATCC®) are transfected via CaPO4-mediated transfection, lipids or polymeric molecules such as Polyethylenimine (PEI) with the helper plasmid(s) and a plasmid containing a nucleic acid vector described herein. In some embodiments, the HEK293 cells are incubated for at least about 60 hours to allow for rAAV particle production. In some embodiments, a Sf9-based producer stable cell line is infected with a single recombinant baculovirus containing the nucleic acid vector. In some embodiments, HEK293 or BHK cell lines are infected with a HSV containing the nucleic acid vector and optionally one or more helper HSVs. Ins some embodiments, the helper HSVs contain rep and cap ORFs as described herein and the adenoviral VA, E2A (DBP), and E4 genes under the transcriptional control of their native promoters. In some embodiments, the HEK293, BHK, or Sf9 cells are then incubated for at least 60 hours to allow for rAAV particle production. In some embodiments, the rAAV particles are purified. In some embodiments, the rAAV particles are purified by iodixanol step gradient, CsCl gradient, chromatography, or polyethylene glycol (PEG) precipitation.

Kits and Uses for Improved rAAV Delivery

In some embodiments, described herein is a mixture of rAAV particles and hyaluronic acid comprised within a kit for diagnosing, preventing, treating or ameliorating one or more symptoms of a mammalian disease, injury, disorder, trauma or dysfunction. In some embodiments, kits are useful in diagnosis, prophylaxis, and/or therapy, and in the treatment, prevention, and/or amelioration of one or more defects in the mammalian eye as discussed herein. In some embodiments, a kit can comprise a pharmaceutical composition disclosed herein. In some embodiments, a kit can comprise a pharmaceutical composition in unit dose form. In some embodiments, a method can comprise making a kit disclosed herein. In some embodiments, a kit can comprise one or more container, bottle, or ampoule. In some embodiments, a kit comprises instructions for use.

In some embodiments, described herein are methods comprising the use of the buffers and compositions described herein in the manufacture of a medicament for treating, preventing or ameliorating the symptoms of a disease, disorder, dysfunction, injury or trauma comprising the treatment, prevention, and/or prophylaxis of a disease, disorder or dysfunction, and/or the amelioration of one or more symptoms of such a disease, disorder or dysfunction.

In some embodiments, described herein are methods for treating or ameliorating the symptoms of such a disease, injury, disorder, or dysfunction in one or both eyes of a mammal, and of a human. In some embodiments, the methods comprise at least the step of administering to a mammal in need thereof, one or more of the rAAV particles as described herein, in an amount and for a time sufficient to treat or ameliorate the symptoms of such a disease, injury, disorder, or dysfunction in one or both eyes of the mammal.

Pharmaceutical Compositions Comprising rAAV Particles

In some embodiments, the improved rAAV delivery methods described herein permit the delivery of smaller titers of viral particles in order to achieve the same transduction efficiency as that obtained using higher levels of conventional, rAAV methods. In some embodiments, the method comprises the administration of therapeutically-effective amounts of the described compositions comprising a single administration. In some embodiments, the method comprises a single injection of sufficient numbers of infectious particles to provide therapeutic benefit to the patient undergoing such treatment. In some embodiments, the method comprises multiple, or successive administrations of the AAV vector compositions, either over a relatively short, or over a relatively prolonged period. In some embodiments, the number of infectious particles administered to a subject is at least about $10^1$, $10^2$, $10^3$, $10^4$, $10^5$, $10^6$, $10^7$, $10^8$, $10^9$, $10^{10}$, $10^{11}$, $10^{12}$, $10^{13}$, or even higher, infectious particles/mL. In some embodiments, the infectious particles are given either as a single dose (or divided into two or more administrations, etc.,) as may be required to achieve therapy of the particular disease or disorder being treated. In some embodiments, the method comprises administering two or more different rAAV particle- or vector-based compositions, either alone, or in combination with one or more other diagnostic agents, drugs, bioactives, to achieve the desired effects of a particular regimen or therapy. In some embodiments, lower titers of infectious particles will be required when practicing the described methods of pre-treating and co-administering AAV capsids with HA when compared to the titers of infectious particles required when AAV capsids are not pre-treated or co-administered with HA. In some embodiments, the capsid sequence comprises at least about 70%, 75%, 80%, 85%, 90%, 95%, 96%, 97%, 98%, 99% or 100% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10. In some embodiments, the capsid sequence comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10. In some embodiment, the rAAV particle is not comprised in a chimeric viral/non-viral nanoparticle.

In some embodiments, the rAAV particle comprises a therapeutic agent-encoding a nucleic acid segment under the control of one or more promoters. In some embodiments, to bring a sequence "under the control of" a promoter, one positions the 5' end of the transcription initiation site of the transcriptional reading frame generally between about 1 and about 50 nucleotides "downstream" of (i.e., 3' of) the chosen promoter. In some embodiments, the "upstream" promoter stimulates transcription of the DNA and promotes expression of the encoded polypeptide. In some embodiments, recombinant vector constructs are those that include a capsid-protein modified rAAV vector that contains an RPE cell- or a photoreceptor cell-specific promoter, operably linked to at least one nucleic acid segment encoding one or more diagnostic, and/or therapeutic agents.

In some embodiments, the method comprises introducing one or more exogenous proteins, polypeptides, peptides, ribozymes, and/or antisense oligonucleotides, to a particular cell transfected with the vector. In some embodiments, the rAAV particles described herein are used to deliver one or more exogenous polynucleotides to a selected host cell, e.g., to one or more selected cells within the mammalian eye.

In some embodiments, the number of viral particles administered to a subject may be on the order ranging from at least about $10^1$ to $10^{20}$ particles/ml or $10^3$ to $10^{15}$ particles/ml, or any values therebetween for either range, such as for example, about $10^1$, $10^2$, $10^3$, $10^4$, $10^5$, $10^6$, $10^7$, $10^8$, $10^9$, $10^{10}$, $10^{11}$, $10^{12}$, $10^{13}$, $10^{14}$ $10^{15}$, $10^{16}$, $10^{17}$, $10^{18}$, $10^{19}$ or $10^{20}$ particles/ml. In some embodiments, viral particles of higher than $10^{13}$ particles/ml may be administered. In some embodiments, the number of viral particles administered to a subject may be on the order ranging from $10^6$ to $10^{14}$ vector genomes(vgs)/ml or $10^3$ to $10^{15}$ vgs/ml, or any values therebetween for either range. In some embodiments, the number of viral particles administered to a subject may be on the order of about $10^1$, $10^2$, $10^3$, $10^4$, $10^5$, $10^6$, $10^7$, $10^1$, $10^9$, $10^{10}$, $10^{11}$, $10^{12}$, $10^{13}$, or $10^{14}$ vgs/ml. In some embodiments, viral particles of higher than $10^{13}$ vgs/ml are be administered. In some embodiments, the viral particles are administered as a single dose. In some embodiments, the viral particles are divided into two or more administrations as may be required to achieve therapy of the particular disease or disorder being treated. In some embodiments, 0.0001 ml to 10 ml, e.g., 0.001 ml, 0.01 ml, 0.1 ml, 1 ml, 2 ml, 5 ml or 10 ml, are delivered to a subject.

In some embodiments, described herein are formulations of one or more viral-based compositions described herein in pharmaceutically acceptable solutions for administration to a cell or an animal, either alone or in combination with one or more other modalities of therapy, and in particular, for therapy of human cells, tissues, and diseases affecting the subject.

In some embodiments, rAAV particles described herein are administered in combination with other agents as well, such as, e.g., proteins or polypeptides or various pharmaceutically-active agents, including one or more systemic or topical administrations of therapeutic polypeptides, biologically active fragments, or variants thereof. In some embodiments, the compositions may be purified from host cells or other biological sources, or alternatively may be chemically synthesized as described herein.

In some embodiment, the composition comprises a pharmaceutically-acceptable buffer, excipients or carrier solutions. In some embodiments, the compositions are formulated for oral, parenteral, intravitreal, intraocular, intravenous, intranasal, topical, intra-articular, intramuscular administration or a combination thereof.

In some embodiments, a composition disclosed herein comprises a pharmaceutically acceptable carrier. In some embodiments, pharmaceutically acceptable carriers include, but are not limited to, buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); or preservatives.

In some embodiments, these formulations comprise at least about 0.1% of the therapeutic agent (e.g., rAAV particle) or more. In some embodiments, the percentage of the active ingredient(s) is between at least about 0.01%, 0.02%, 0.05%, 0.1%, 0.5% 1% or 2% and about 70% or 80% or more of the weight or volume of the total formulation.

In some embodiments, term "excipient" refers to a diluent, adjuvant, carrier, or vehicle with which the rAAV particle is administered. In some embodiments, the pharmaceutical excipients comprises sterile liquids, such as water or oils, including those of petroleum oil such as mineral oil, vegetable oil such as peanut oil, soybean oil, or sesame oil, animal oil, or oil of synthetic origin. In some embodiments, liquid carriers comprise saline solutions, aqueous dextrose, glycerol solutions or combinations thereof. In some embodiments, excipients and vehicles comprise HA, BSS, artificial CSF, PBS, Ringer's lactate solution, TMN200 solution, polysorbate 20, poloxamer 100 or a combination thereof.

In some embodiments, the administration of therapeutically-effective amounts of the composition comprise a single administration, such as for example, a single injection of sufficient numbers of viral particles to provide therapeutic benefit to the patient undergoing such treatment. In some embodiments, administration of a therapeutically effective about of the composition comprises multiple, or successive administrations of the compositions, either over a relatively short, or a relatively prolonged period of time, as may be determined by the medical practitioner overseeing the administration of such compositions.

In some embodiments, the composition comprises rAAV particles or nucleic acid vectors either alone, or in combination with one or more additional active ingredients, which may be obtained from natural or recombinant sources or chemically synthesized.

EXAMPLES

Example 1—In Vitro Experiments

It was sought to determine whether AAV capsids containing cationic patches of surface-exposed capsid residues (i.e. AAV2 and AAV6) exhibited enhanced transduction of HEK293T (human) and 661 W cells (a murine cone-derived photoreceptor cell line) following pre-incubation with HA.

Figure 2A:
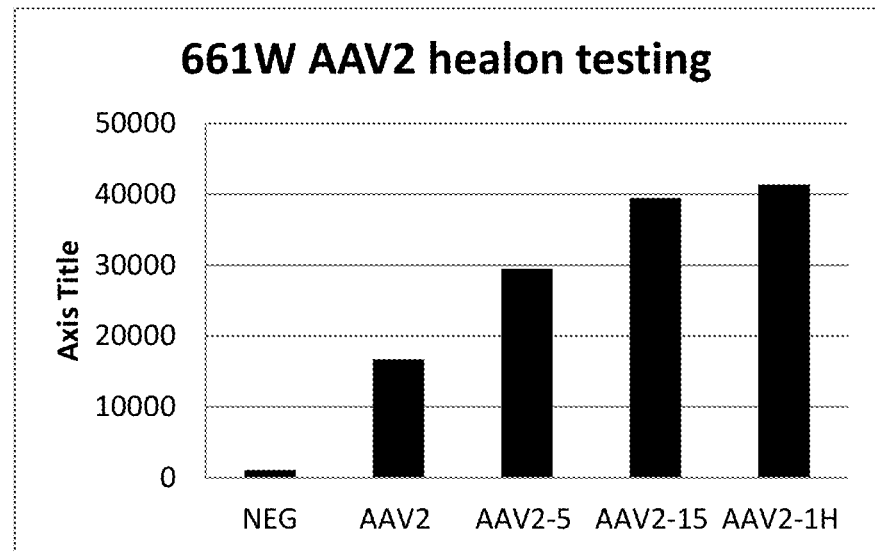

AAV2 capsids were preincubated with Healon® in a ratio of 3:1 (AAV:Healon®) and then injected into cells at a multiplicity of infection (MOI) of 2000. Controls included uninfected cells and cells infected with AAV vector alone. AAV-mediated mCherry reporter expression data demonstrated that HA increased transduction of 661 W cells after administration in vitro of rAAV2 particles following pre-incubation with HA (at 5 minutes, 15 minutes, and 1 hour prior to infection) in FIG. 2A.

Figure 3:
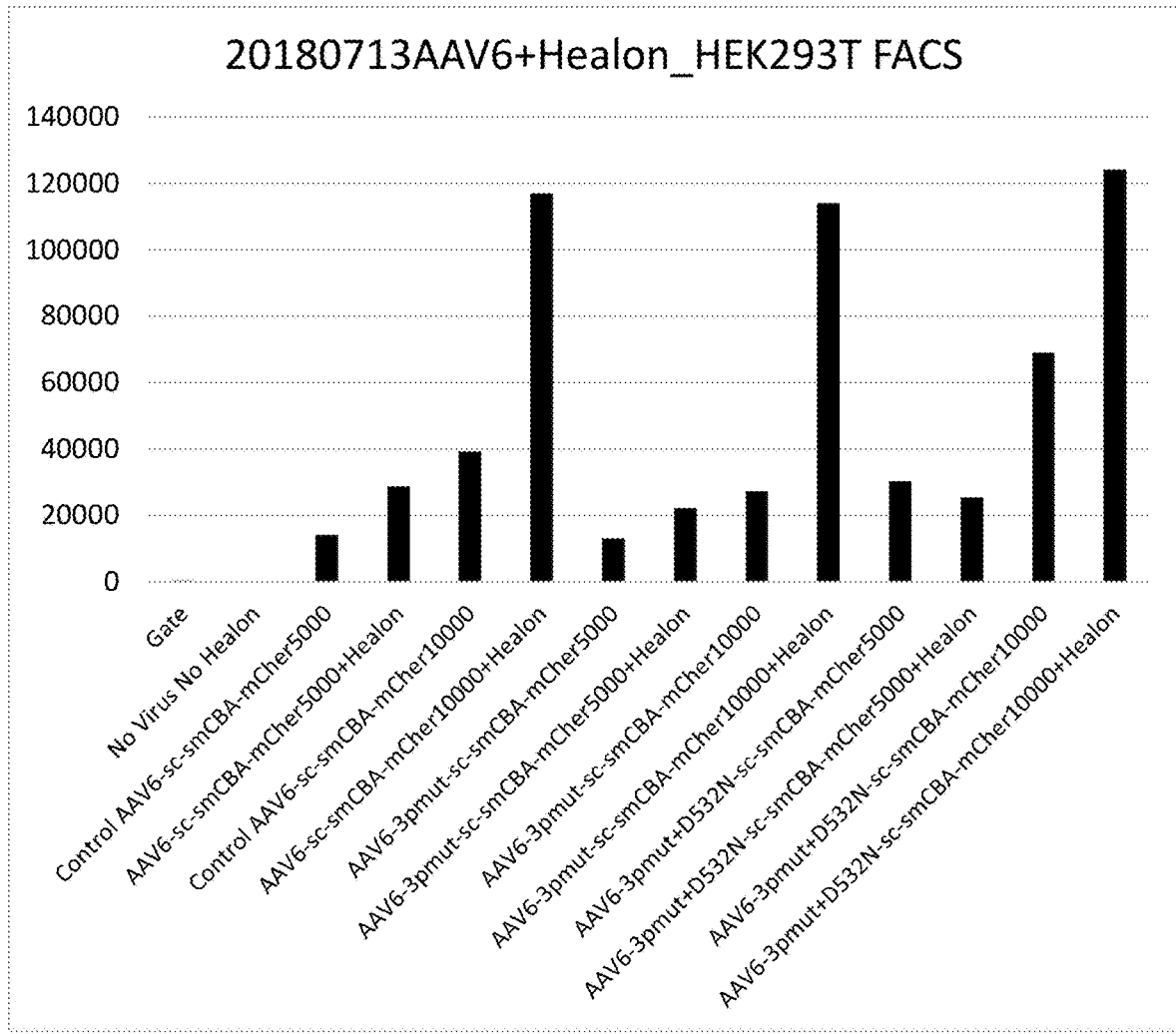

AAV6 capsid harbors patches of positively-charged residues, similar to AAV2. Both serotypes show improvements in transduction after pre-incubation with HA. As with AAV2, HA pre-treatment and co-administration increased transduction of mCherry reporter (under the control of a ubiquitous CBA promoter) in HEK293T cells in vitro after administration of self-complementary rAAV6-based vectors injected at multiplicities of infection (MOIs) of 5000 to 10,000, as shown in FIG. 3. For this experiment, transduction efficiencies of capsid variants AAV6(D532N) and AAV6-3 pmut, in the presence and absence of HA pre-incubation, were evaluated.

Figure 2B:
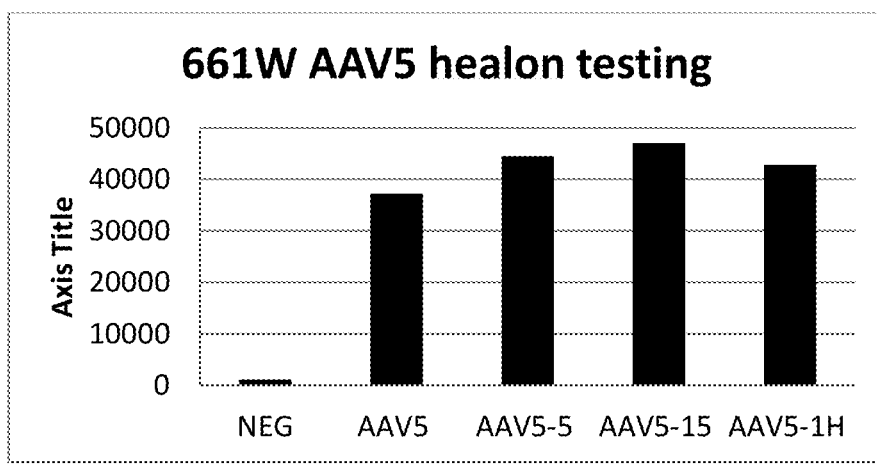

By contrast, AAV5, which has a uniformly negative charge on the capsid surface, failed to exhibit enhanced transduction (see FIGS. 2 and 3).

Next, it was established that HA-mediated enhancement of transduction was not dependent on binding to the CD44 cell surface receptor. First, it was confirmed via immunocytochemistry that HEK293T and 661W did not exhibition expression of CD44 (see FIGS. 4A-4C), but that ARPE19 cells, a human RPE cell line that is known to express CD44, exhibited CD44 expression.

When a similar experiment as that performed with AAV6-based capsids in HEK293 was performed in ARPE19 cells, the pre-treatment of AAV with HA was shown to reduce transduction. This inhibition was overcome by digesting the HA with hyaluronidase, which reduces the side-chain length of HA such that it is no longer recognized by CD44.

As noted, pre-incubation of AAV2 with HA inhibits transduction of ARPE19 cells, and ARPE19 cells express CD44. However, pre-incubation of AAV2 with HA that has been digested with hyaluronidase enhances transduction of ARPE19 cells. When hyaluronidase cleaves HA, the resulting shortened concatemer is generally 50-100 monomers long (having a molecular weight of 20-40 kDa). The affinity of HA for CD44 substantially decreases with decreasing molecular weight, particularly around the 20 kDa molecular weight mark (monovalent interaction vs. divalent interaction).

Figure 5:
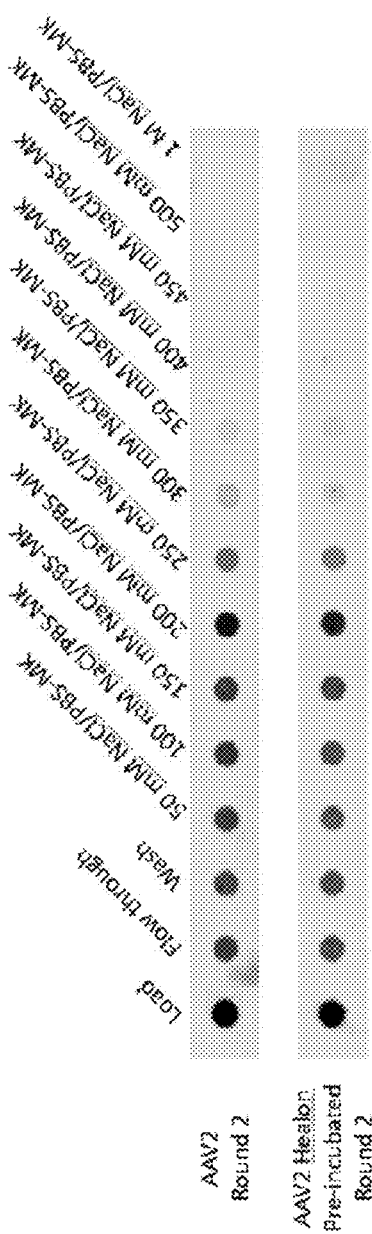
FIG. 5 illustrates the results of a heparan binding elution profile of AAV2 capsid alone and AAV2 capsid pre-incubated with Healon® at different salt concentrations between 50 mM and 1M NaCl. HA pre-treatment does not alter interaction of AAV2 capsids with heparan sulfate proteoglycan (HSPG) on cell membranes.

Next, it was asked whether HA-coated AAV2 still recognizes the heparan sulfate proteoglycan (HSPG) receptor footprint required for the cell recognition and internalization events necessary for intravitreal transduction of retina. To assess this, HA was incubated with AAV2, and then binding to heparin, which is the established proxy material for HSPG, was evaluated. As illustrated in the elution profile depicted in FIG. 5, HA treatment did not alter binding to heparin. The heparin affinity of HA-coated AAV2 differed insignificantly from AAV2 alone, indicating that the HA-mediated transduction enhancements have little to no impact on the canonical HSPG binding of AAV capsids.

Taken together, the results indicate that improvements in transduction mediated by HA are not CD44-dependent.

Example 2—In Vivo Experiments

It was then determined whether pre-incubation of several AAV2-based capsid variants with HA facilitated enhanced retinal transduction in intravitreally-injected mice relative to virus alone (see FIGS. 6A-6B). 10 µL of virus capsid ($2\times10^{12}$ vector genome copies (vg)/mL) was mixed with 10 µL Healon®(molecular weight of 5 million kDa) within 30 minutes of injection. The virus-only control was composed of 10 µL of virus ($2\times10^{12}$ vg/mL) mixed with 10 µL Balanced Salt solution (BSS)+Tween20. The final vector concentration was $1\times10^{12}$ vg/mL. Intravitreal injections were performed on 4 week old Nrl-GFP mice and fundus images were taken at two weeks, and four weeks post injection. Four capsids-all variants of AAV2 that retain cationic surface-exposed patches-were tested. These capsids are known in the art as 'DGE-DF', 'P2-V2', 'P2-V3', and 'ME–B(Y–F+T–V)' (see International Patent Publication No. WO 2018/156654). Gain and integration settings were consistent throughout all images (see FIGS. 7A-7B, 8A-8B, 9A-9B, and 10A-10B).

Five weeks post-injection, electroretinogram (ERG) and FACS analyses were performed. Flow cytometry was used to analyze transduction of retinal cells by measuring mCherry expression, and gating was done using an un-injected eye's whole retina. Fundus images at 2 weeks and 4 weeks post-injection, along with aggregated flow cytometry quantifications of the signals in these images, are shown for DGE-DF in FIGS. 7A-7C, P2-V2 in FIGS. 8A-8C, P2-V3 in FIGS. 9A-9C, and ME–B(Y–F+T–V) in FIGS. 10A-10C. Flow cytometry data for all four capsids overall was aggregated and is shown in FIG. 11.

Each of the four capsid variants exhibited improved retinal transduction after pre-incubation with HA. It was also confirmed that pre-treatment and co-administration of capsid with HA had no significant impact on retinal function after intravitreal delivery, as assessed by ERG data (see FIGS. 12A-12E). The amplitudes of A- and B-waves in rod and cone cells did not vary to a significant degree following treatment with HA.

Taken together, the results indicate that pre-treatment and co-administration with HA enhances transduction efficiencies in vivo across several different capsid types having surface-exposed cationic patches. Pre-treatment with HA represents a powerful novel method for improving AAV transduction, and lowering these AAV titer necessary to achieve a desired transduction, without modifying the residues of the capsid itself.

It should be understood that the examples and embodiments described herein are for illustrative purposes only and that various modifications or changes in light thereof will be suggested to persons skilled in the art and are to be included within the spirit and purview of this application and the scope of the appended claims. All references, including publications, patent applications and patents, cited herein are hereby incorporated by reference to the same extent as if each reference was individually and specifically indicated to be incorporated by reference and was set forth in its entirety herein. Recitation of ranges of values herein are merely intended to serve as a shorthand method of referring individually to each separate value falling within the range, unless otherwise indicated herein, and each separate value is incorporated into the specification as if it were individually recited herein.

All of the compositions and methods described and claimed herein can be made and executed without undue experimentation in light of the present disclosure. While the compositions and methods have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are chemically and/or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A composition comprising a rAAV particle comprising: (a) a capsid admixed with hyaluronic acid and (b) a polynucleotide encoding a therapeutic agent, wherein the hyaluronic acid has an average molecular weight of 4 kDa to 5,000 kDa, wherein the therapeutic agent (a) preserves one or more photoreceptor cells, one or more retinal ganglion cells, one or more retinal bipolar cells, or one or more retinal pigment epithelial (RPE) cells; (b) restores one or more rod-and/or cone-mediated functions; (c) restores visual behavior in one or both eyes; or (d) any combination thereof.

2. The composition of claim 1, wherein the hyaluronic acid has an average molecular weight of 20 kDa to 5,000 kDa.

3. The composition of claim 1, wherein the hyaluronic acid is present at a concentration of 0.1% to 1.0% weight by volume.

4. A composition comprising a rAAV particle comprising: (a) a capsid admixed with hyaluronic acid and (b) a polynucleotide encoding a therapeutic agent, wherein the hyaluronic acid has an average molecular weight of 4 kDa to 5,000 kDa, wherein the polynucleotide is operably linked to a regulatory sequence that directs expression of the polynucleotide in a retinal ganglion cell.

5. A composition comprising a rAAV particle comprising: (a) a capsid admixed with hyaluronic acid and (b) a polynucleotide encoding a therapeutic agent, wherein the hyaluronic acid has an average molecular weight of 4 kDa to 5,000 kDa, wherein the therapeutic agent is a neurotrophic factor or an optogenetic actuator.

6. The composition of claim 5, comprising the neurotropic factor, wherein the neurotropic factor comprises brain derived neurotrophic factor (BDNF), nerve growth factor (NGF), neurotrophin-3, ciliary neurotrophic factor (CNTF), leukemia inhibitory factor (LIF), an ephrin, or glial cell line-derived neurotrophic factor (GDNF); or a combination of two or more thereof.

7. The composition of claim 5, comprising the optogenetic actuator, wherein the optogenetic actuator comprises a bacteriorhodopsin, a halorhodopsin, a channelrhodopsin, a microbial sensory rhodopsin, a mammalian rhodopsin, a cone opsin, or a melanopsin; or a combination of two or more thereof.

8. The composition of claim 1, comprising a promoter operably linked to the polynucleotide encoding the therapeutic agent.

9. The composition of claim 8, wherein the promoter is a photoreceptor specific promoter or a retinal pigment epithelial (RPE) cell-specific promoter.

10. The composition of claim 8, wherein the promoter is a smCBA promoter, a rhodopsin kinase promoter, an IRBP promoter, a bipolar cell promoter, an NRL promoter, a GNAT2 promoter, an opsin promoter, a cone arrestin promoter, a VMD2 (BEST1) promoter, or a RPE65 promoter.

11. The composition of claim 1, wherein the rAAV particle is present in the composition in a titer having a range of about $1 \times 10^{10}$ vector genomes (vg)/ml to about $5 \times 10^{13}$ vg/ml.

12. The composition of claim 1, wherein the rAAV particle comprises a capsid selected from AAV2, AAV2 (Y444F), AAV2(trpYF), AAV2 (quadYF), AAV2(quadYF+T-V), AAV2/2-MAX, DGE-DF, ME-B, ME-B(Y-F+T-V), P2-V2, and P2-V3.

13. The composition of claim 1, wherein the rAAV particle comprises a capsid selected from AAV6, AAV7m8, AAV-DJ, AAV3, AAV3b, AAV6-3 pMut, AAVSHh10, AAVSHh10Y, and AAVLK03.

14. The composition of claim 1, wherein the composition is formulated for intravitreal injection.

15. The composition of claim 14, wherein the composition is formulated with one or more excipients from the group comprising balanced salt solution, polysorbate 20, poloxamer 188, and TMN200.

16. The composition of claim 14, wherein the composition is formulated with balanced salt solution and polysorbate 20.

17. The composition of claim 14, wherein the composition is formulated with poloxamer 188 and TMN200.

18. The composition of claim 4, wherein the regulatory sequence is selected from the group consisting of: a woodchuck hepatitis virus post-transcription regulatory element (WPRE), a polyadenylation signal sequence, an intron/exon junction/splicing signal, or a combination thereof.

* * * * *